US012622580B2

(12) United States Patent
Shi et al.

(10) Patent No.: US 12,622,580 B2
(45) Date of Patent: May 12, 2026

(54) SYSTEM AND METHOD FOR IMAGE GUIDED TRANSORAL ROBOTIC SURGERY USING AN IMAGING COMPATIBLE ORAL RETRACTOR SYSTEM

(71) Applicants: Dartmouth-Hitchcock Clinic, Lebanon, NH (US); The Trustees of Dartmouth College, Hanover, NH (US)

(72) Inventors: Yuan Shi, Hanover, NH (US); Xiaotian Wu, East Greenwich, RI (US); Joseph A. Paydarfar, Hanover, NH (US); Ryan J. Halter, Orford, NH (US)

(73) Assignees: Dartmouth-Hitchcock Clinic, Lebanon, NH (US); The Trustees of Dartmouth College, Hanover, NH (US)

( * ) Notice: Subject to any disclaimer, the term of this patent is extended or adjusted under 35 U.S.C. 154(b) by 1101 days.

(21) Appl. No.: 17/689,924

(22) Filed: Mar. 8, 2022

(65) Prior Publication Data

US 2022/0330804 A1     Oct. 20, 2022

Related U.S. Application Data

(60) Provisional application No. 63/158,822, filed on Mar. 9, 2021.

(51) Int. Cl.
*A61B 1/267* (2006.01)
*A61B 1/24* (2006.01)
(Continued)

(52) U.S. Cl.
CPC ................ *A61B 1/24* (2013.01); *A61B 1/267* (2013.01); *A61B 6/44* (2013.01); *A61B 6/512* (2024.01); *A61B 17/0293* (2013.01); *A61B 34/30* (2016.02)

(58) Field of Classification Search
CPC ........... A61B 1/24; A61B 1/267; A61B 34/30; A61B 6/512; A61B 6/44; A61B 17/0293
See application file for complete search history.

(56) References Cited

U.S. PATENT DOCUMENTS

| | | | |
|---|---|---|---|
| 10,499,802 B1 | 12/2019 | Chen | |
| 10,582,836 B1 * | 3/2020 | Wu ..................... | A61B 1/00149 |

(Continued)

OTHER PUBLICATIONS

"OpenIGTLink/Slicer—NAMIC Wiki.", <https://www.na-mic.org/wiki/OpenIGTLink/Slicer> (Aug. 25, 2021 ).

(Continued)

*Primary Examiner* — JaMel M Nelson
*Assistant Examiner* — Erica Hartsell Funk
(74) *Attorney, Agent, or Firm* — Loginov & Associates, PLLC; William A. Loginov

(57) ABSTRACT

A support rig for a medical instrument can hold a medical instrument that is inserted into a patient in a fixed position and orientation relative to patient, so that the position and orientation of the medical instrument is not affected by the breathing or other motion of the patient. The support rig and medical instrument can be radiolucent and non-metallic, so that an image can be taken of the patient while the medical instrument is inserted in the patent and held by the support rig. The radiolucent support rig and medical instrument can allow for imaging, including x-ray, CT, and/or MRI, to occur simultaneously during the surgery. Surgical outcomes can be improved by using imaging to provide information about a tumor and/or anatomical structures during surgery.

11 Claims, 47 Drawing Sheets

(51) Int. Cl.

| | |
|---|---|
| *A61B 6/00* | (2006.01) |
| *A61B 6/51* | (2024.01) |
| *A61B 17/02* | (2006.01) |
| *A61B 34/30* | (2016.01) |

(56) References Cited

U.S. PATENT DOCUMENTS

| | | | |
|---|---|---|---|
| 2004/0005529 A1 | 1/2004 | O'Neill | |
| 2012/0130176 A1* | 5/2012 | Minson | A61B 1/267 |
| | | | 600/196 |
| 2013/0296654 A1 | 11/2013 | Olsen | |
| 2017/0071586 A1 | 3/2017 | Wang | |
| 2017/0135706 A1* | 5/2017 | Frey | A61B 17/1671 |
| 2018/0318010 A1 | 11/2018 | Botzenhart | |

OTHER PUBLICATIONS

Chang, J., Wu, X., Kahng, P. W., Halter, R. J. and Paydarfar, J. A., "Cadaver head holder for transoral surgical simulation," The Laryngoscope 128(10), 2341-2344 (2018).

Dixon, B. J., Daly, M. J., Chan, H., Vescan, A., Witterick, I. J. and Irish, J. C., "Augmented image guidance improves skull base navigation and reduces task workload in trainees: a preclinical trial," The Laryngoscope 121(10), 2060-2064 (2011).

Fried, M. P., Moharir, V. M., Shin, J., Taylor-Becker, M. and Morrison, P., "Comparison of endoscopic sinus surgery with and without image guidance," Am. J. Rhinol. 16(4), 193-197 (2002).

Galletti, B., Gazia, F., Freni, F., Sireci, F. and Galletti, F., "Endoscopic sinus surgery with and without computer assisted navigation: A retrospective study," Auris. Nasus. Larynx 46(4), 520-525 (2019).

Giotakis, A. I., Kral, F., Freysinger, W., Markart, S. and Riechelmann, H., "Missed paranasal sinus compartments in sinus surgery with and without image-guidance systems: a pilot feasibility study," Int. J. Comput. Assist. Radiol. Surg. 14(5), 895-902 (2019).

Hockstein, N. G. and O'Malley, B. W., "Transoral robotic surgery," Oper. Tech. Otolaryngol.—Head Neck Surg. 19(1), 67-71 (2008).

Javer, A. R. and Genoway, K. A., "Patient quality of life improvements with and without computer assistance in sinus surgery: outcomes study," J. Otolaryngol. 35(6), 373-379 (2006).

Jiang, R.-S. and Liang, K.-L., "Image-guided sphenoidotomy in revision functional endoscopic sinus surgery," Allergy Rhinol. Provid. RI 5(3), 116-119 (2014).

Johnson, D. E., Burtness, B., Leemans, C. R., Lui, V. W. Y., Bauman, J. E. and Grandis, J. R., "Head and neck squamous cell carcinoma," 1, Nat. Rev. Dis. Primer 6(1), 1-22 (2020).

Lee, S. Y., Park, Y. M., Byeon, H. K., Choi, E. C. and Kim, S.-H., "Comparison of oncologic and functional outcomes after transoral robotic lateral oropharyngectomy versus conventional surgery for T1 to T3 tonsillar cancer," Head Neck 36(8), 1138-1145 (2014).

Moore, E. J., Abel, K. M. V., Price, D. L., Lohse, C. M., Olsen, K. D., Jackson, R. S. and Martin, E. J., "Transoral robotic surgery for oropharyngeal carcinoma: Surgical margins and oncologic outcomes," Head Neck 40(4), 747-755 (2018).

O'Malley Jr, B. W., Weinstein, G. S., Snyder, W. and Hockstein, N. G., "Transoral Robotic Surgery (TORS) for Base of Tongue Neoplasms," The Laryngoscope 116(8), 1465-1472 (2006).

Shi, Y., Wu, X., Paydarfar, J. A. and Halter, R. J., "Imaging-compatible oral retractor system for use in image-guided transoral robotic surgery," Med. Imaging 2021 Image-Guid. Proced. Robot. Interv. Model. 11598, 1159807, International Society for Optics and Photonics (2021).

Siegel, R. L., Miller, K. D., Fuchs, H. E. and Jemal, A., "Cancer Statistics, 2021," CA. Cancer J. Clin. 71(1), 7-33 (2021).

Stelter, K., Ertl-Wagner, B., Luz, M., Muller, S., Ledderose, G., Siedek, V., Berghaus, A., Arpe, S. and Leunig, A., "Evaluation of an image-guided navigation system in the training of functional endoscopic sinus surgeons. A prospective, randomised clinical study," Rhinology 49(4), 429-437 (2011).

Stelter, K., Theodoraki, M. N., Becker, S., Tsekmistrenko, V., Olzowy, B. and Ledderose, G., "Specific stressors in endonasal skull base surgery with and without navigation," Eur. Arch. Oto-Rhino-Laryngol. Off. J. Eur. Fed. Oto-Rhino-Laryngol. Soc. EUFOS Affil. Ger. Soc. Oto-Rhino-Laryngol.—Head Neck Surg. 272(3), 631-638 (2015).

Weinstein, G. S., Quon, H., Newman, H. J., Chalian, J. A., Malloy, K., Lin, A., Desai, A., Livolsi, V. A., Montone, K. T., Cohen, K. R. and O'Malley, B. W., "Transoral Robotic Surgery Alone for Oropharyngeal Cancer: An Analysis of Local Control," Arch. Otolaryngol. Neck Surg. 138(7), 628-634 (2012).

Wu, X., Paydarfar, J. and Halter, R., "Intraoperative deformation during laryngoscopy of irradiated and non-irradiated patients," Med. Imaging 2018 Image-Guid. Proced. Robot. Interv. Model., R. J. Webster and B. Fei, Eds., 45, SPIE, Houston, United States (2018).

Yu, H., Wang, X., Zhang, S., Zhang, L., Xin, P. and Shen, S. G., "Navigation-guided en bloc resection and defect reconstruction of craniomaxillary bony tumours," Int. J. Oral Maxillofac. Surg. 42(11), 1409-1413 (2013).

* cited by examiner

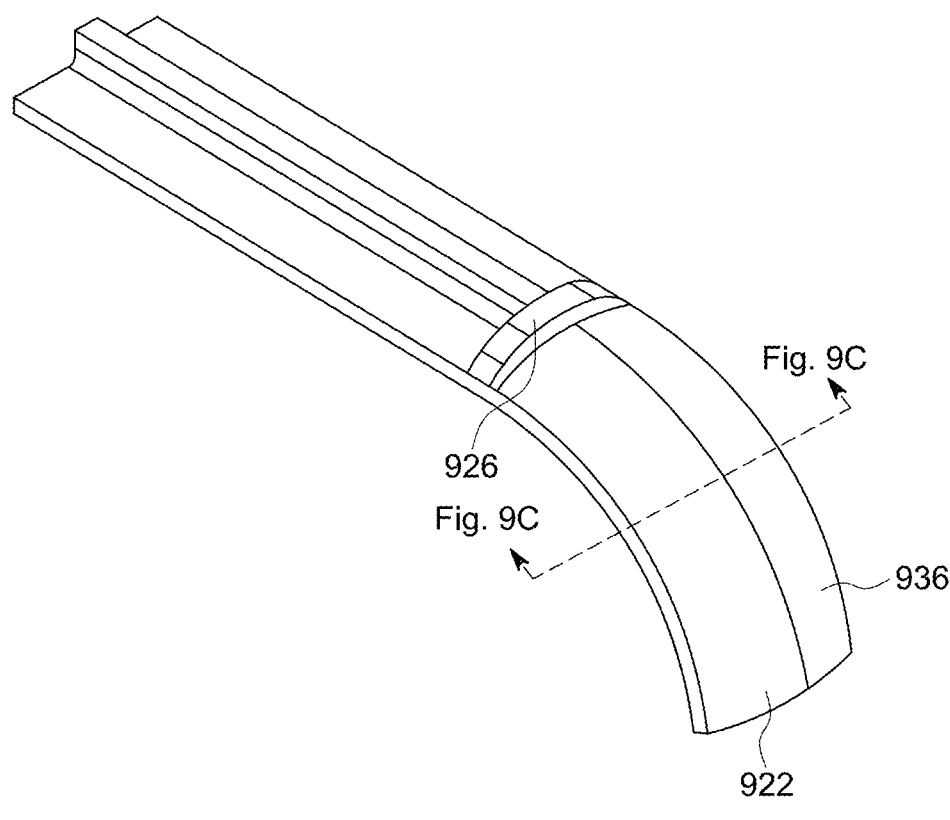
926
Fig. 9C
Fig. 9C
936
922
FIG. 9B
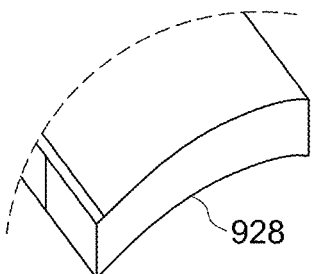
928
FIG. 9C

910

940

916

920

934

932

930

1920

Suture

2300

SYSTEM AND METHOD FOR IMAGE GUIDED TRANSORAL ROBOTIC SURGERY USING AN IMAGING COMPATIBLE ORAL RETRACTOR SYSTEM

RELATED APPLICATION

This application claims the benefit of U.S. Provisional Application Ser. No. 63/158,822, entitled SYSTEM AND METHOD FOR IMAGE GUIDED TRANSORAL ROBOTIC SURGERY USING AN IMAGING COMPATIBLE ORAL RETRACTOR SYSTEM, filed Mar. 9, 2021, the teachings of which are expressly incorporated herein by reference.

STATEMENT REGARDING FEDERALLY SPONSORED RESEARCH OR DEVELOPMENT

This invention was made with U.S. government support under the National Cancer Institute Grant Number R21CA246158, awarded by the National Institutes of Health. The government has certain rights in this invention.

FIELD OF THE INVENTION

This invention relates to image guided Trans-Oral Robotic Surgery (TORS) and more particularly, to TORS using an imaging compatible oral retractor system.

BACKGROUND OF THE INVENTION

Head and neck cancer (oral cavity, pharynx, and larynx) represents the fifth most common cancers worldwide. Minimally invasive approaches such as trans-oral robotic surgery (TORS) have demonstrated improved outcomes for managing cancers of the pharynx and larynx with decreased morbidity when compared with traditional open surgical treatments. Because of the limited haptic feedback available during robotic surgery, surgeons are required to rely on preoperative imaging for guidance. However, the placement of necessary retractors during TORS to create the surgical working volume deforms the tumor and soft tissues, which renders the preoperative imaging inaccurate.

It would be desirable for surgeons to be able to use intraoperative imaging such as CT (computed tomography) and MR (magnetic resonance) imaging during surgery. Intraoperative imaging in conjunction with image-guided surgical navigation can provide real time feedback of the deformed state and help assess the extent of tumor and location of critical structures. Currently-available metallic retractors typically used in TORS (e.g. FK and Crowe-Davis retractors) cause significant streak artifacts in CT imaging and cannot safely be used in MRI. It would be desirable to have an oral retractor system that is compatible with these imaging systems. It would be further desirable to provide a device that is customizable to the anatomical specificities of an individual patient's anatomy.

SUMMARY OF THE INVENTION

The present invention overcomes the disadvantages of the prior art by providing a system and method of manufacturing a customized radiolucent and MR compatible retractor for use in image guided trans-oral robotic surgery. An image of an oral cavity and airway of a patient is acquired and the location of a tumor is identified. A 3D model representing associated anatomy is made and a customized retractor is then designed based on the 3D model and the location of the tumor. The customized retractor is then 3D-printed based upon the design. Illustratively, a maxillary blade supported by a body is 3D-printed, and enables one or more surgical instruments to pass therethrough. The body/maxillary blade is movable relative to a tongue blade to allow a retraction operation on the patient. The tongue blade can be constructed to be movable transversely to the body and/or the maxillary blade can be constructed from a Nylon material and the tongue blade is constructed from a carbon fiber composite material. The tongue blade can include a grooved rack can slidably engage a tongue blade base having a cam for locking and unlocking a slidable adjustment position of the tongue blade relative to the body. The retractor can further include and arm assembly adapted to mount, at a proximal end of the retractor, to a support stand, the arm being adjustable in length of extension to thereby move the tongue blade and maxillary blade. The arm assembly can include, at the proximal end, a support that allows for an angle of the arm assembly to be adjusted using a worm gear. The tongue blade base adjustably moves along the arm assembly so as to vary a distance between the tongue blade and the maxillary blade. The tongue blade base can include a set screw, which can be constructed from a polymer or other radiolucent/MR-compatible material, to fix a position thereof relative to the arm assembly. An overall length of the arm assembly can be adjusted by moving a telescoping portion of the arm assembly relative to a sleeve and fixing the portion with respect to the sleeve in a desired position.

In another illustrative embodiment, a system and method of performing image-guided trans-oral robotic surgery is provided. A radiolucent and MR compatible retractor adapted to open an oral cavity is inserted. A support stand/rig is adjusted to hold the radiolucent and MR compatible retractor in a fixed position and orientation relative to the support stand/rig. Once adjusted and fixed, trans-oral robotic surgery is performed, and/or imaging is performed using x-rays, CT, or MRI during the trans-oral robotic surgery so that the surgery can be informed by the imaging.

In another illustrative embodiment, a system having for image guided trans-oral robotic surgery is provided. A customized radiolucent and MR compatible retractor is adapted to access the oropharynx, and is constructed and arranged based upon an image of an oral cavity and airway in which a location of a tumor therein is identified, to generate a 3D model representing associated anatomy. The retractor is 3D printed based upon the 3D model. The retractor includes a maxillary blade supported by a body that enables one or more surgical instruments to pass therethrough, and is movable relative to a tongue blade to allow a retraction operation on the patient. Illustratively, the system can include a robotic surgical arrangement with which the retractor operates. The retractor can include an adjustable length and angle arm assembly, which can be adapted to engage, at a proximal end thereof, a support rig that maintains the retractor in a fixed position and orientation with respect to a patient. The maxillary blade can be constructed from a Nylon material and the tongue blade is constructed from a carbon fiber composite material. The tongue blade can include a grooved rack and can slidably engage a tongue blade base having a cam for locking and unlocking a slidable adjustment position of the tongue blade relative to the body. The retractor can include an arm assembly adapted to mount, at a proximal end of the retractor, to a support stand. The arm can be adjustable in length of extension to thereby move the tongue blade and maxillary blade. The arm assembly can include, at the proximal end, a support that allows for an angle of the arm assembly to be adjusted using a worm gear. The tongue blade base can adjustably move along the arm assembly so as to vary a distance between the tongue blade and the maxillary blade. Additionally, the tongue blade base can include a set screw (and associated knob) to fix a position thereof relative to the arm assembly.

BRIEF DESCRIPTION OF THE DRAWINGS

The invention description below refers to the accompanying drawings, of which:

FIG. 9B is a perspective view of a tongue blade, according to an illustrative embodiment;

FIG. 9C is a cross section of the tongue blade taken along cross section line 9C-9C, according to the illustrative embodiment;

DETAILED DESCRIPTION

I. Improved System and Method for Laryngoscopy

By way of further background, surgeries performed through the oral cavity, such as surgeries on the mouth, neck, or throat, often benefit from the use of a retractor to open the mouth and provide a working space for a surgeon to operate. Imaging-compatible retractors and support rigs, such as the MR and CT imaging compatible devices described in U.S. Pat. No. 10,582,836, entitled SYSTEM AND METHOD OF LARYNGOSCOPY SURGERY AND IMAGING, issued Mar. 10, 2020, the entire disclosure of which is incorporated herein by reference, can allow a surgeon to simultaneously perform surgery that requires a retractor while also using intraoperative imaging. Various embodiments of imaging-compatible retractors can be used on different patients and in different types of surgery, and various retractors can be custom-designed and custom-created for different patients and different surgical needs.

Individual retractors can be adjustable and/or customized, and various retractors can be supported using an imaging-compatible support rig that can be adjustable and/or customized, and an imaging compatible support frame. A single supporting foundation can be used across different patients, different surgeries, and different retractors.

Figure 1A:
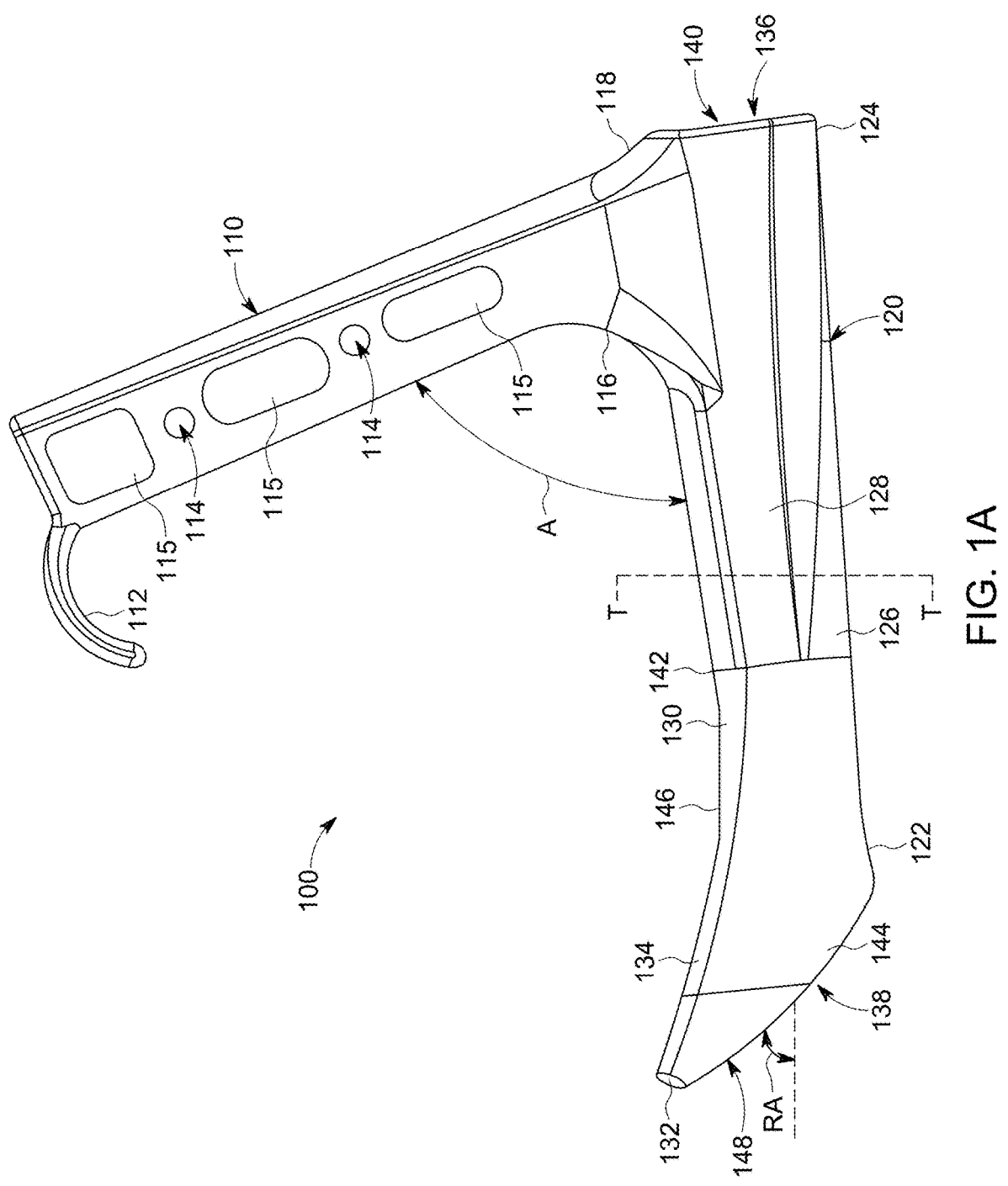
FIG. 1A is a side view of a radiolucent and MR-compatible laryngoscope, according to an embodiment.

FIG. 1A is a side view of a laryngoscope, according to an embodiment. A laryngoscope 100 can be used to provide a user with a view of various structures inside of a patient's throat, including the glottis, vocal cords, larynx, and others. As used herein, a user can be a doctor, a surgeon, a radiologist, an anesthesiologist or other medical provider, and/or a hospital, a medical school, or other medical service providing organization. In an embodiment, a laryngoscope 100 can have a handle 110 and an insertion member 120. The handle 110 and the insertion member 120 can be at an angle that can be in a range of approximately 60-80 degrees. As shown in FIG. 1A, the insertion member and handle are at an angle A of approximately 72 degrees. The insertion member 120 can have a distal end 122 that is the end away from the handle that can be inserted into the mouth of a patient and the insertion member can have a proximal end 124 that is nearest to the handle.

The handle can have a hook 112, at least one securing hole 114, at least one weight-reducing hole 115, a distal fillet 116, and a proximal fillet 118. The at least one securing hole 114 can be used in securing the laryngoscope to a rig, explained more fully below. The at least one weight-reducing hole 115 can reduce the weight of the laryngoscope, while also reducing the cost of the material used in the laryngoscope and reducing the time required to produce the laryngoscope. A distal fillet 116 can be a curved member between the handle 110 and the insertion member 120. A polymer laryngoscope may have reduced material strength compared to a traditional metal laryngoscope. The distal fillet 116 can add strength to the laryngoscope by making the union between the handle 110 and the insertion member 120 free of corners or sharp angles, and by adding additional material between the handle 110 and the insertion member 120. A proximal fillet 118 can be a curved member between the handle 110 and the insertion member 120. The distal fillet 118 can add strength to the laryngoscope by making the union between the handle 110 and the insertion member 120 free of corners or sharp angles, and by adding additional material between the handle 110 and the insertion member 120. The distal fillet 116 and proximal fillet 118 can provide increased strength to the laryngoscope 100 at the union between the handle 110 and insertion member 120, so that the laryngoscope can withstand the forces imparted by the patient, while allowing the laryngoscope 100 to be made from a lightweight, non-metallic material that can be radiolucent and MR compatible.

In various embodiments, an insertion member 120 can include a tube 126. A tube 126 can be formed by at least one sidewall 128. The at least one sidewall 128 can be entirely enclosing so that when the insertion member 120 is viewed in cross-section along line T-T, the insertion member 120 can be in the shape of a circle, or the letter "D", or other closed conformations. The at least one sidewall 128 can be partially enclosing, so that when the insertion member 120 is viewed in cross section along line T-T, the at insertion member 120 can be in the shape of the letter "C", or an upside-down letter "L", or other open conformations. The insertion member 120 can have a blade 130. The blade 130 can have a leading edge 132. The leading edge 132 can be the most distal portion of the insertion member 120. A blade 130 can have a ramp 134 in a distal area of the blade. The ramp 134 can be an inclined area of the blade 130. The ramp 134 can be curved and/or angled upwards. The insertion member 120 can have a rib 146 that can extend along an upper portion of the insertion member. The rib 146 can be a region of thicker material that can add strength to the insertion member 120, so that the laryngoscope can withstand the forces imparted by the patient, while allowing the laryngoscope 100 to be made from a lightweight, non-metallic material that can be radiolucent. The rib 146 can be along the exterior of the insertion member 120, so that the increased material thickness does not obstruct the user's view through the laryngoscope. The rib 146 can be the region of the insertion member having the thickest material. The rib 146 can extend at least partially between the distal fillet 116 and the ramp 134. The rib 146 can extend entirely between the distal fillet 116 and the ramp 134.

The insertion member can have a neck 142 that can be an area of the insertion member between the distal end 122 and proximal end 124. The neck can be narrower than the distal 122 end and/or the proximal end 124. The insertion member 120 can have a bell 144 at the distal end 122. The bell 144 can be a taller and/or wider portion of the insertion member 120, so that the distal end can be larger than the neck 142. The ramp 134 can form part of the bell 144, so that the bell 144 can be taller than the neck 142. The bell 144 can have a rim 148 that can be the distal edge of the bell 144. The leading edge 132 can be raised up and away from the neck 142, and the leading edge 132 can form a portion of the rim 148. The rim 148 can be approximately two-dimensional and can be in a plane that is at an angle to the central lumen 136. The shape of the rim 148 can be approximately defined as a cylindric section that can be an intersection of a plane with a cylinder, with the plane at an angle approximately 45-65 degrees from the central axis of the cylinder. The rim 148 can be at a rim angle RA of approximately 45-65 degrees from the central axis of the insertion member. The rim 148 can be approximately the shape of a cylindric section having a portion of the cylindric section removed at the leading edge 132, so that the rim 148 can have a flattened area at the most distal portion of the insertion member where the ramp 134 meets the bell 144. When viewed from the side, the rim 148 can be in the shape of a portion of a parabola, with the angle of the rim increasing from the bottom of the rim to the leading edge. A rim with a parabolic shape can have an angle of approximately 20 degrees near the bottom of the rim, and the angle of the rim can approach approximately 65 degrees near the leading edge 132. The rim 148 can be continuously curved from one side of the leading edge 132 to the other side of the leading edge 132. The shape of the rim 148 can provide increased strength to the distal end of the insertion member, so that the insertion member can withstand the forces imparted by the patient's tough and throat, while allowing the insertion member to be made from a lightweight, non-metallic material that can be radiolucent.

The blade 130 can form the top of the tube 120. The tube 120 can have a central lumen 136. Central lumen 136 can be a passage through the insertion member 120. The central lumen 136 can have a distal orifice 138 that can be an opening at the distal end 122 of the insertion member 120. The central lumen 136 can have a proximal orifice 140 that can be an opening at the proximal end 124 of the insertion member 120. In alternate embodiments, the insertion member 120 can have a blade 130 without a tube 120. In alternate embodiments, the insertion member 120 can have a blade 130 without a sidewall 128.

Figure 1B:
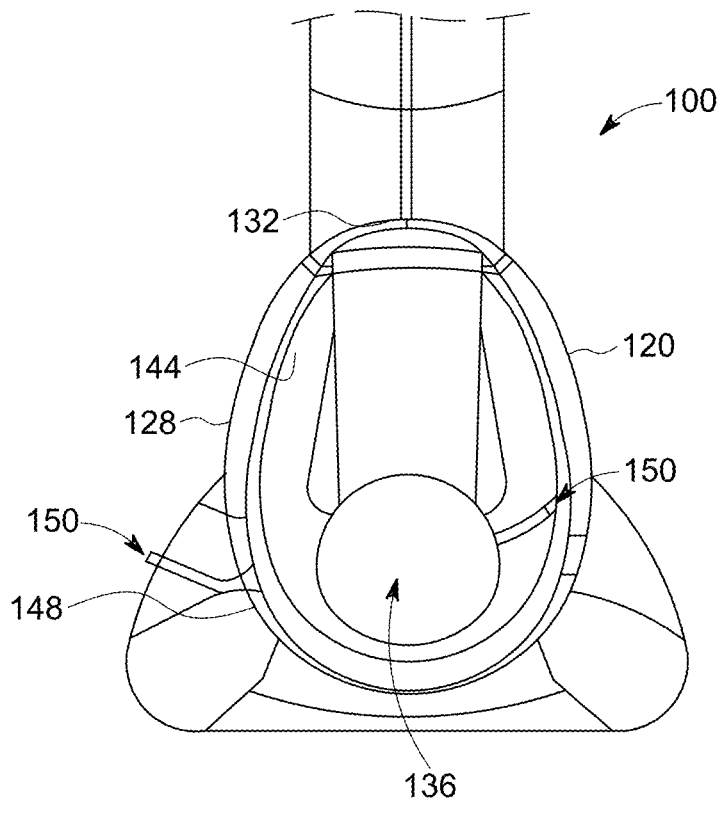
FIG. 1B is an end view of a distal end of an insertion member of a laryngoscope, according to an embodiment.

FIG. 1B is an end view of the distal end an insertion member of a laryngoscope, according to an embodiment. In various embodiments, an insertion member can include at least one channel 150 adapted for introducing an additional instrument, such as a fiber optic camera, a suction tube or channel, tissue graspers and retractors, a laser fiber, or other tool or device used by a surgeon. The at least one channel 150 can extend at least partially from a distal end 122 to a proximal end 124 of the insertion member. The at least one channel can extend fully from a distal end 122 to a proximal end 124 of the insertion member. The at least one channel can be an enclosed conduit, a partially enclosed trough, a series of guides, or other means for holding an instrument. The at least one channel can be along an interior of a sidewall 128, along exterior of a sidewall 128, and/or housed within the sidewall 128. The rim 148 at the distal end of the bell 144 can be approximately ovate, or egg-shaped, when viewed from the distal end 122.

Figure 1C:
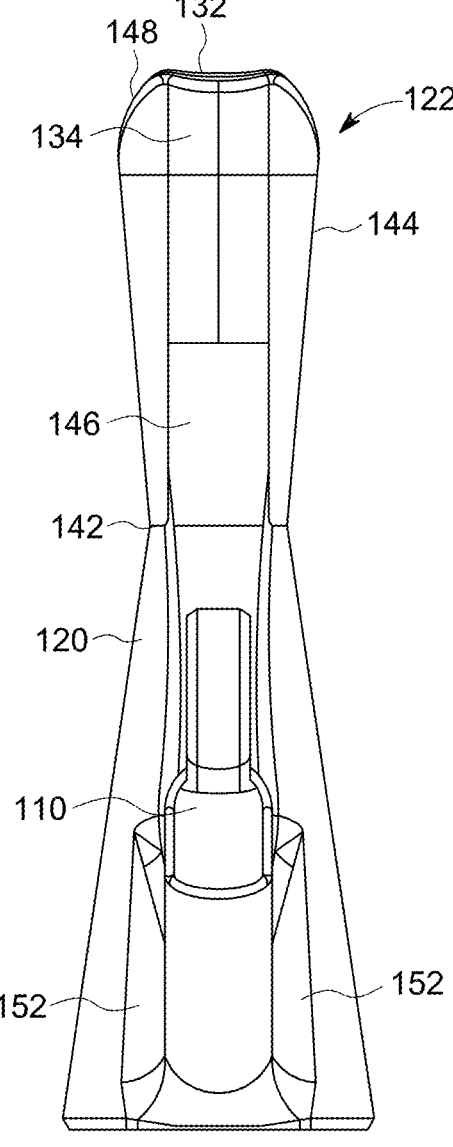
FIG. 1C is a top view of a laryngoscope, according to an embodiment.

FIG. 1C is a top view of a laryngoscope, according to an embodiment. The neck 142 of the insertion member 120 can be the narrowest portion of the insertion member 120, and the bell 144 can extend outwards from the neck 142, so that the insertion member becomes wider towards the distal end 122. The bell 144 can extend between the neck 142 and the rim 148. The rim 148 can be approximately in the shape of a cylindric section or tear-drop shaped, with a flattened area where the ramp 134 meets the rim 148. The laryngoscope 100 can have side filets 152 where the handle 110 meets the insertion member 120. The side fillets 152 can provide increased strength to the laryngoscope 100 at the union between the handle 110 and insertion member 120, so that the laryngoscope can withstand the forces imparted by the patient, while allowing the laryngoscope 100 to be made from a lightweight, non-metallic material that can be radiolucent Various retractors including laryngoscope 100 can be manufactured using a 3D printer, such as the Objet Eden250 manufactured by Stratasys, by way of non-limiting example of a variety of possible devices and modalities. The laryngoscope 100 can be manufactured from non-metallic materials that can be radiolucent, such as polymers including poly(methyl methacrylate) (acrylic), or polyethylene, polycarbonate, polyamide (nylon), and/or polyvinyl chloride. By manufacturing the laryngoscope 100 from non-metallic materials, the laryngoscope 100 can be used within MRI scanners, CT scanners, PET scanners, X-rays, and other imaging devices, and can be used with electromagnetic instrument tracking. In some embodiments designed for use with MR imaging, ceramic material can also be used.

Figure 2A:
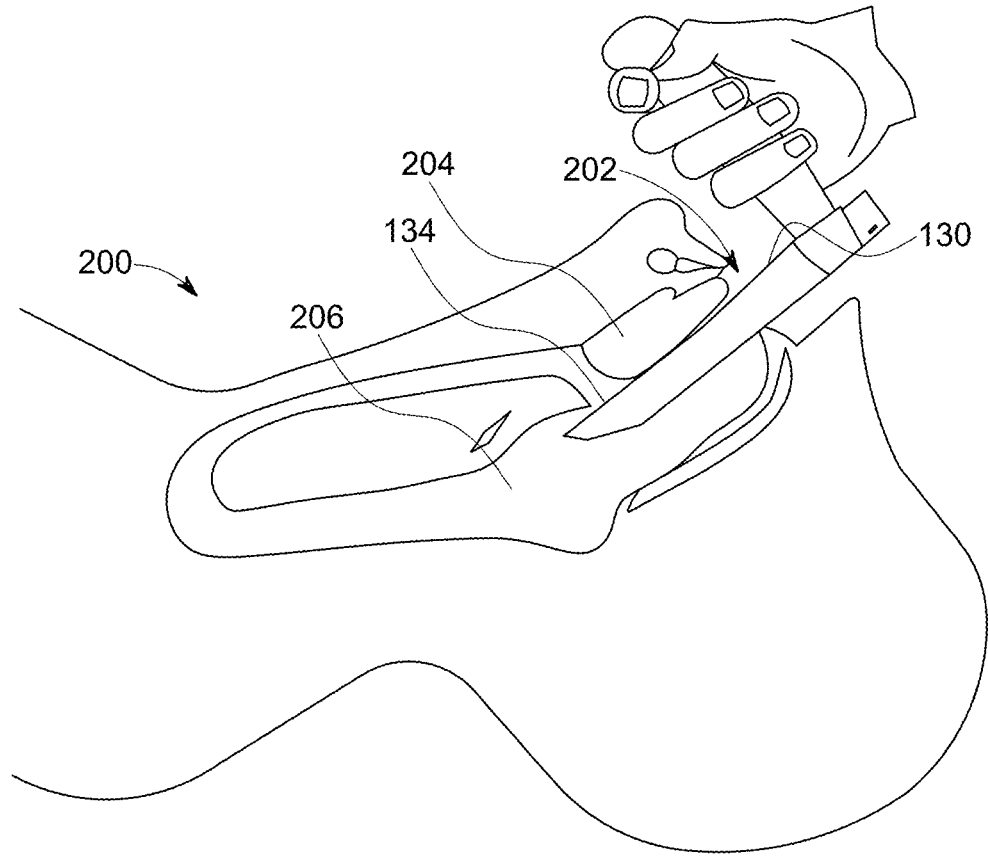
FIG. 2A is a diagrammatic view of a patient with a laryngoscope being inserted into the patient's mouth by a medical provider, according to an embodiment.
Figure 2B:
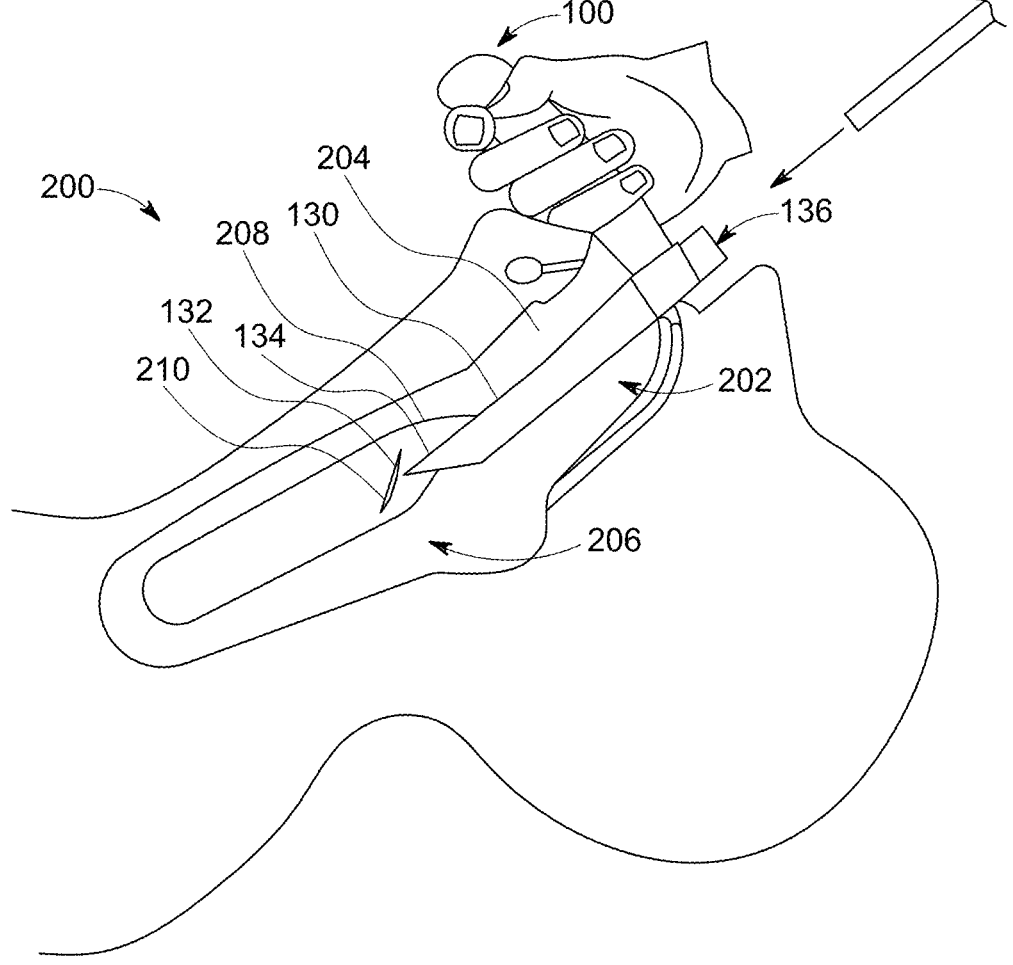
FIG. 2B is a diagrammatic view of a patient with a laryngoscope being inserted into the patient's throat by a medical provider, according to an embodiment.

FIG. 2A is a diagrammatic view of a patient with a laryngoscope being inserted into the patient's mouth by a user, such as a medical provider, according to an embodiment. A patient 200 can be positioned on his back, so that a medical provider can insert a laryngoscope 100. The medical provider can insert the laryngoscope 100 into the patient's mouth 202, and can use the blade 130 to move the tongue 204 up and/or off to one side so that the tongue can be out of the way, thereby providing an unobstructed view of the top of the patient's throat 206. The curve of the ramp 134 can be inserted down the patient's throat 206. FIG. 2B is a diagrammatic view of a patient with a laryngoscope being inserted into the patient's throat by a medical provider, according to the embodiment. The leading edge 132 and/or the ramp 134 can be used to lift the epiglottis 208 so that the medical provider can insert the laryngoscope 100 past the epiglottis 208 and down the throat 206. The patient can have his head tilted back, so that the medical provider can insert the laryngoscope 100 through the mouth 202 and into the throat 206. The laryngoscope can provide an unobstructed path between the outside of the patient and the anatomical structures in the patient's throat, such as the larynx 210, voice box, glottis, and or/other structures. With the laryngoscope inserted into the patient's throat, the medical provider can have a clear view of the larynx 210, voice box, glottis, and/or other structures through the central lumen 136. The medical provider can direct a laser or other surgical tool through the central lumen 136. The medical provider can insert an intubation tube into the patient through the central lumen 136.

A laryngoscope can be used by a medical provider who can perform surgery on the patient, such as surgery directed to a tumor in the throat or other anatomical structure. A patient can be sedated while the laryngoscope 100 is inserted into the throat 206 so that the user can see into the throat and can direct a laser or other surgical tool into the throat 206. When the patient is sedated with his head tilted back, and with a laryngoscope in the throat 206, the patient's anatomical structures such as the larynx and other structures of the throat, as well as tumors or other areas to be targeted for surgery, can shift positions. Images taken of the anatomical structures, including possible tumors, while the patient is awake and/or in a more common position may not accurately reflect the locations of anatomical structures and tumors while the patient is sedated, with the head tilted back and the laryngoscope inserted in the throat. The laryngoscope 100 that is made of non-metallic materials can be used in an MRI scanner, CT scanner, or other imaging devices. A user can use the imager to obtain images of the patient's anatomical structures while the laryngoscope is inserted, so that the user can accurately perform surgery on the correct areas, such as the area of a tumor.

Figure 3A:
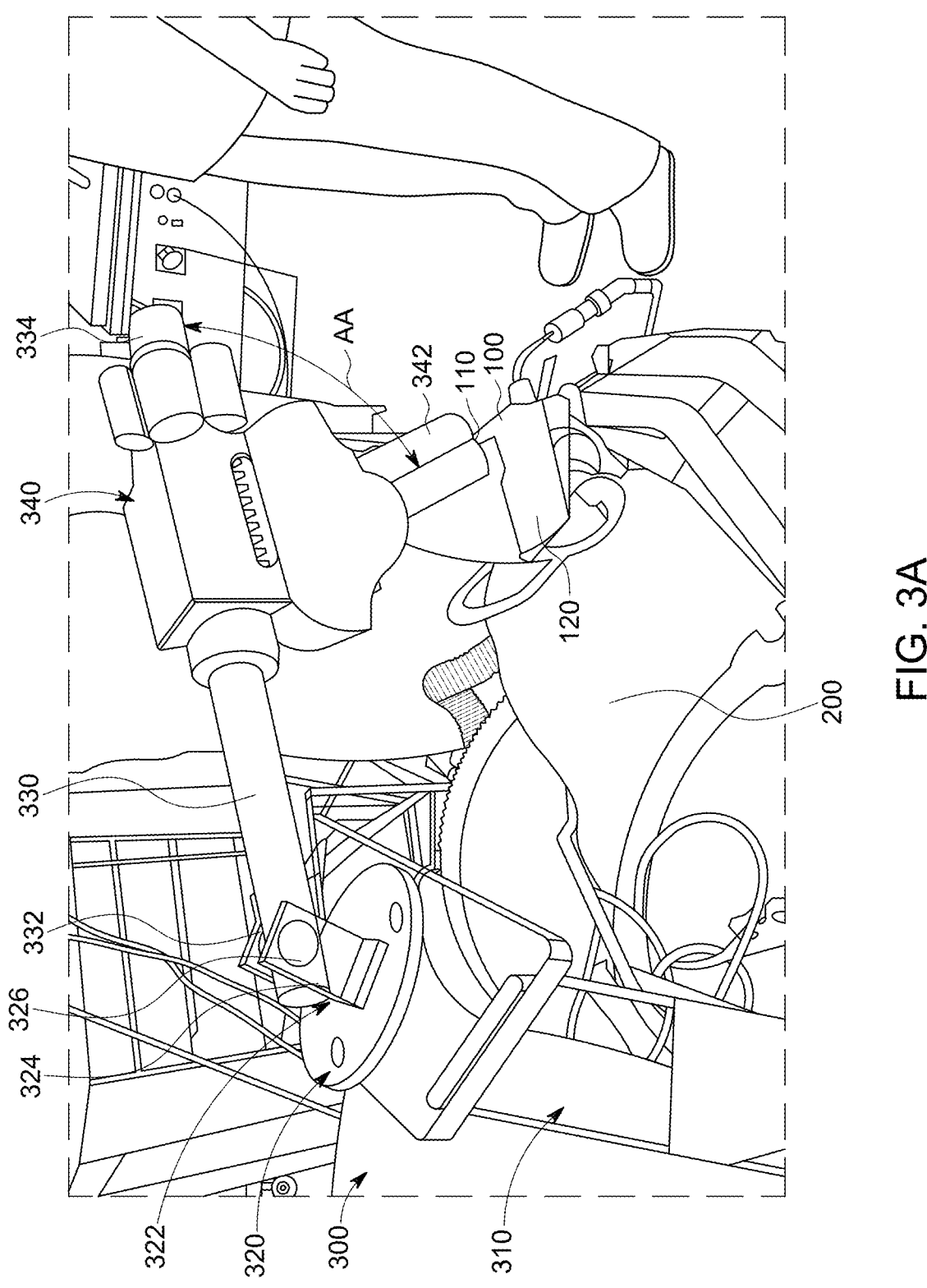
FIG. 3A is a perspective view of a patient with an inserted laryngoscope, with the laryngoscope held in a support rig, according to an embodiment.

FIG. 3A is a perspective view of a patient with an inserted laryngoscope, with the laryngoscope held in a support rig, according to an embodiment. A support rig 300 can hold a laryngoscope 100 in a selectable fixed position and orientation, without the user needing to hold the laryngoscope 100. The support rig 300 can maintain the laryngoscope 100 in a fixed position and orientation without being impacted by breathing or other movement of the patient 200. A support rig 300 can have a wrist 320, an arm 330, and an elbow assembly 340. A support rig can include, or be attached to, a support frame 310. A frame 310 can provide a base for the support rig 300, so that the laryngoscope 100 can be supported above the patient and not be affected by breathing or other movements of the patient 200.

Figure 3B:
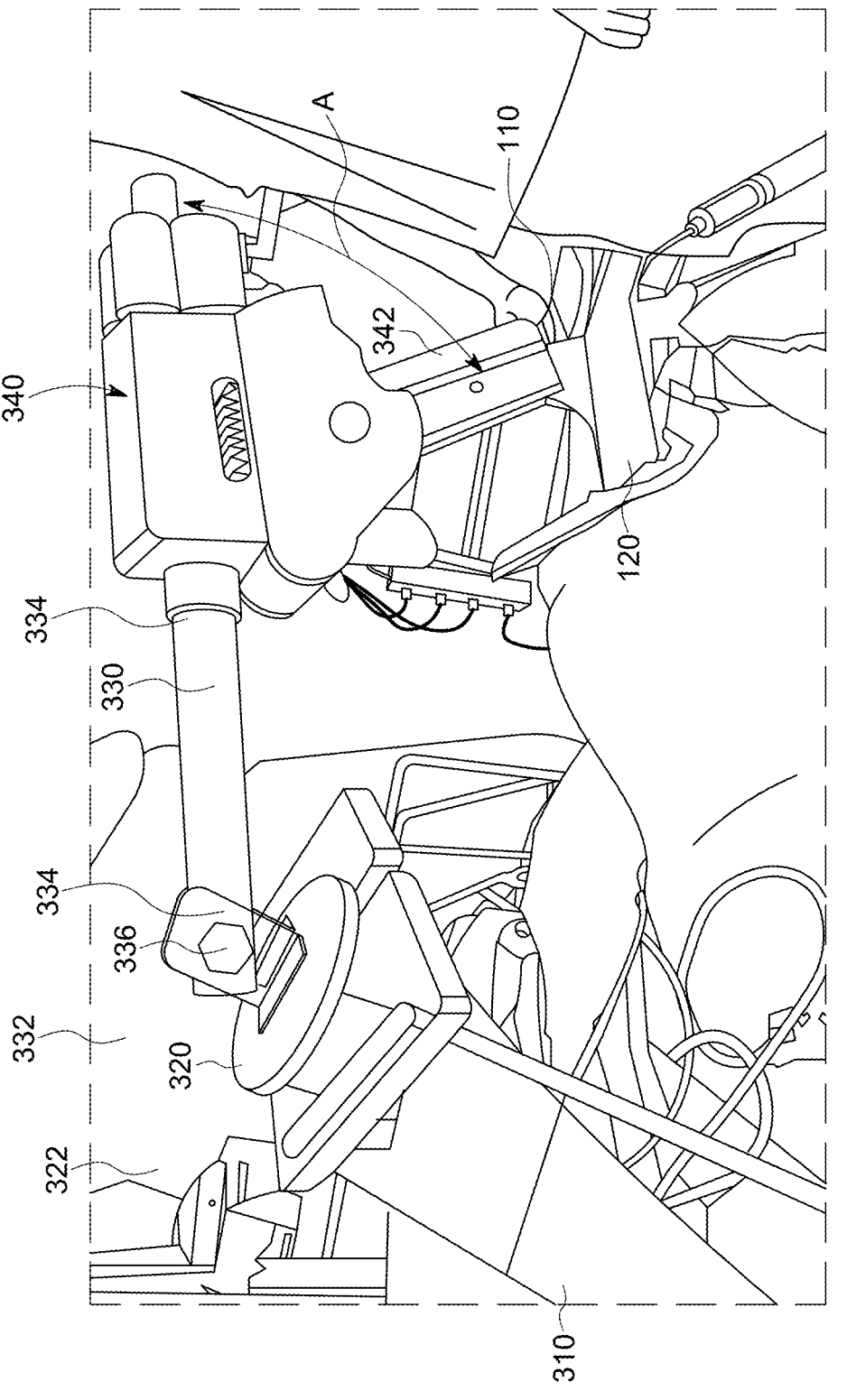
FIG. 3B is a side view of a patient with an inserted laryngoscope, with the laryngoscope held in a support rig, according to the embodiment.

FIG. 3B is a side view of a patient with an inserted laryngoscope, with the laryngoscope held in a support rig, according to the embodiment. A wrist 320 can be mounted to the frame 310. In various embodiments the wrist 320 can be held in a fixed position relative to the frame 310, or the wrist 320 can swivel relative to the frame 310. In various embodiments the wrist 320 can swivel freely relative to the frame 310, or the user can swivel the wrist 320 into a selected orientation and can fix the wrist 320 into the selected orientation relative to the frame 310.

The arm 330 can be hingedly mounted to the wrist 320. The arm 330 can have a wrist area 332 and an elbow area 334, and the arm 330 can be hingedly mounted to the wrist 320 at the wrist area 332. The wrist 320 can have a hinge 322. The hinge can have at least one arm holder 324 and a pin 326. The at least one arm holder 324 can extend from the wrist 320 and can have at least one hinge hole through the arm holder 324. The arm 330 can have a hinge hole at the wrist area 332. A pin 326 can pass through the arm holder 324 and the wrist area 332 of the arm. The pin 326 can be a bolt or other connector that can pass through the hinge hole in the arm 330 and the hinge hole in the arm holder 324, so that the arm 330 can pivot on the hinge 322. In alternate embodiments, various different hinges can be used, and should be obvious to one of skill in the art. A user can adjust the position and orientation of the arm 330 relative to the frame 310 by pivoting the arm 330 on the hinge 322. A user can adjust the position and orientation of the arm 330 relative to the frame 310 by swiveling the wrist 320.

An elbow assembly 340 can be connected to the arm 330. An elbow assembly 340 can have a holder 342. The holder 342 can hold the handle 110 of the laryngoscope 100, so that the handle 110 can be fixed to the holder 342. The elbow assembly 340 can allow a user to adjust the elbow angle HA, which is the angle of the handle 110 relative to the arm 330. The elbow assembly 340 can allow the user to set the angle of the handle 110 relative to the arm 330 in a fixed orientation, explained more fully below.

The angle or orientation of the insertion member 120 can be changed by adjusting the elbow angle HA of the handle 110 to the arm 330 because the rigid laryngoscope 110 can have the insertion member 120 and the handle 110 at a fixed angle relative to each other. When a user adjusts the elbow angle, the angle and orientation of the entire laryngoscope 100, including the insertion member 120 can be adjusted. The distal end of the insertion member 120 can remain inserted in the throat while the user adjusts the angle and orientation of the insertion member 120 by adjusting the elbow angle. When the insertion member 120 is inserted in the throat and the elbow angle is adjusted, the arm 330 can pivot on the hinge 322.

A user can insert the insertion member 120 into a patient, and the user can affix the handle 110 to the holder 342. The user can then adjust the elbow angle to adjust the orientation of the insertion member 120. By adjusting the orientation of the insertion member 120, the user can move the insertion member 120 into a desired position to see a particular anatomical structure within the patient's throat. Adjusting the orientation of the insertion member can allow a user to position the lumen at a preferred angle for directing a laser or other surgical instrument through the lumen towards targeted anatomical structure. In an embodiment, a metallic insert, such as a metallic tube, can be removably placed within the central lumen 136 of the insertion member 120 to shield the laryngoscope form the laser. A user can insert the metallic insert for use with the laser, and the user can remove the metallic insert prior to imaging.

Figure 3C:
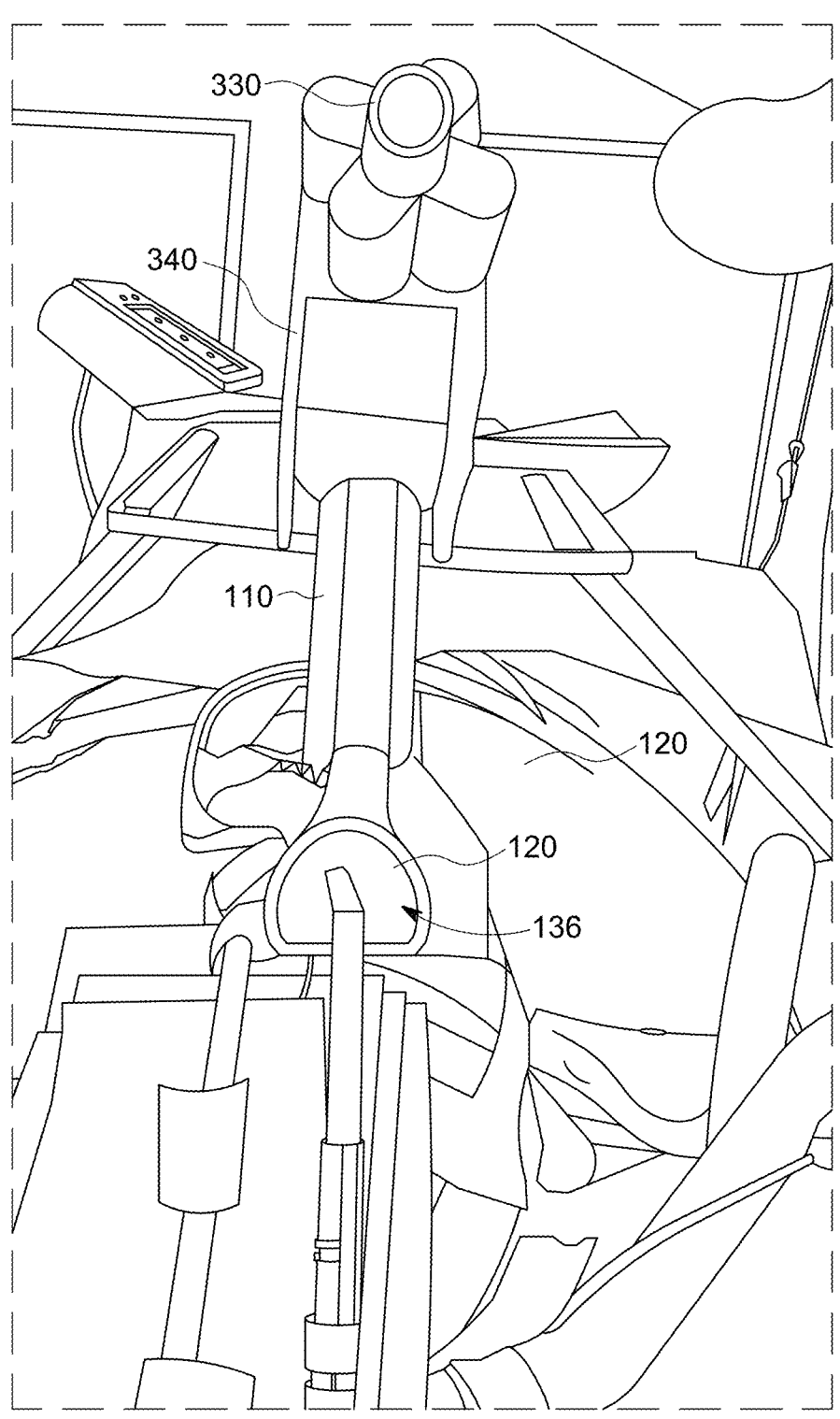
FIG. 3C is an end view of a patient with an inserted laryngoscope, with the laryngoscope held in a support rig, according to the embodiment.

FIG. 3C is an end view of a patient with an inserted laryngoscope, with the laryngoscope held in a support rig, according to an embodiment. The laryngoscope is shown inserted into the throat and holding the tongue to the side. A user can direct a light through the lumen 136 and can look through the lumen to see the anatomical structures such as the larynx. A user can direct a laser through the lumen towards anatomical structures such as the larynx. A user can adjust the angle of the insertion member 120 and lumen 136 so that the user can have a desired view or a desired angle for a laser or other surgical instrument. The user is able to fix the insertion member 120 at a desired angle that will not be changed by the breathing or other movement of the patient 200.

Figure 4A:
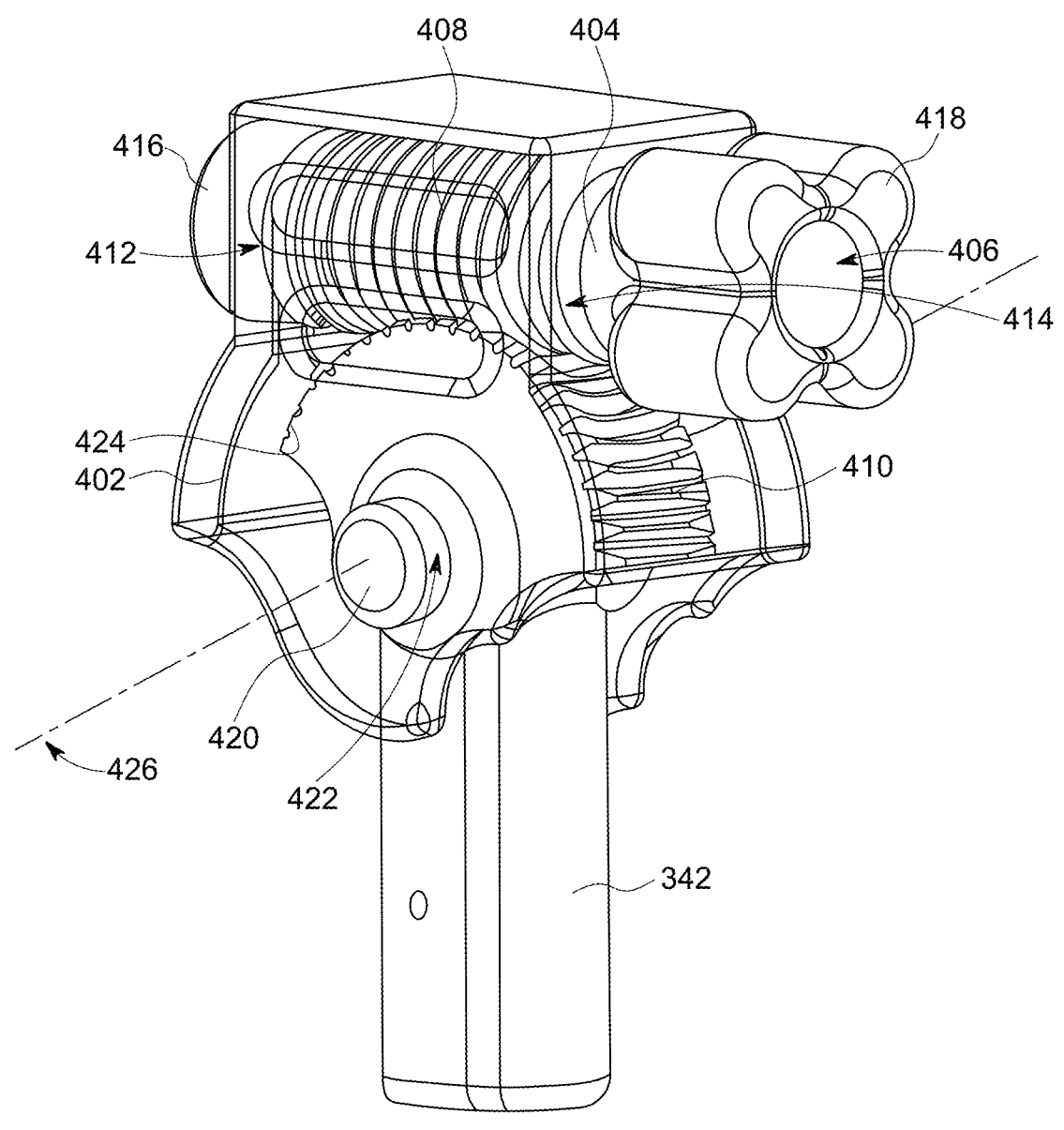
FIG. 4A is a perspective view of an elbow assembly, according to an embodiment.

FIG. 4A is a perspective view of an elbow assembly, according to an embodiment. Various elbow assemblies can be used to connect various retractors to the arm of the support rig. An elbow assembly can allow a user to adjust the orientation of a retractor such as a laryngoscope that is inserted into the throat of a patient. It should be clear that the elbow assembly can be used with a laryngoscope and/or various other retractors or other surgical instruments without departing from the scope of the present disclosure, and that various elbow assemblies are possible. A user can fine tune the angle of the laryngoscope and fix the angle so that it remains in the selected position. An elbow assembly can have an outer shell 402, an adjuster 404, and a holder 342. The elbow assembly 340 can have a bore 406. The bore 406 can be an opening in the elbow assembly 340 adapted to engage with the arm. The bore 406 can be through the adjuster 404. The arm can be inserted through the bore 406, and the adjuster 404 can rotate on the arm 330. In alternate embodiments, an elbow assembly can have a mounting platform, spring-loaded pins and holes, or various other means to attach the elbow assembly to the mounting platform. In alternate embodiments, the elbow assembly can clip onto the arm or otherwise be attached to the arm in various ways that will be apparent to one skilled in the art.

The elbow assembly 340 can have a worm gear 408 and a rack 410. The worm gear 408 can be on the adjuster 404 and the rack 410 can be on the holder 342. The outer shell 402 can hold the worm gear 408 in engagement with the rack 410. The outer shell can have a distal opening 412 and a proximal opening 414. The adjuster can have a distal extension 416 and a knob 418. The distal extension 416 can protrude through the distal opening 412, and the knob 418 can protrude through the proximal opening 414, so that the adjuster 404 can be held within the outer shell 402, and can rotate in place within the outer shell 402. The elbow assembly can have at least one axle 420. The at least one axle 420 can be a part of the holder 342 that extends from the holder 342 and can be engaged by the outer shell 402, so that the holder can pivot relative to the outer shell 402 on the axle 420. The at least one axle 420 can extend through at least one side opening 422 through the outer shell 402. The at least one axle 420 can be an independent axle that can extend through the holder 342 and be engaged by the outer shell 402, so that the holder 342 can pivot relative to the outer shell 402 on the axle 420.

The holder 342 can have an upper arc 424 that can be a segment of a cylinder with a central axis 426 that passes through the axle 420. The rack 410 can be arranged along the circumference of the upper arc 424, so that teeth of the rack 410 can be equidistant from the central axis that passes through the axle 420. A user can turn the knob 418, which can cause the adjuster 404 to rotate within the outer shell 402 and turn the worm gear 408. The turning worm gear 408 can cause the rack 410 to rotate around the central axis, with the holder turning on the at least one axle 420. When the user turns the knob 418, causing the holder 342 to turn on the at least one axle 420, the angle between the holder 342 and the arm 330 (not shown) can be selectively adjusted.

Figure 4B:
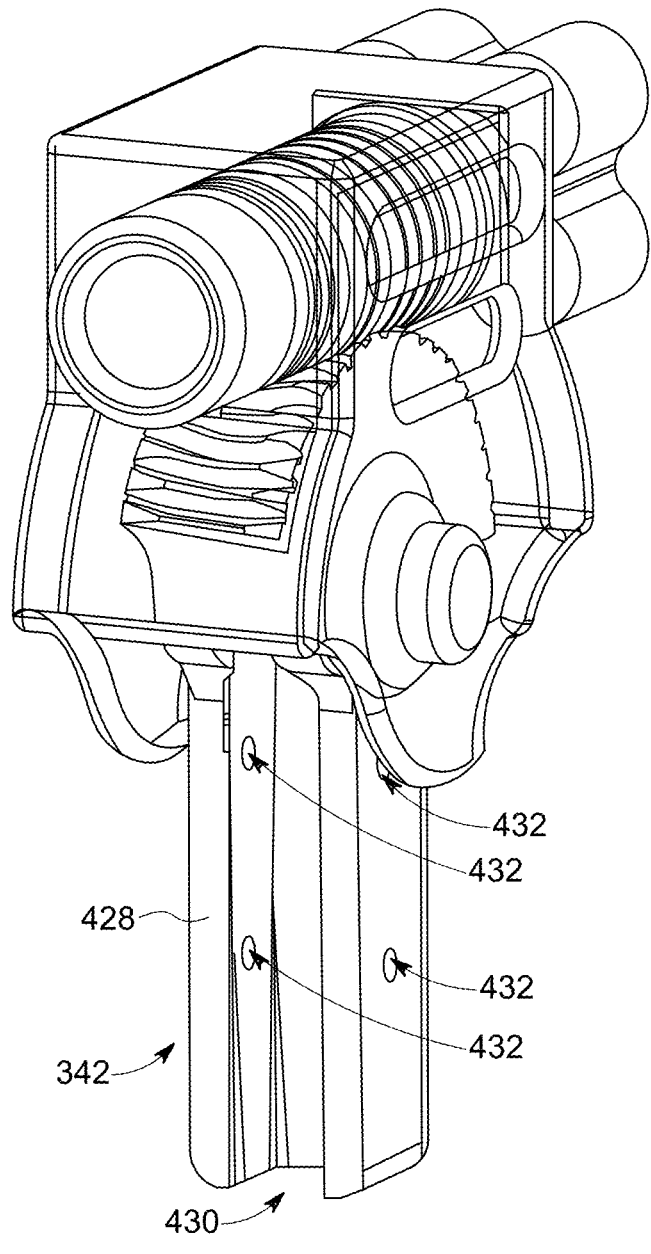
FIG. 4B is a perspective view of an elbow assembly from a different perspective, according to the embodiment

FIG. 4B is a perspective view of an elbow assembly from a different perspective, according to the embodiment. The holder 342 can have an engagement arm 428 adapted to engage with the handle. The engagement arm 428 can have an engagement area 430. The engagement area 430 can be a channel in the engagement arm 428. The channel can be sized and shaped to be adapted for the handle 110 to be placed within the channel. The engagement arm 428 can have at least one securing hole 432. The at least one securing hole 432 can be aligned with at least one securing hole 114 of the handle 110, so that a bolt, pin, or other securing means can be passed through the securing hole 432 of the holder and the securing hole 114 of the handle, thereby securing the handle within the engagement area 430.

Figure 4C:
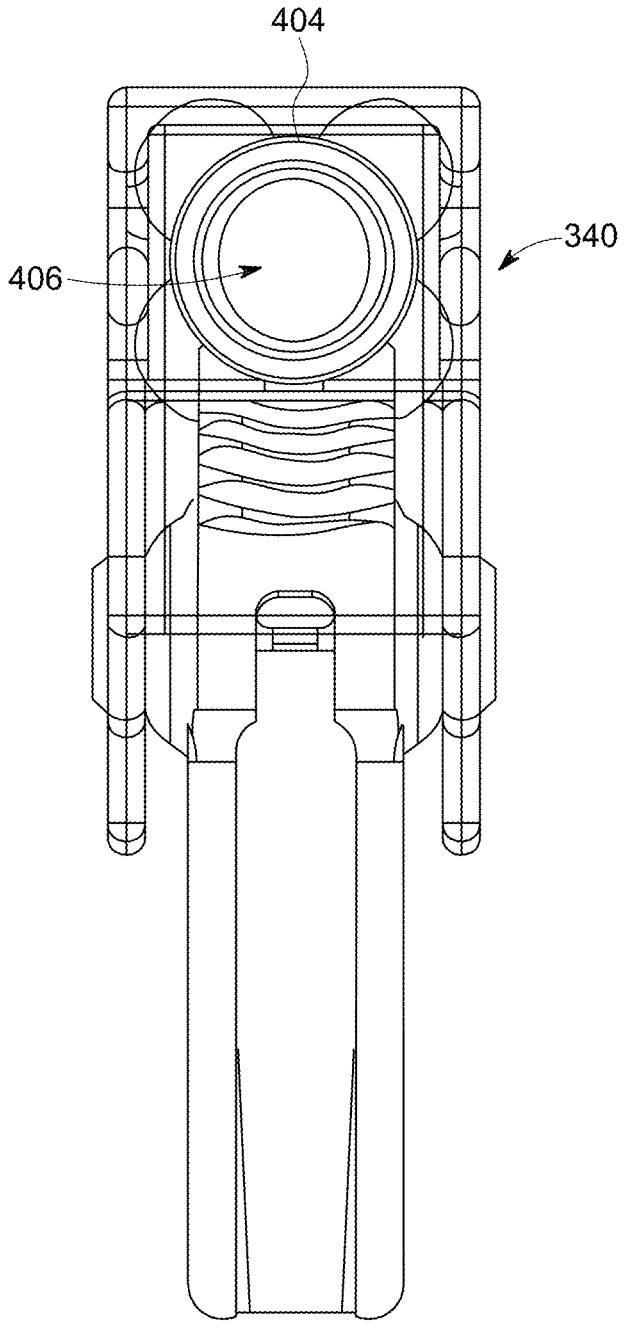
FIG. 4C is an end view of an elbow assembly, according to the embodiment.

FIG. 4C is an end view of an elbow assembly, according to the embodiment. The bore 406 can be an opening in the elbow assembly 340. The bore 406 can have a shape that is adapted to the shape of the elbow end 334 of the arm 330, so that arm 330 can be inserted into the bore 406. In the embodiment, the arm 330 can be cylindrical, and the bore 406 can be cylindrical and can be through the adjuster 404, so that the adjuster 404 can rotate around the arm 330.

Figure 4D:
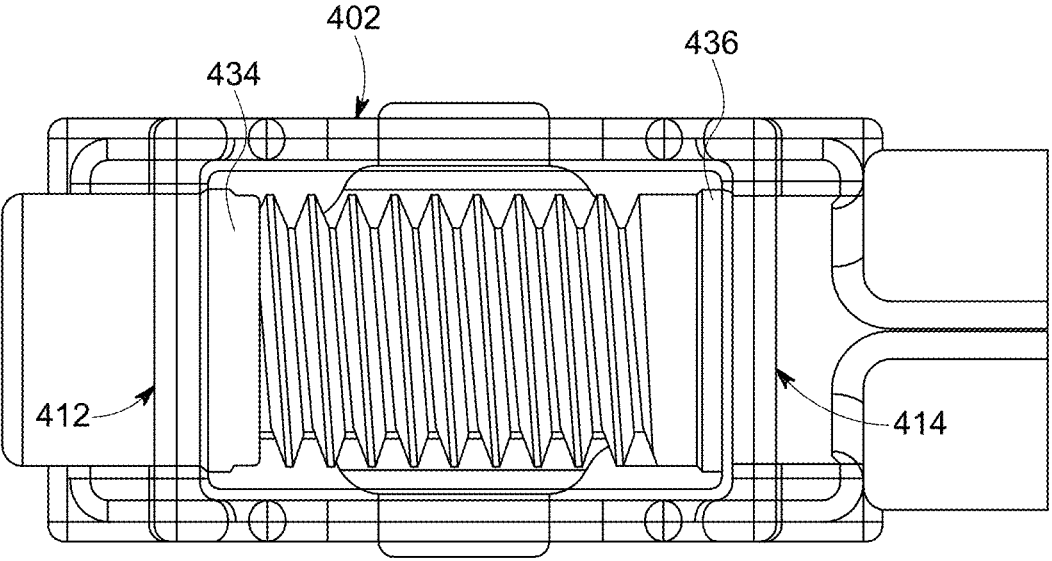
FIG. 4D is a top view of an elbow assembly, according to the embodiment.

FIG. 4D is a top view of an elbow assembly, according to the embodiment. The adjuster 404 can have a distal ridge 434 and a proximal ridge 436. The distal ridge 434 can be larger than the distal opening 412 of the outer shell 402, so that the distal ridge 434 does not pass through the distal opening 412. The proximal ridge 436 can be larger than the proximal opening 414 of the outer shell 402, so that the proximal ridge 436 does not pass through the proximal opening 414. The distal ridge 434 and proximal ridge 436 can hold the adjuster 404 within the outer shell 402.

In an embodiment, an elbow assembly such as the elbow assembly 140 can be printed using a 3D printer such as the Objet Eden 250 manufactured by Stratasys. 3D printing the elbow assembly can allow all of the parts to be printed together at the same time, so that the finished elbow assembly is already assembled when the printing is finished. In this way, an adjuster 404, which can include a proximal ridge 436 and/or a distal ridge 434, can be printed within the outer shell 402 in the same printing session as the outer shell 402 is printed, so that there is no need to assemble the various components of the elbow assembly within the outer shell

402 after the components are printed. After printing of the outer shell 402 has begun, but before printing of the outer shell has been completed, other components of the elbow assembly 340 can be printed within the uncompleted outer shell 402, so that the finished printed product can be a fully assembled elbow assembly.

Figure 5A:
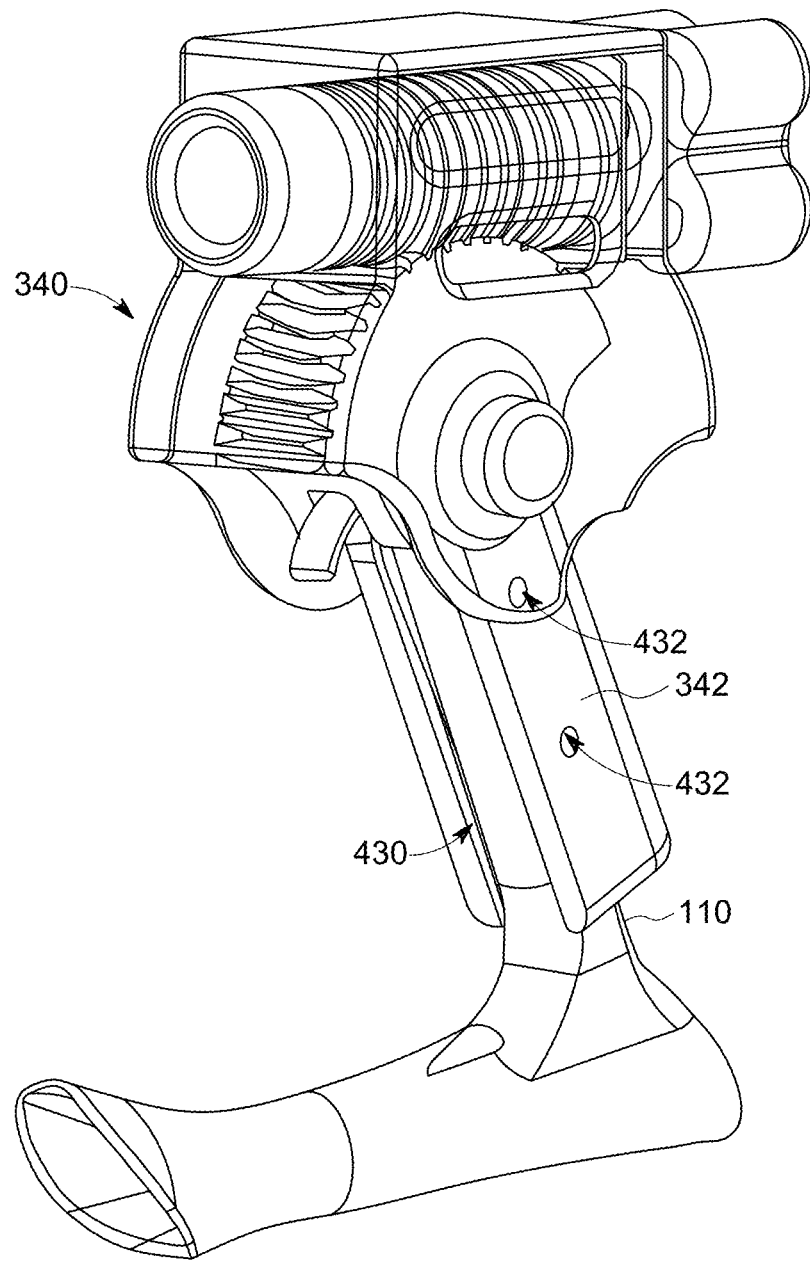
FIG. 5A is a perspective view of an elbow assembly with a laryngoscope, according to an embodiment.

FIG. 5A is a perspective view of an elbow assembly with a laryngoscope, according to an embodiment. The handle 110 of a laryngoscope 100 can be engaged with the holder 342. In the embodiment, the handle 110 can be inserted in an engagement area 430 of the holder 342. The at least one securing hole 432 of the holder can be aligned with the at least one securing hole 114 of the handle. A bolt, pin, screw, or other securing means can be inserted through the holder and the handle, thereby securing the handle 110 to the holder 342. The bolt, pin, screw, or other securing means can be non-metallic and can be made out of a polymer. The handle 110 can be secured to the holder 342 in a fixed relationship.

Figure 5B:
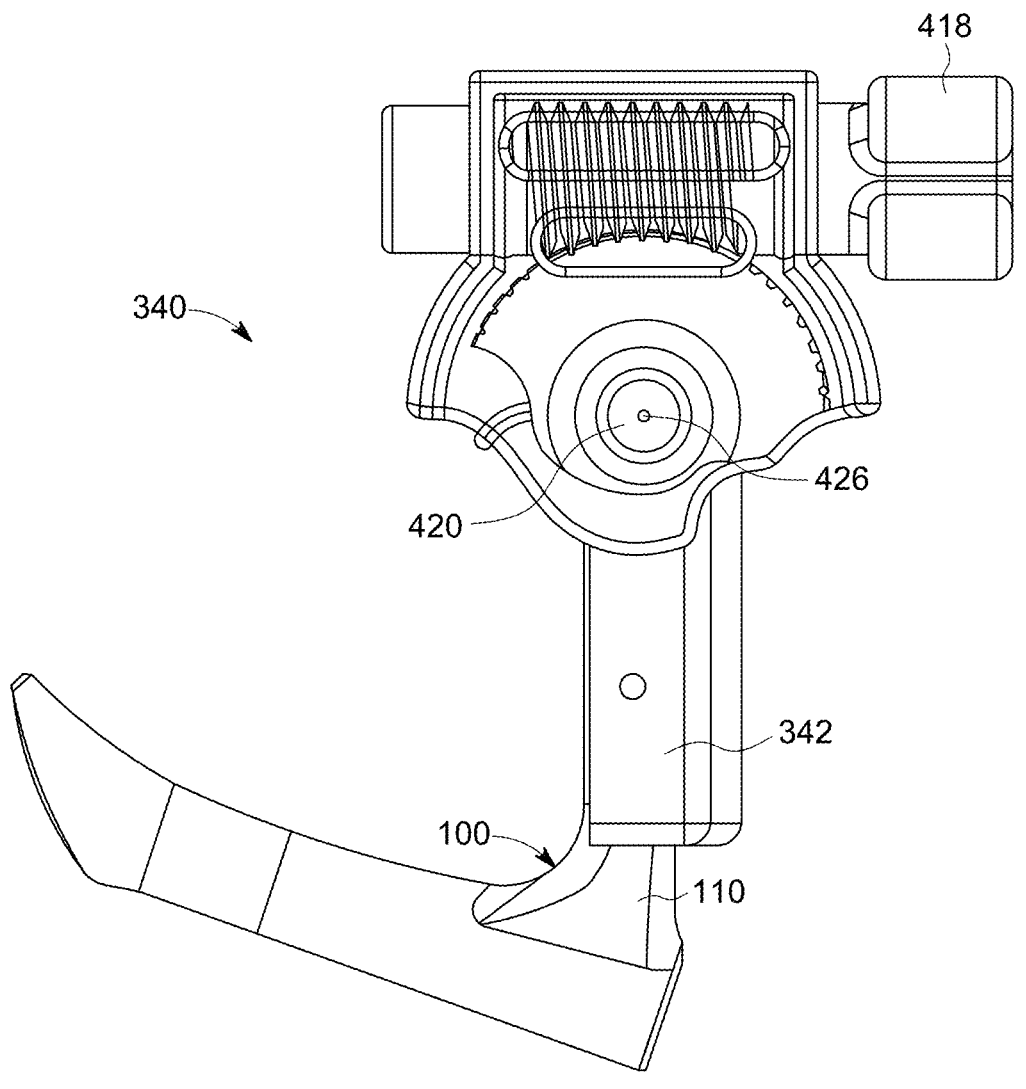
FIG. 5B is a side view of an elbow assembly with a laryngoscope, according to the embodiment.
Figure 5C:
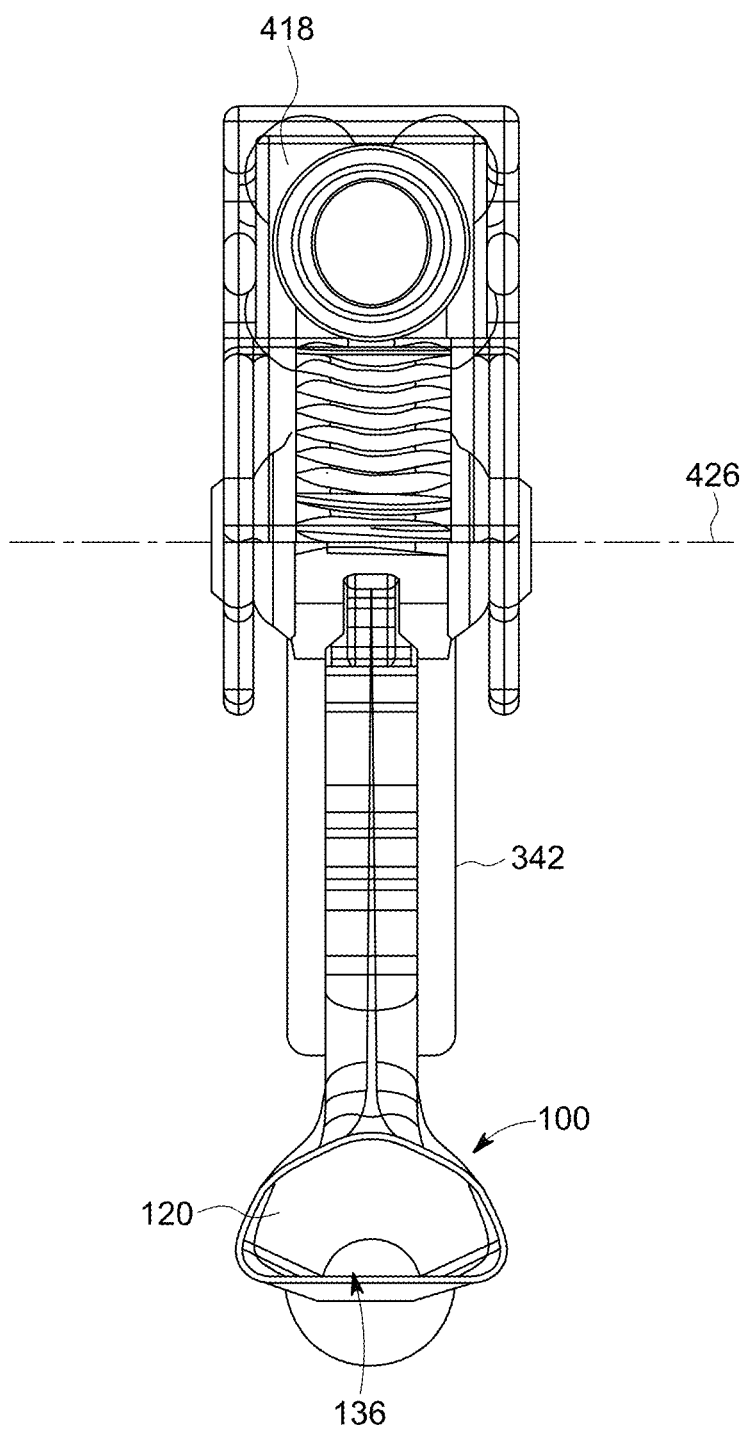
FIG. 5C is an end view of an elbow assembly with a laryngoscope; according to an embodiment.

FIG. 5B is a side view of an elbow assembly with a laryngoscope, according to the embodiment. When a user turns the knob 418, the holder can rotate around the central axis 426 on the axle 420. The handle 110 can be secured to the holder 342 in a fixed relationship, and the laryngoscope 100 can move unitarily with the holder 342. FIG. 5C is an end view of an elbow assembly with a laryngoscope, according to the embodiment. The orientation of the insertion member 120 can be adjusted by turning the knob 418, causing the holder 342 and attached laryngoscope 100 to rotate around the central axis 426. A user can turn the knob 418 to adjust the orientation of the insertion member 120, thereby allowing the user to move the insertion member 120 into a desired position so that the user can look through the central lumen 136 at a desired orientation for viewing anatomical structures of the patient, such as the larynx.

Figure 6A:
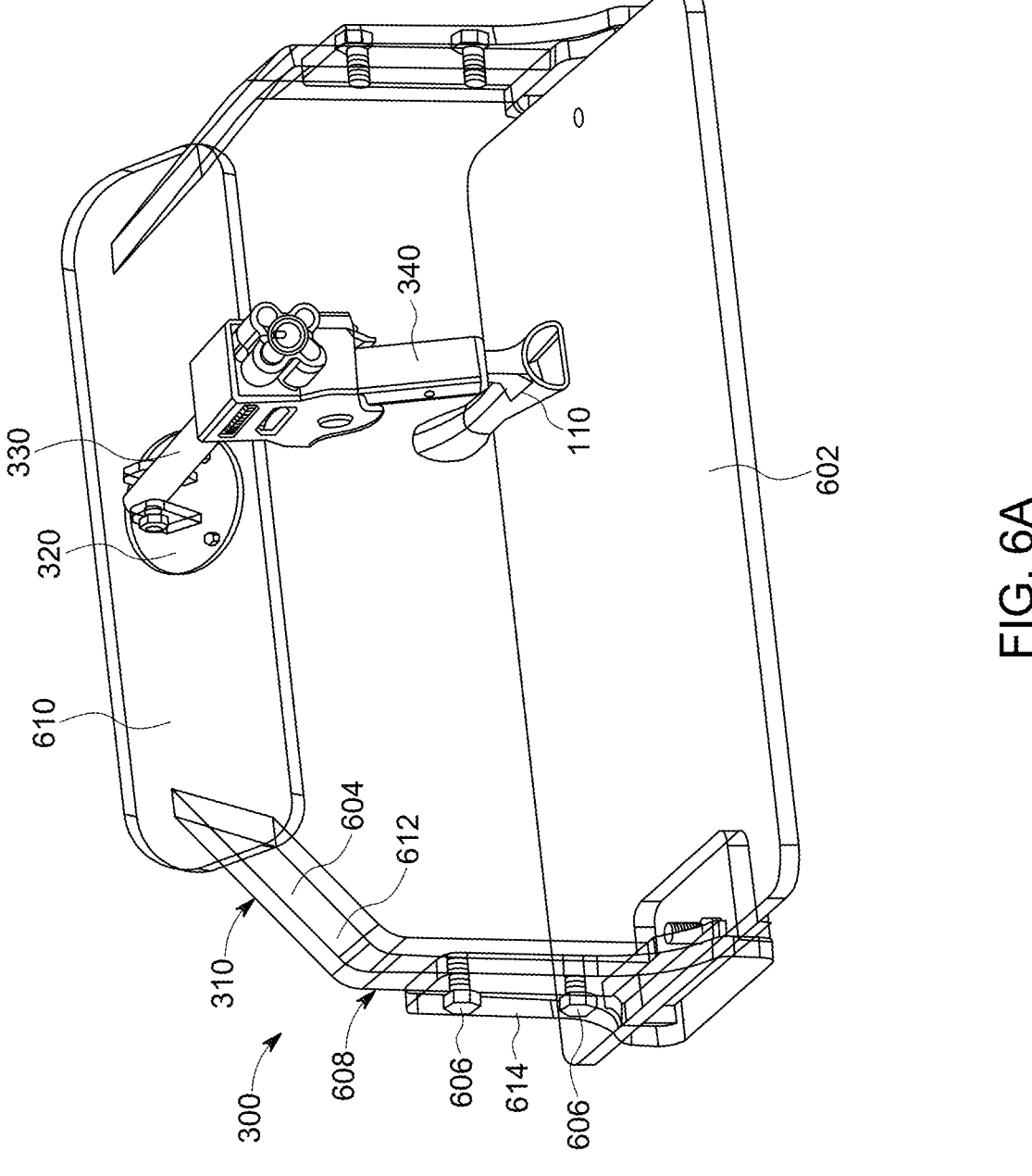
FIG. 6A is a perspective view of a support rig with an attached laryngoscope, according to an embodiment.

FIG. 6A is a perspective view of a support rig with an attached laryngoscope, according to an embodiment. The support rig 300 can have a frame 310, a wrist 320, an arm 330, and an elbow assembly 340, and a laryngoscope 100 can be mounted to the elbow assembly 340. It should be clear that the support rig 300 can be used with a laryngoscope and/or various retractors or other surgical instruments without departing from the scope of the present disclosure. The frame 310 can have a patient platform 602 and a tower 604. The tower 604 can be attached to the platform 602 with at least one tower bolt 606, or other means such as adhesives or welding, including plastics welding. In various embodiments, the patient platform 602 can a patient's bed, and the tower 604 can be attached directly to a portion of the patient's bed in one at one or more areas of the patent's bed, for example a bed frame, side rail, or other areas of the patent's bed. The tower 604 can extend upwards from the platform 602, and the wrist 320 can be mounted to the tower 604. The tower 604 can support components of the rig 300 above the patient, so that movements of the patient do not affect the position and orientation of the laryngoscope 100 that can be attached to the rig 300. The frame 310 can be placed on an operating table, imaging table, or other patient support surface. A patient can be positioned on the platform 602. The weight of the patient 200 can help to hold the support rig 300 in position on a patient surface, so that the laryngoscope 100 can be maintained in a desired position and orientation relative to the patient.

The tower 604 can have at least one leg 608 and a cross member 610. The at least one leg 608 can have an upper leg 612, a lower leg 614, and at least one leg bolt 616. In some embodiments, the height of the tower 604 can be adjustable by removing the at least one leg bolt 618, and extending the upper leg 612 into a desired position relative to the lower leg 614, and inserting the at least one leg bolt 618 to secure the upper leg 612 to the lower leg 614. The cross member 610 can be attached to the at least one leg 606, and the cross member 610 can extend over the patient. The wrist 320 can be mounted to the cross member 610, so that it can be above the patient. In alternate embodiments, the tower 604 can be arch-shaped or other shapes, and can connect to the platform in at least one place, so that the wrist 320 can be suspended from the tower 604. A user can remove all or part of the tower 604, and can then position the patient onto the platform 602, and then assemble the frame 310, including the tower 604, after the patient has been positioned.

Figure 6B:
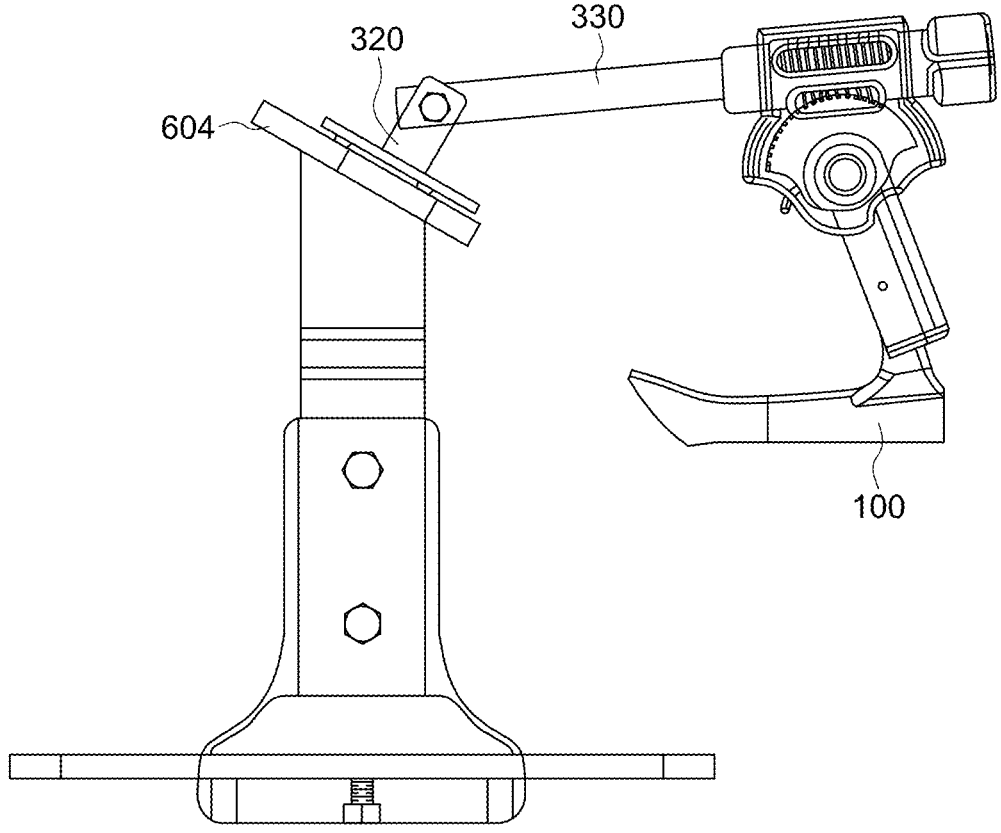
FIG. 6B is a side view of a support rig with an attached laryngoscope, according to the embodiment.

FIG. 6B is a side view of a support rig with an attached laryngoscope, according to the embodiment. The laryngoscope 100 can be maintained in a fixed orientation with the arm 330. The arm 330 can be hingedly mounted to the wrist 320 that is mounted to the tower 604. The tower 604 can support the wrist 320 and arm 330 above a patient.

Figure 6C:
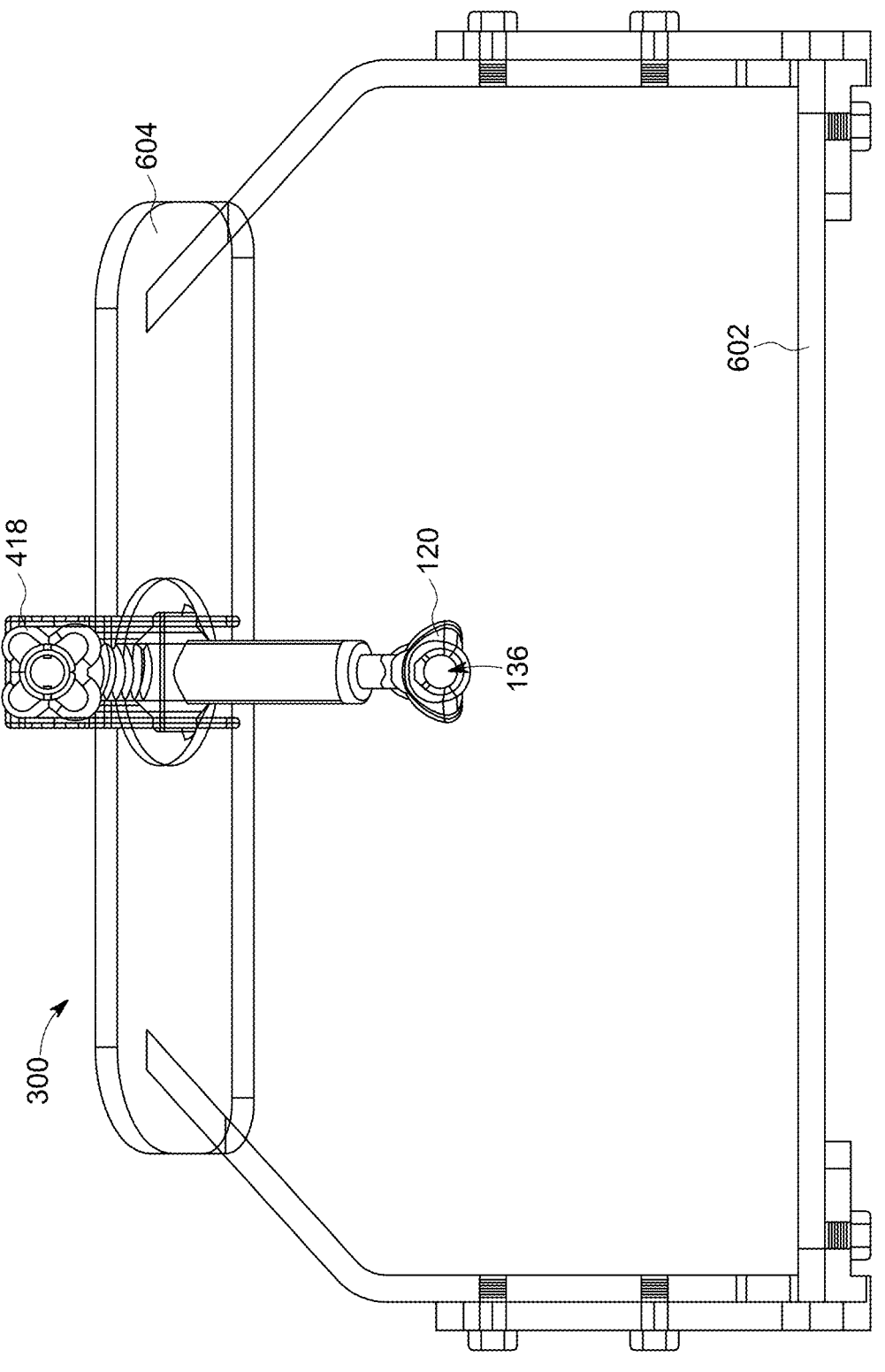
FIG. 6C is an end view of a support rig with an attached laryngoscope, according to the embodiment.
Figure 6D:
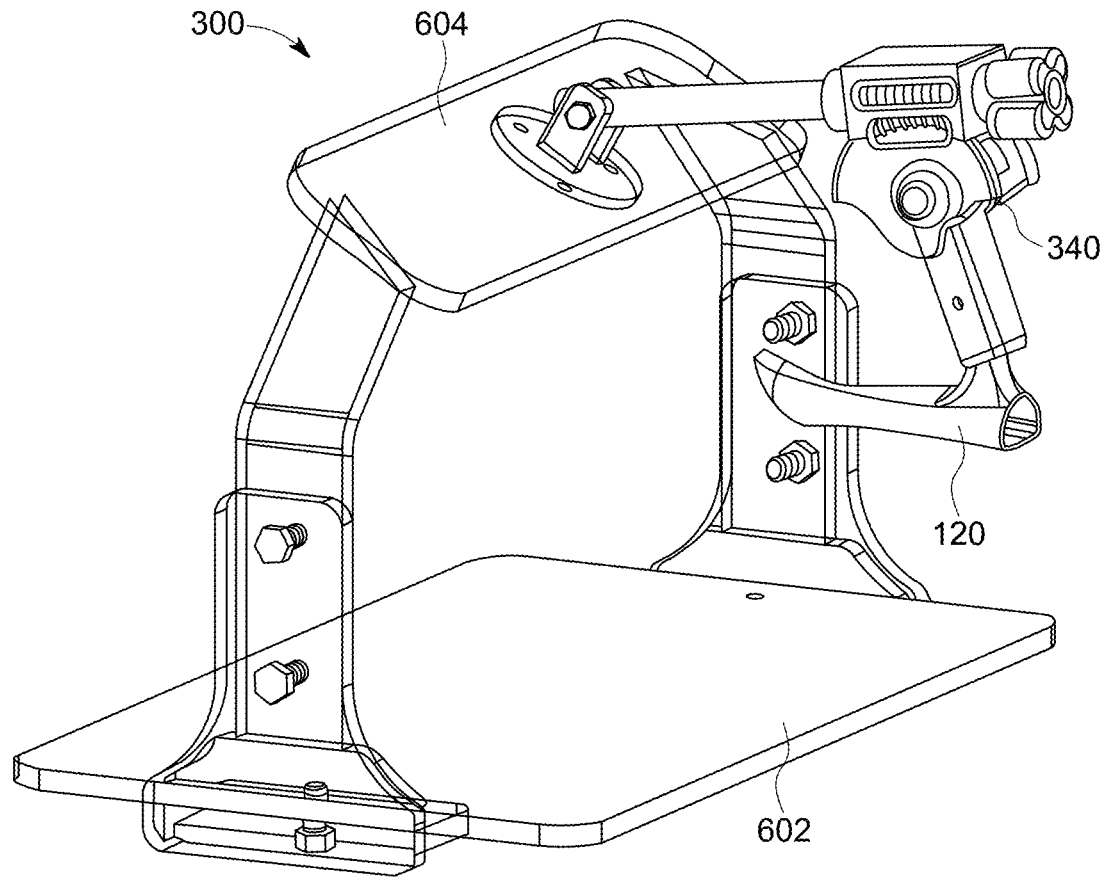
FIG. 6D is a perspective view of a support rig with an attached laryngoscope from an alternate perspective, according to the embodiment.

FIG. 6C is an end view of a support rig with an attached laryngoscope, according to the embodiment. A user can adjust the orientation of the insertion member 120 by turning the knob 418. Turning the knob 418 can adjust the angle of the central lumen 136, so that the user can look through the central lumen 136 and view the larynx or other anatomical structures of the patient at a desired angle. FIG. 6C depicts the central lumen 136 at an appropriate angle for a user to look through the central lumen from the given perspective. FIG. 6D is a perspective view of a support rig with an attached laryngoscope from an alternate perspective, according to the embodiment. The support rig 300 can support a laryngoscope that has been inserted into a patient (not shown), so that the laryngoscope can be maintained in a desired orientation relative to the patient that is not affected by breathing or other movements of the patient.

Figure 7A:
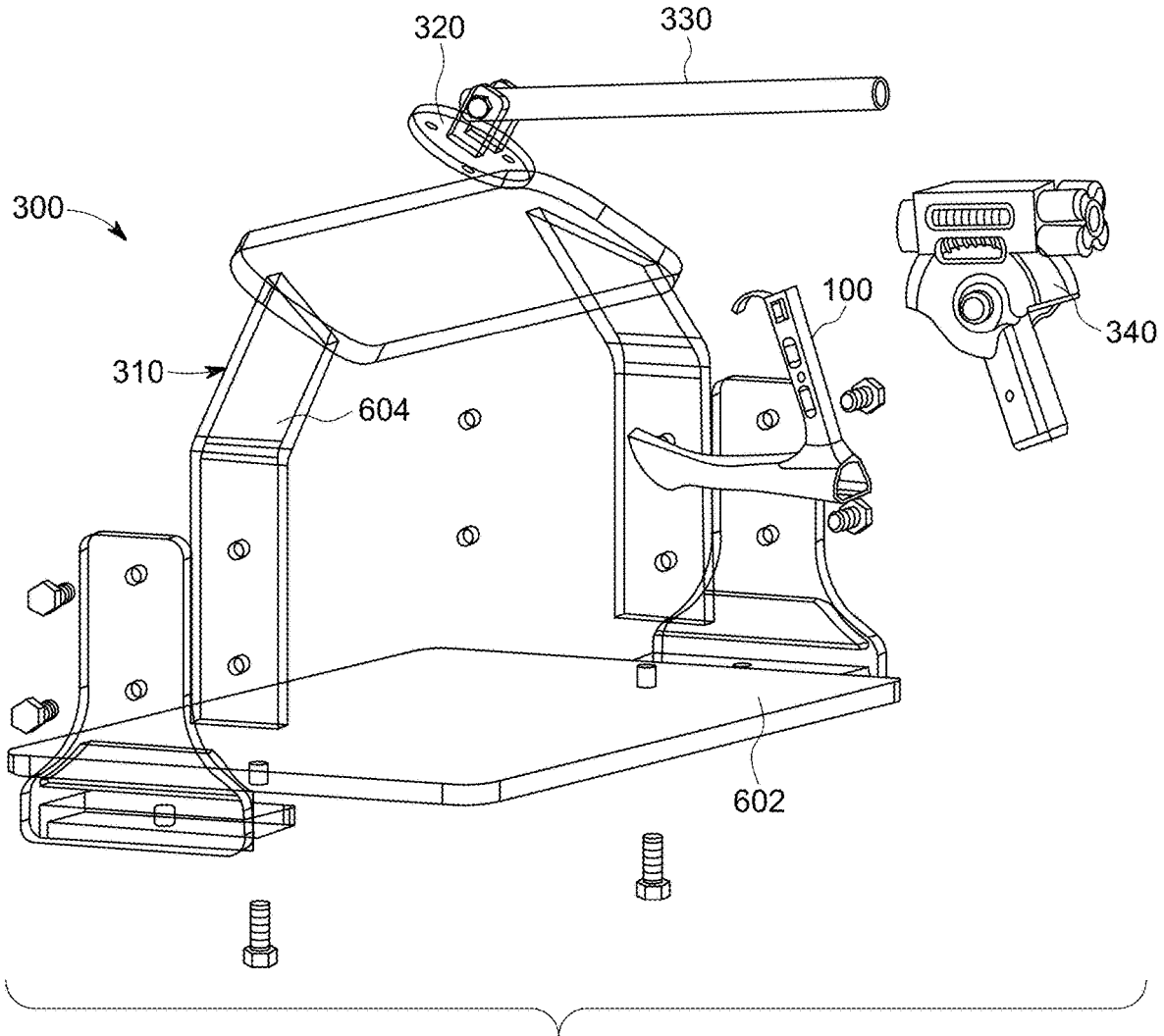
FIG. 7A is an exploded perspective view of a support rig and a laryngoscope, according to an embodiment.
Figure 7B:
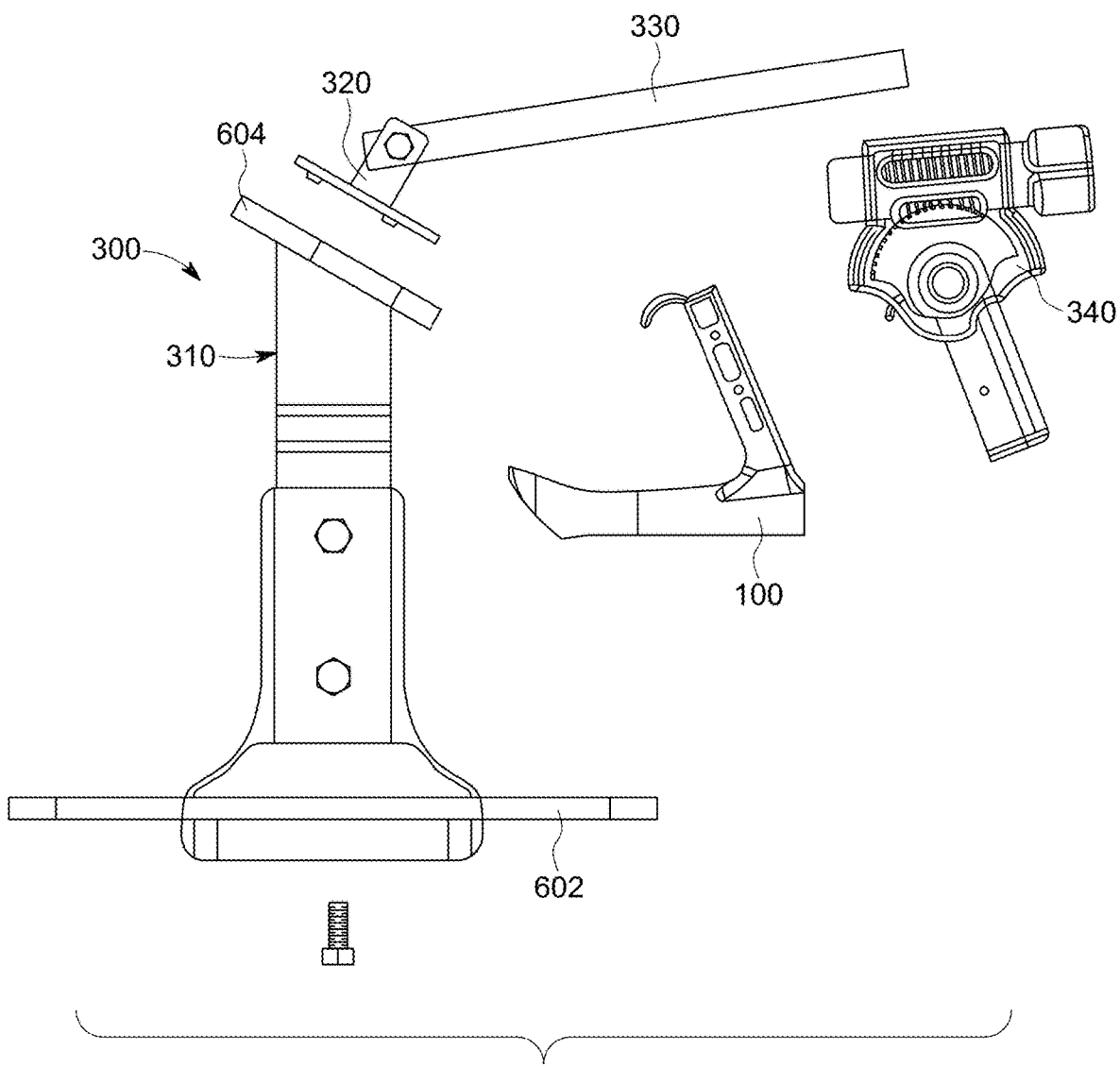
FIG. 7B is an exploded side view of a support rig and a laryngoscope, according to the embodiment.
Figure 7C:
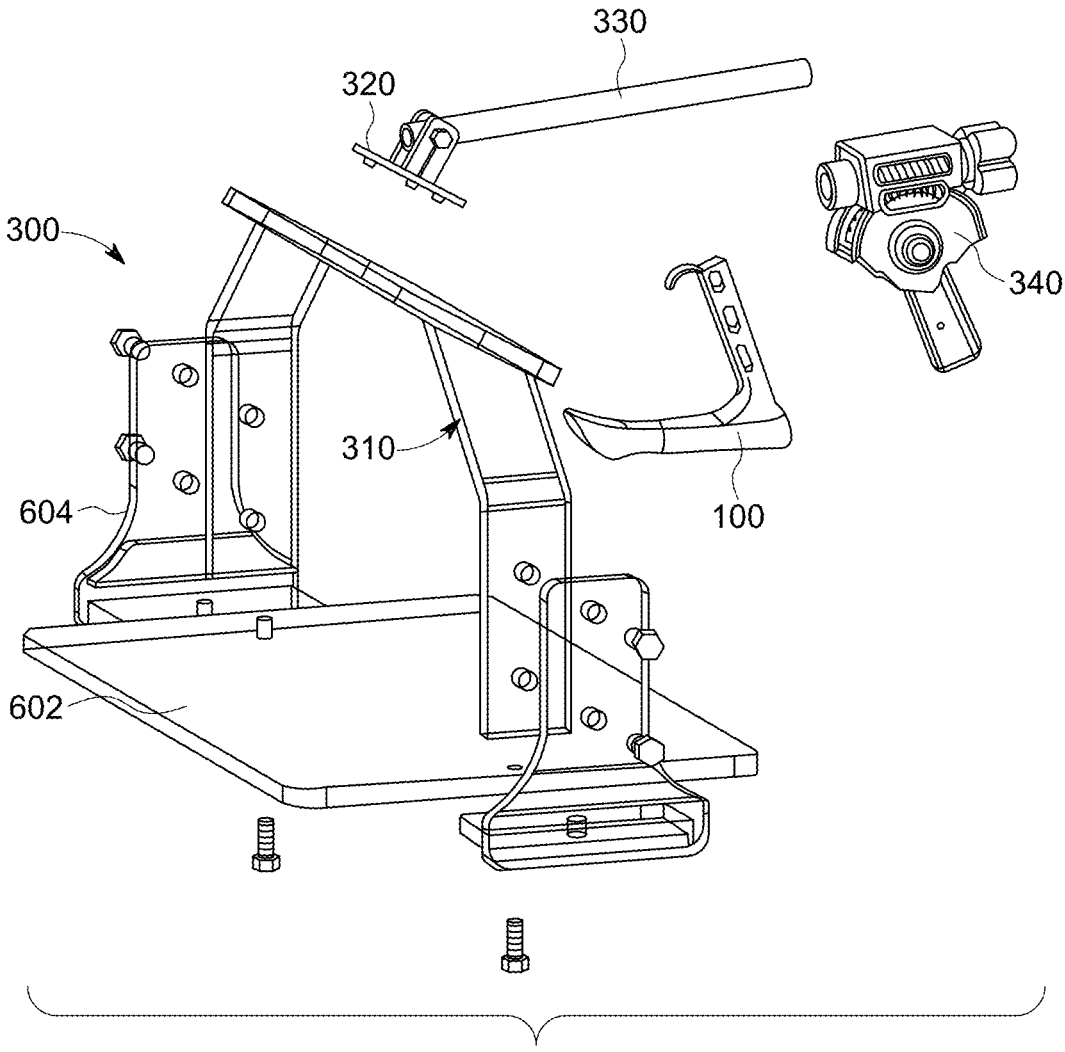
FIG. 7C is an exploded perspective view of a support rig and a laryngoscope from an alternate perspective, according to the embodiment.

FIG. 7A is an exploded perspective view of a support rig and a laryngoscope, according to an embodiment, FIG. 7B is an exploded side view of the support rig and laryngoscope, according to the embodiment, and FIG. 7C is an exploded perspective view of the support rig and laryngoscope from an alternate perspective, according to the embodiment. Turning to FIGS. 7A-7C, a support rig 300 can have a frame 310, a wrist 320, an arm 330, and an elbow assembly 340. The frame 310 can have a platform 602 and a tower 604. Prior to a surgery, various components of the support rig can be separate from other components of the support rig. The laryngoscope 100 can be separate and the elbow assembly 340 can be separate. The arm 330, wrist 320, and at least a portion of the tower 604 can assembled together, and can be separate from other components. The platform 602 can be separate, or can be assembled with at least a portion of the tower 604. The platform 602 can be placed on a patient support surface, such an operating table or imaging table. A patient can be placed on the patient support surface and on the platform 602. The platform 602, tower 604, wrist 320, and arm 330 can be assembled together. The elbow assembly 340 can be engaged with the arm 330. The elbow assembly 340 can slide along the arm 330 into a desired position. The laryngoscope 100 can be inserted into the patient. The laryngoscope 100 can be engaged with the elbow assembly 340. In an alternate embodiment, a tower can be attached to the platform at one location, and the tower can be hinged so that all of the tower, or a portion of the tower, can be hinged out of the way while a patient is loaded onto the platform, and the tower can then be hinged back into place after the patient has been loaded onto the platform. In another alternate embodiment, the tower can swivel out of the way while the patient is loaded onto the platform, and can then be swiveled back into place and locked into place. In an embodiment, platform 602 can be omitted and tower 604 can attach to the patient bed directly.

Figure 8A:
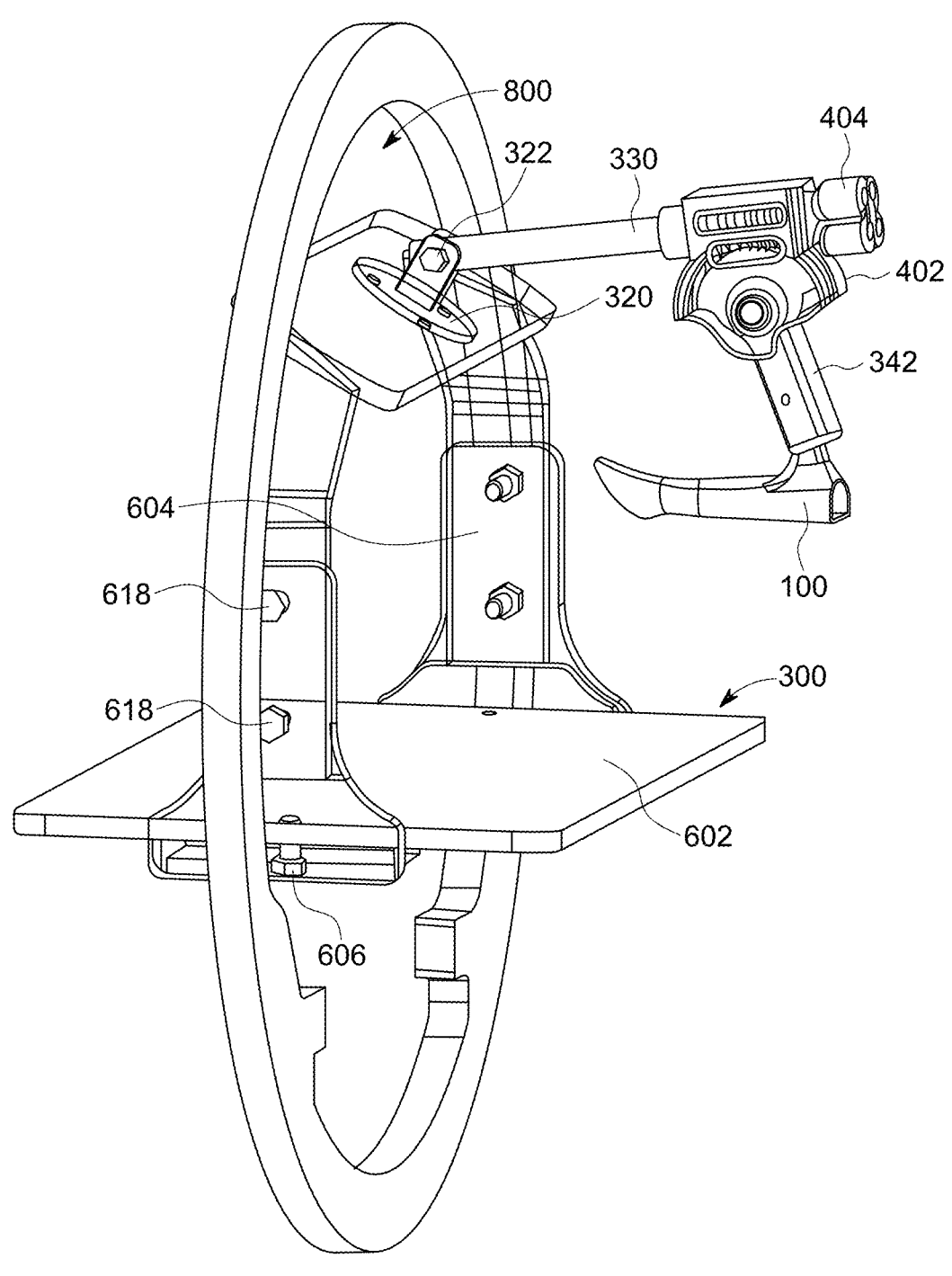
FIG. 8A is a perspective view of a support rig with an attached laryngoscope in the bore of a scanner, according to an embodiment.
Figure 8B:
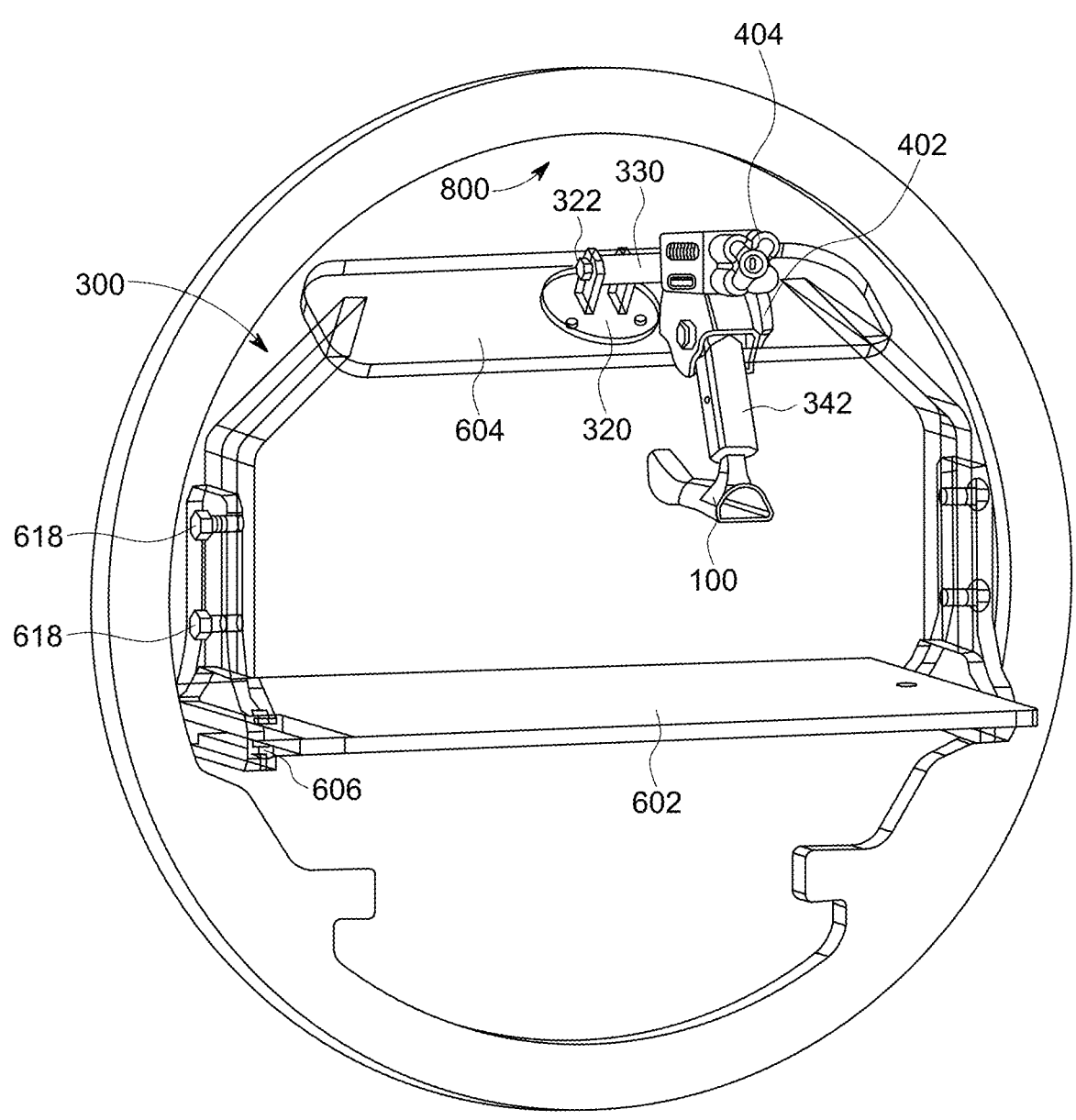
FIG. 8B is a perspective view of a support rig with an attached laryngoscope in the bore of a scanner from an alternate perspective, according to the embodiment.

FIG. 8A is a perspective view of a support rig with an attached laryngoscope in the bore of a scanner, according to an embodiment, and FIG. 8B is a perspective view of the support rig with the attached laryngoscope in the bore of a scanner from an alternate perspective, according to the embodiment. Turning to FIGS. 8A and 8B, an imager opening 800 is shown. The imager opening 800 can be the opening to an MRI scanner, a CT scanner, or other imaging equipment. The support rig 300 is adapted for use within various imaging devices, such as MRI scanners and CT scanners. The support rig 300 is free of metal components. The platform 602 can be made of a polymer such as poly(methyl methacrylate) (acrylic), or can be polyethylene, polycarbonate, polyamide (nylon) and/or polyvinyl chloride. The tower 604 can be made of a polymer such as poly (methyl methacrylate) (acrylic), or can be polyethylene, polycarbonate, polyamide (nylon) and/or polyvinyl chloride. The at least one tower bolt 606 and at least one leg bolt 618 can be made of a polymer such as poly(methyl methacrylate) (acrylic), or can be polyethylene, polycarbonate, polyamide (nylon), and/or polyvinyl chloride. The wrist 320 can be made of a polymer such as poly(methyl methacrylate) (acrylic), or can be polyethylene, polycarbonate, polyamide (nylon) and/or polyvinyl chloride. The hinge 322 can be made of a polymer such as poly(methyl methacrylate) (acrylic), or can be polyethylene, polycarbonate, polyamide (nylon), and/or polyvinyl chloride. The arm 330 can be made of a polymer such as poly(methyl methacrylate) (acrylic), or can be polyethylene, polycarbonate, polyamide (nylon), and/or polyvinyl chloride. The adjuster 404 and holder 342 can be made of a polymer such as poly(methyl methacrylate) (acrylic), or can be polyethylene, polycarbonate, polyamide (nylon), and/or polyvinyl chloride. The outer shell 402 can be made of a polymer such as poly(methyl methacrylate) (acrylic), or can be polyethylene, polycarbonate, polyamide (nylon), and/or polyvinyl chloride. The laryngoscope 100, that can be made of a polymer such as poly(methyl methacrylate) (acrylic), or can be polyethylene, polycarbonate, polyamide (nylon) and/or polyvinyl chloride, is adapted for use in imaging devices. The support rig 300, with an attached laryngoscope 100, can shaped and sized to be adapted for use within the bore of an imaging device. Because the support rig 300 and laryngoscope 100 are made of non-metallic materials, and because they are shaped and sized to fit within the bore of an imaging device, a patient with an inserted laryngoscope 100 can be inserted into an imaging device and an image can be taken of the patient with the inserted laryngoscope 100 that is supported by the rig 300.

A user can obtain an image of anatomical structures of a patient while the laryngoscope 100 is inserted in the throat, and while the laryngoscope is supported by the rig 300, so that the images obtained by the user will accurately show the locations of tumors or other anatomical structures while the user's head is tilted back and the laryngoscope is inserted. The rig 300 can maintain the position and orientation of the laryngoscope 100 while the patient is inserted into an imaging device, an image is taken, the patient is removed from the imaging device, and/or surgery is performed on the patient. The rig enables the user to rely on the images as being accurate while surgery is performed, because the position and orientation of the laryngoscope relative to the patient does not change after the user fixes the position and orientation of the laryngoscope relative to the patient, unless the user readjusts the position and orientation of the laryngoscope. A user can fix the position and orientation of the laryngoscope 100, then take an image of the patient with the laryngoscope 100 inserted, and can then adjust the position and orientation of the laryngoscope 100, if necessary, based on the information obtained in the image taken with the inserted laryngoscope 100. The process of adjusting the position and/or orientation of the laryngoscope 100, then taking an image, and then readjusting the position and/or orientation or the laryngoscope 100 can be repeated as necessary until the laryngoscope has been adjusted into the desired position and orientation.

It should be clear that a rig 300 is not limited to holding laryngoscopes, and a rig can be used to support a variety of medical instruments, including other retractors, that can be used during surgery, including laparoscopy instruments or others. A variety of instruments for various surgeries can be inserted into a patient and can be supported in a rig. A rig can maintain the position and orientation of various instruments relative to a patient without being impacted by the breathing or other movements of a patient. A non-metallic rig can maintain the position and orientation of various non-metallic instruments relative to a patient while the patient is undergoing an imaging process.

II. IGTORS

Figure 9A:
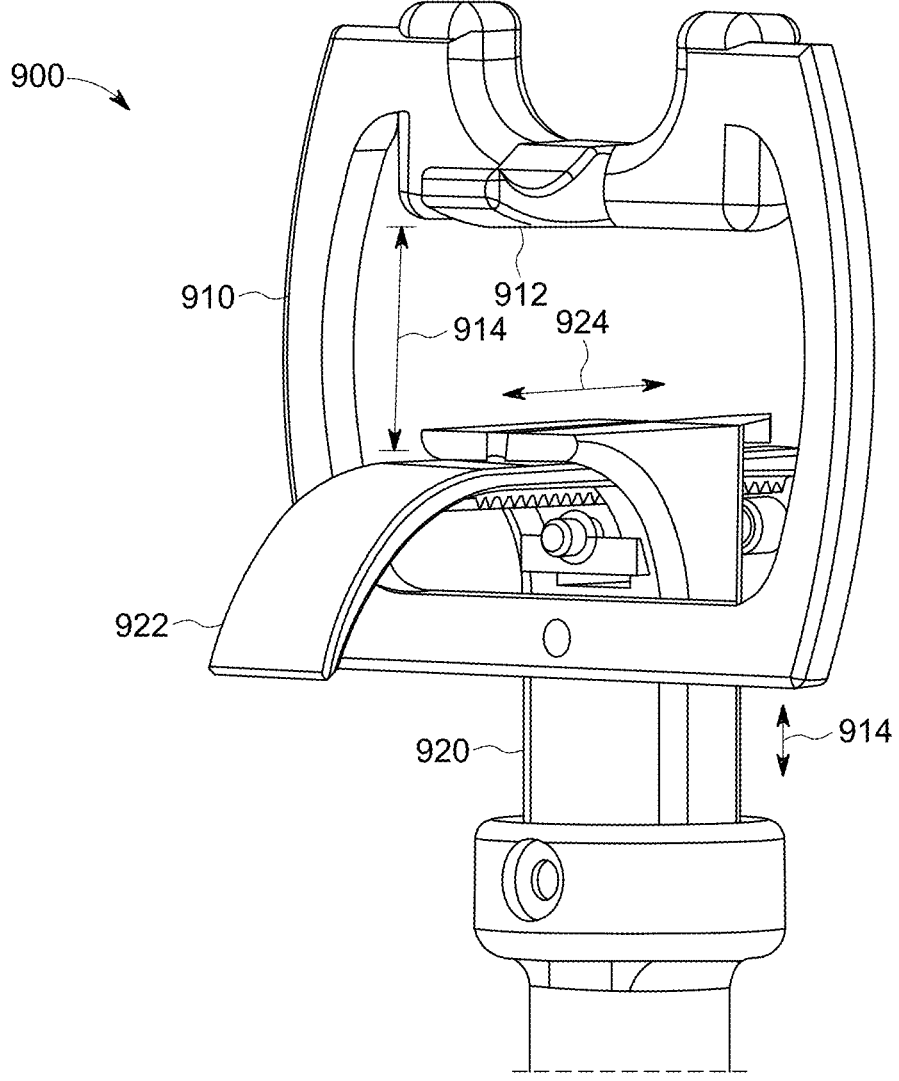
FIG. 9A is a perspective view of a patient facing portion of a retractor that can be used in Image-Guided Trans-Oral Robotic Surgery, according to an illustrative embodiment.

A radiopaque and MR compatible retractor can be used with the above-described rig 300 to enable image guided robotic surgery, such as Image-Guided Trans-Oral Robotic Surgery (IGTORS) according to novel implementations herein. FIG. 9A is a perspective view of a patient facing portion of a retractor that can be used in Image-Guided Trans-Oral Robotic Surgery, according to an illustrative embodiment. The IGTORS retractor 900 can be adjustable and/or customized, including custom-printed, to suit the shape of individual patients, particular tumor locations, required surgical angles, surgeon preferences, and other parameters. This system and method particularly enables access to the oropharynx—the tongue base, soft palate, posterior pharynx of the patient.

As shown in FIG. 9A, an IGTORs retractor 900 can have a body 910 with a maxillary blade 912 that can sit over the patient's mouth and registers to the anterior maxilla. Tongue blade 922 can retract a patient's tongue, and the user can adjust the depth of the tongue blade to fit an individual patient. The tongue blade 922 can be adjusted into and out of the mouth of the patient relative to the shaft 920 along arrow 924, and body 910 can move relative to the shaft 920 along arrow 914. Moving the body 910 relative to the shaft 920 moves the maxillary blade 912 relative to the tongue blade 922, and increases and decreases the distance MO between the maxillary blade 912 and the tongue blade 922. Distance MO directly effects the size of the mouth opening of the patient, or put another way, directly affects how far the patient's jaw is held open. Increasing the mouth opening distance MO allows more room for various surgical tools to be inserted into the oral cavity and maneuvered to perform surgery.

FIG. 9B is a perspective view of a tongue blade, according to an illustrative embodiment, and FIG. 9C is a cross section of the tongue blade taken along cross section line 9C-9C. A transverse rib 926 spanning from one side of the tongue blade to the other can increase the strength of a blade that is made of a polymer or other radiolucent material. Similarly, an arch 928 in the blade from one side to the other, as shown in the cross sectional view of FIG. 9C, can add additional strength to a blade 922. These strength-adding features can allow the entire retractor to be made of softer radiolucent polymers instead of more traditional materials such as rigid metals.

In various embodiments, a retractor can include sensors 936. Sensors 936 can be force sensors, flex sensors, or various other sensors that can provide feedback to the user regarding the condition of the patient and the retractor. Force sensors may inform the current status of the patient, including tensions on the anatomical structures, and may inform post-operative care, including the need for post-operative medications.

In various embodiments, a retractor 900 can be made from a variety of materials, including 3D printed polymers. Tongue blades can be made from the same materials as the rest of the retractor, or can be made from different materials such as carbon fiber and/or can be made from one material and filled with another, such as an epoxy filling to improve the overall stiffness of the blade.

Figure 9D:
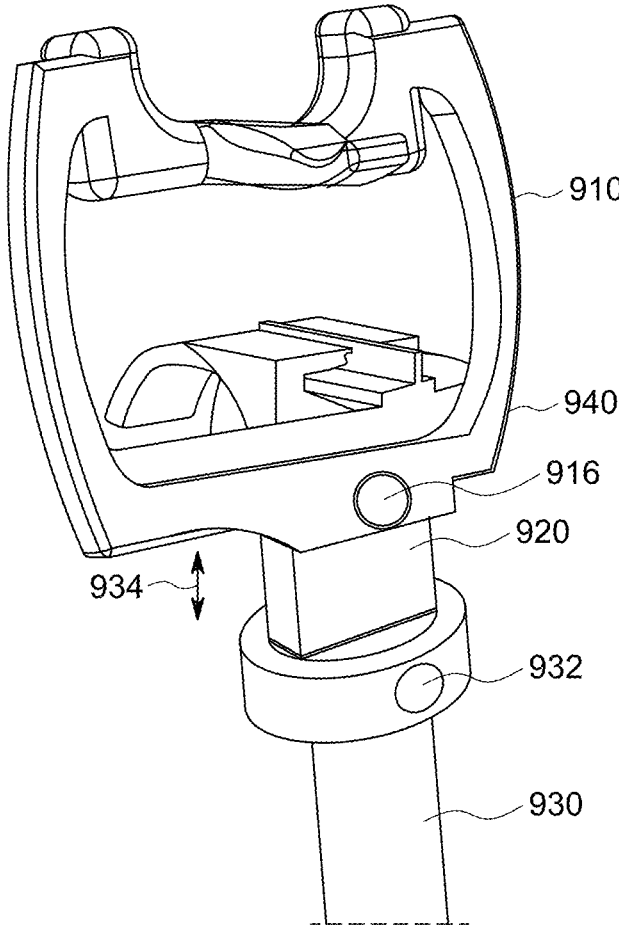
FIG. 9D is a perspective view of an IGTORS retractor from a surgeon's perspective, according to an illustrative embodiment.

FIG. 9D is a perspective view of an IGTORS retractor from a surgeon's perspective, according to an illustrative embodiment. In an embodiment surgeon can move the body 910 relative to the shaft 920 to adjust the size of the mouth opening by loosening a set screw 916, sliding the body relative to the shaft, and tightening the set screw 916. It should be clear that various means for selectively securing the body relative to the shaft are possible, including a set screw, a clamp, pins and holes, or various other means that will be clear to one of skill in the art. Similarly, a set screw 932 can allow a surgeon to selectively loosen the shaft 920 from the end of a shaft holder 930 of the elbow, so that the shaft 920 can slide relative to the shaft holder 930 along arrow 934. An adjustment screw 940 allows the surgeon to set the depth of the tongue blade 922 relative to the shaft 920.

Figures 10A, 10B:
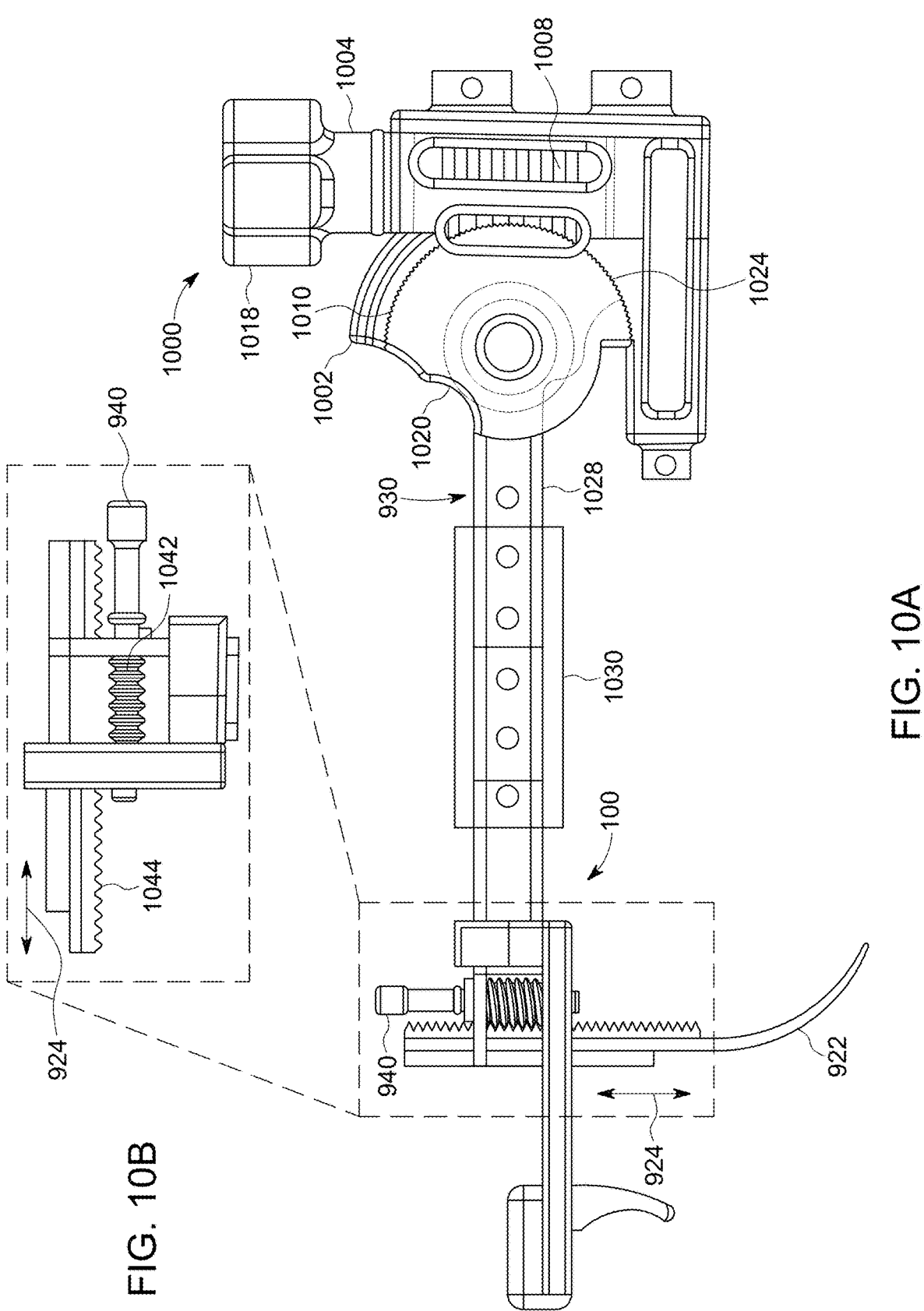
FIG. 10A is a side view of an IGTORS retractor adjustably connected to an elbow, according to an illustrative embodiment.
FIG. 10B is an enlarged view of the blade depth adjustment mechanism shown in FIG. 10A, according to an illustrative embodiment.

FIG. 10A is a side view of an IGTORS retractor adjustably connected to an elbow, and FIG. 10B is an enlarged view of the blade depth adjustment mechanism shown in FIG. 10A, according to an illustrative embodiment. As shown in FIG. 10B, adjustment screw 940 is operatively connected to worm gear 1042, which is in turn intermeshed with rack 1044 on the tongue blade 922, so that a user can move the tongue blade 922 along arrow 924 by twisting the adjustment screw 940.

Various elbow assemblies can be used to connect various retractors to the arm of the support rig. An elbow assembly 1000 can allow a user to adjust the orientation of a retractor 900 relative to a support rig, and the elbow assembly can maintain the angle of the retractor relative to the support rig in a fixed orientation. It should be clear that the elbow assembly can be used with a variety of retractors or other surgical instruments without departing from the scope of the present disclosure, and that various elbow assemblies are possible. A user can fine tune the angle of the retractor and fix the angle so that it remains in the selected position. An elbow assembly can have an outer shell 1002, an adjuster 1004, and a shaft holder 930.

Figure 10C:
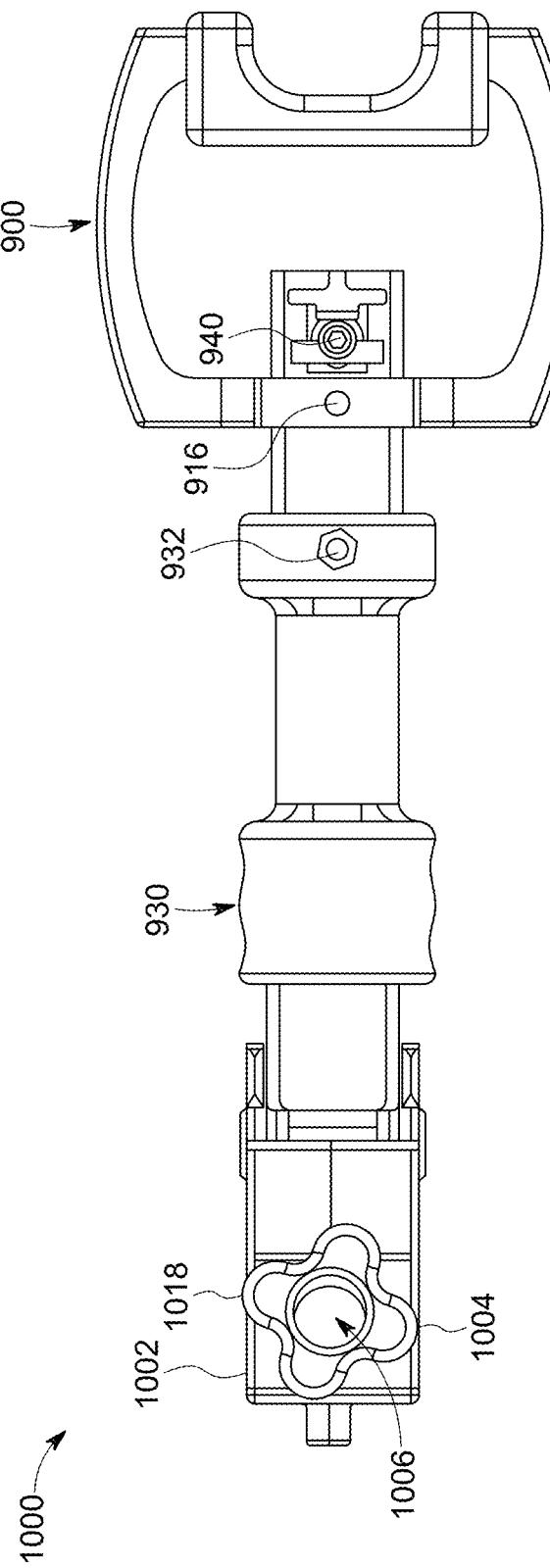
FIG. 10C is a top view of an IGTORS retractor assembly connected to an elbow, according to another illustrative embodiment.

FIG. 10C is a top view of an IGTORS retractor assembly connected to an elbow, according to another illustrative embodiment. Turning to FIGS. 10A and 10C, an elbow assembly 1000 can have a bore 1006. The bore 1006 can be an opening in the elbow assembly 1000 adapted to engage with the arm of a support rig. The bore 1006 can be through the adjuster 1004. The arm can be inserted through the bore 1006, and the adjuster 1004 can rotate on the arm. In alternate embodiments, an elbow assembly can have a mounting platform, spring-loaded pins and holes, or various other means to attach the elbow assembly to the mounting platform. In alternate embodiments, the elbow assembly can clip onto the arm or otherwise be attached to the arm in various ways that will be apparent to one skilled in the art.

The elbow assembly 1000 can have a worm gear 1008 and a rack 1010. The worm gear 1008 can be on the adjuster 1004 and the rack 1010 can be on the holder 930. The outer shell 1002 can hold the worm gear 1008 in engagement with the rack 1010. The adjuster can have a knob 1018. The knob 1018 can protrude through a proximal opening, so that the adjuster 1004 can be held within the outer shell 1002, and can rotate in place within the outer shell 1002. The elbow assembly can have at least one axle 1020. The at least one axle 1020 can be a part of the holder 930 that extends from the holder 930 and can be engaged by the outer shell 1002, so that the holder can pivot relative to the outer shell 1002 on the axle 1020. The at least one axle 1020 can extend through the holder 930 and be engaged by the outer shell 1002, so that the holder 930 can pivot relative to the outer shell 1002 on the axle 1020.

The holder 930 can have an upper arc 1024 that can be a segment of a cylinder with a central axis that passes through the axle 1020. The rack 1010 can be arranged along the circumference of the upper arc 1024, so that teeth of the rack 1010 can be equidistant from the central axis that passes through the axle 1020. A user can turn the knob 1018, which can cause the adjuster 1004 to rotate within the outer shell 1002 and turn the worm gear 1008. The turning worm gear 1008 can cause the rack 1010 to rotate around the central axis, with the holder turning on the at least one axle 1020. When the user turns the knob 1018, causing the holder 930 to turn on the at least one axle 1020, the angle between holder 930 and the arm (not shown) can be selectively adjusted.

The holder 930 can have an engagement arm 1028 adapted to engage with the handle. In various embodiments, the engagement arm 1028 can have a sleeve 1030 that can be sized and shaped to be adapted to hold the retractor. The engagement arm 1028, the sleeve 1030, and the retractor 900 can be arranged to telescope one within the other so that the distance between the tongue blade and the elbow assembly 1000 can be easily adjusted by the user. In various embodiments spring loaded pins, bolts, clamps, or various means can be used to selectively secure the telescoping components together to fix the distance between the rig and the tongue blade. A telescoping arrangement is shown in FIGS. 10A and 10C, however, it should be clear to one skilled in the art that various means for connecting the retractor to the engagement arm are possible.

The bore 1006 can be an opening through the elbow assembly 1000. The bore 1006 can have a shape that is adapted to the shape of the elbow end of the arm, so that arm can be inserted into the bore 1006. In the embodiment, the arm can be cylindrical, and the bore 1006 can be cylindrical and can be through the adjuster 1004, so that the adjuster 1004 can rotate around the arm.

Figure 11A:
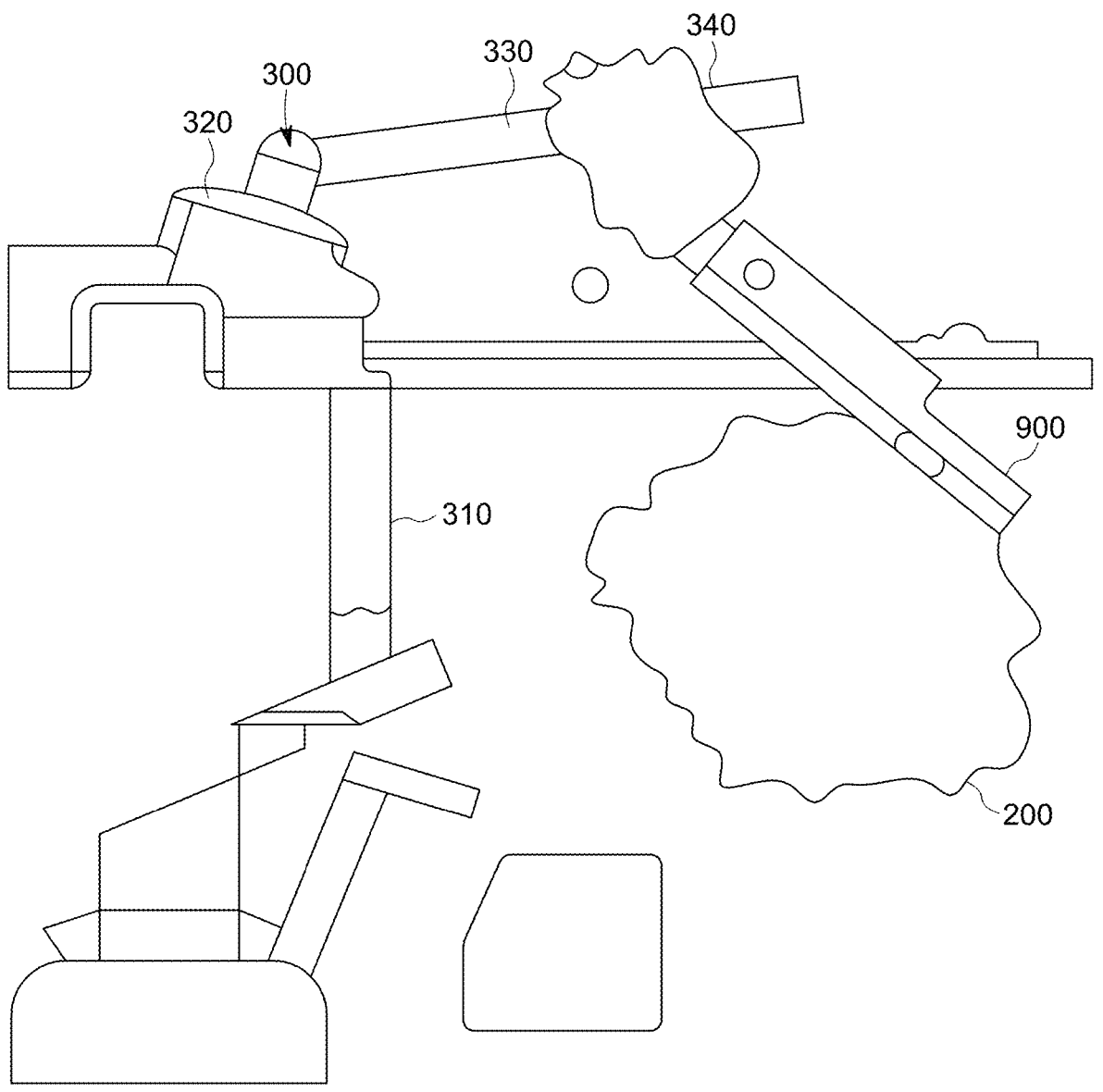
FIG. 11A is a side view of a retractor attached to a support rig and holding open a mouth of a patient, according to an illustrative embodiment.
Figure 11B:
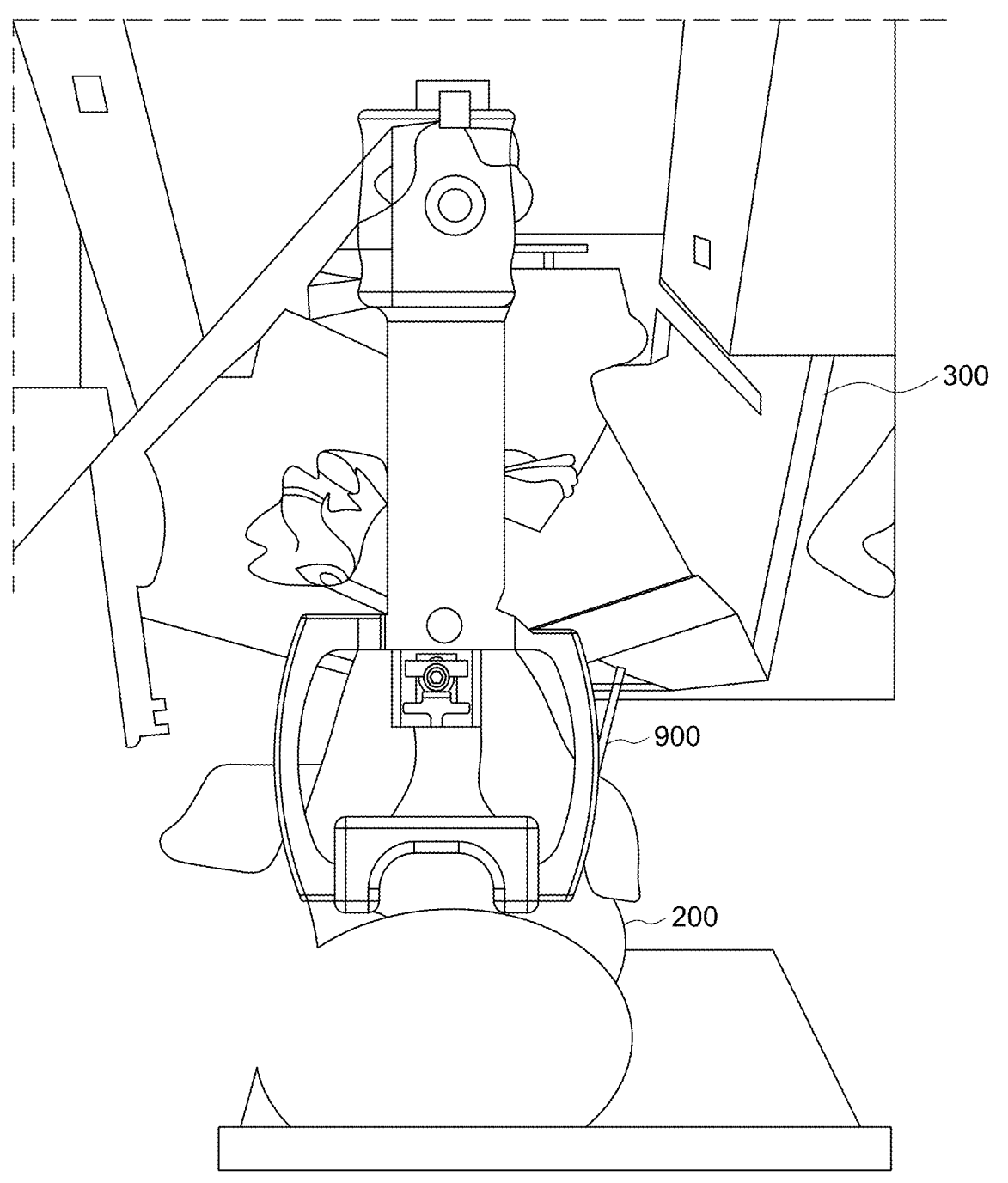
FIG. 11B is a top view of the retractor of FIG. 11A attached to a support rig and holding open the mouth of the patient, shown from a surgeon's perspective, according to an illustrative embodiment.

FIG. 11A is a side view of a retractor attached to a support rig and holding open a mouth of a patient, according to an illustrative embodiment, and FIG. 11B is a top view of the retractor of FIG. 11A attached to a support rig and holding open the mouth of the patient, shown from a surgeon's perspective, according to an illustrative embodiment. The support rig 300 can hold the retractor 900 in a selectable fixed position without the user needing to hold the retractor. The retractor is maintained in the selected fixed position without being impacted by breathing or other movement of the patient 200. A support rig 300 can have a wrist 320, an arm 330, and an elbow assembly 340. A support rig can include, or be attached to, a support frame 310. A frame 310 can provide a base for the support rig 300, so that the retractor 900 can be supported above the patient. This arrangement results in the mouth of the patient being maintained in an open position so that robotic surgical instruments, including remotely operated robotic surgical instruments, can be inserted into the mouth and be manipulated by the surgeon in the oral cavity.

Figure 11C:
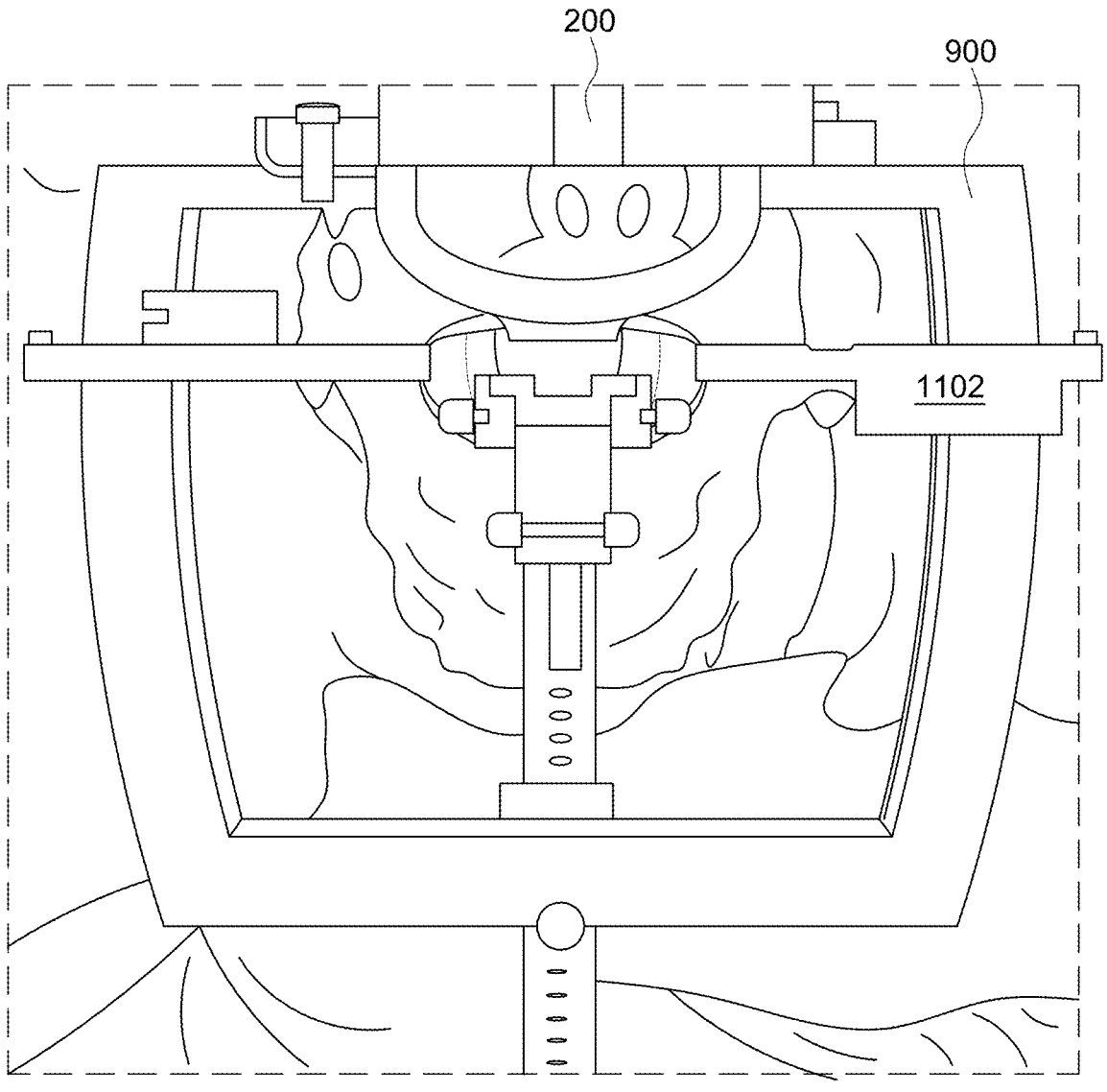
FIG. 11C is a top view of a retractor with additional side hooks, according to an illustrative embodiment.

FIG. 11C is a top view of a retractor with additional side hooks, according to an illustrative embodiment. A wide variety of retractors can be custom designed and used during IGTORS. As shown in FIG. 11C, a retractor 900 can have various modifications, including, for example, side hooks 1102 that can be added to a retractor to hold open the sides of a mouth of a patient 200.

Figure 11D:
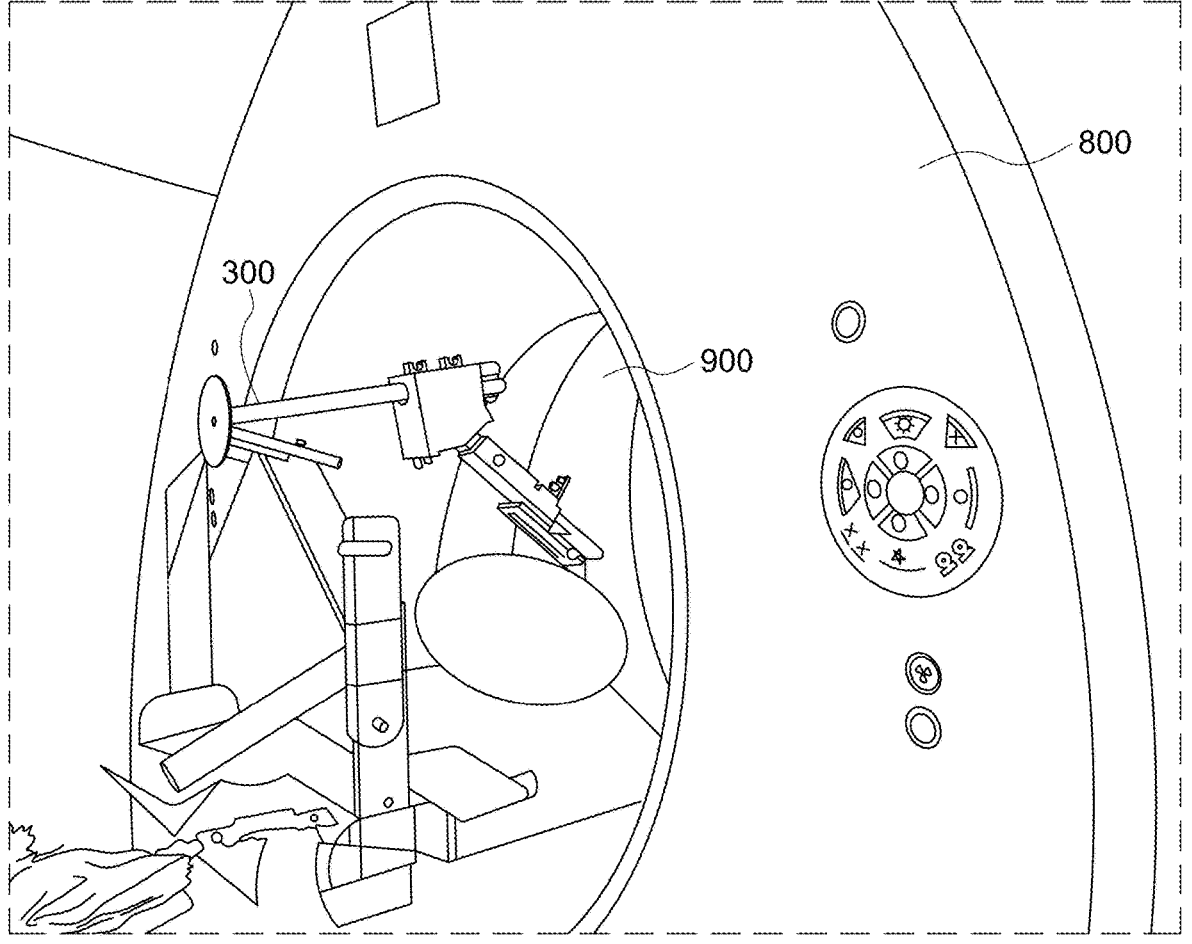
FIG. 11D is a perspective view of a retractor attached to a support rig and holding open a mouth of a patient in the bore of an imaging device, according to an illustrative embodiment.

FIG. 11D is a perspective view of a retractor attached to a support rig and holding open a mouth of a patient in the bore of an imaging device, according to an illustrative embodiment. Imager 800 can be a medical imaging device such as a CT scanner or MRI. The support rig 300 and the retractor 900 are radiolucent and metal free, and are shaped and sized to be adapted for use within the bore of an imaging device. A user can obtain medical images of a patient's anatomy while simultaneously performing surgery on the patient. Surgery on the patient can include Trans-Oral Robotic Surgery (TORS) and Image-Guided TORS (IG-TORS).

Figures 12A, 12B:
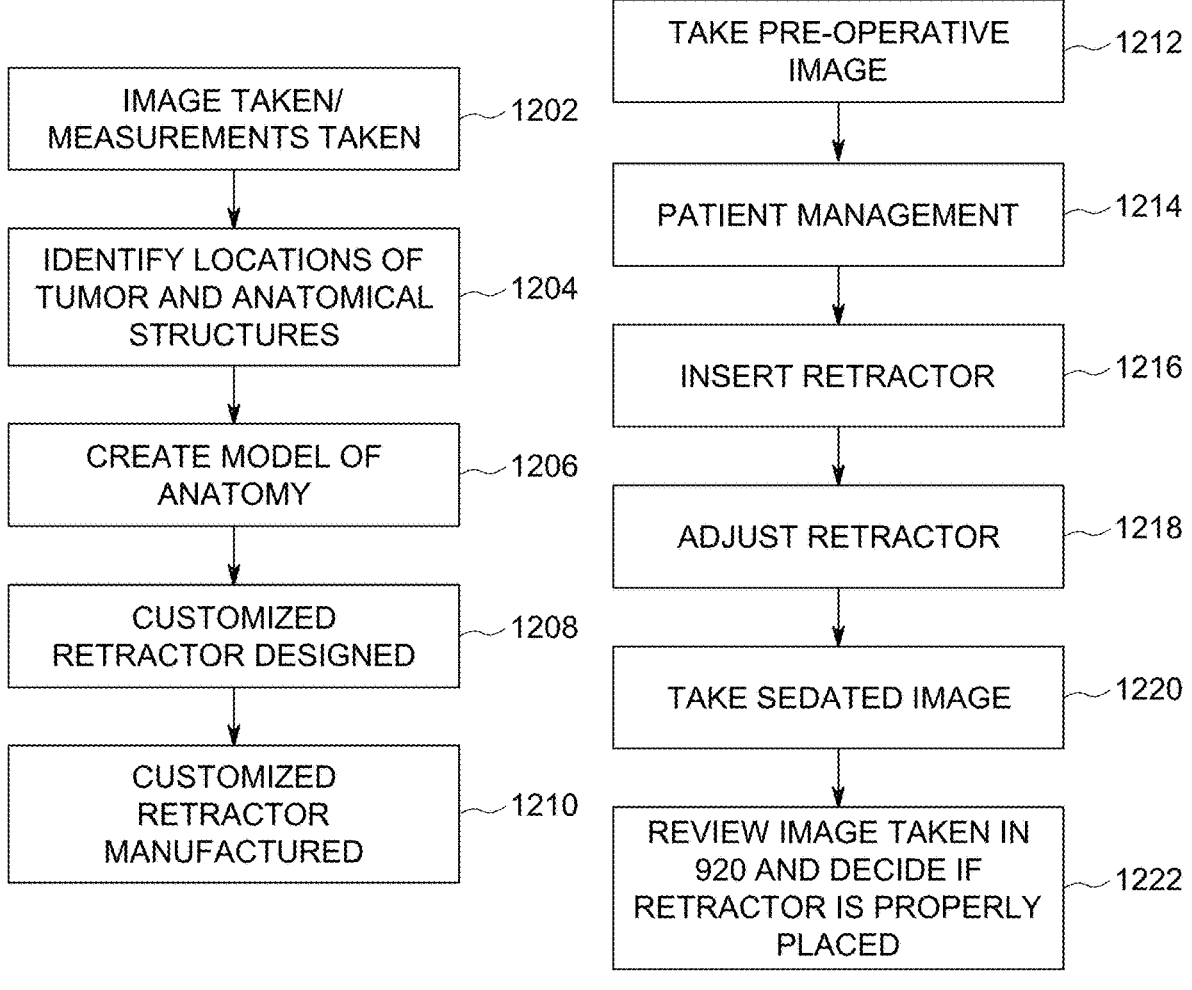
FIG. 12A is a flowchart showing the steps for making a customized laryngoscope, according to an embodiment.
FIG. 12B is a flowchart describing the use of a laryngoscope and support rig to obtain images to inform a medical procedure, according to an embodiment.

FIG. 12A is a flowchart showing the steps for making a customized retractor, according to an embodiment. At box 1202, an image can be taken of anatomical structures of a patient and/or the anatomical structures of the patient can be measured. This step can include acquiring an image of the oral cavity and airway, using CT or MR, as a digital measurement. At box 1204, identify the tumor location and other critical anatomic structures, such as blood vessels. At box 1206, make measurements of the oral cavity and airway to inform the new retractor design. In an embodiment, this can include segmenting the oral cavity and airway to produce a 3D model of the anatomy. The 3D model can be a physical model or a digital model. At box 1208, customize the design of the retractor to create a patient specific design. The design of the retractor can be based on multiple factors, and can include extending or shortening the length of the blade, changing the blade curvature, etc. This can also include changing the shape of the retractor so that certain regions are cut away to provide access for the surgeon to reach anatomy associated with a tumor, or other customizations that aid a surgeon in removing a specific tumor at a specific location in a specific patient's anatomy, or other customizations to protect patient anatomy such as blood vessels. The size and/or shape of a surgical tool(s) to be used can be a factor. Other factors may be obvious to a person skilled in the art. A retractor can be customized to the patient based on factors that the designer deems to be important for the application of the retractor. At 1206, a customized retractor can be printed using a 3D printer of any acceptable type and operating modality or can be machined or injection molded using biocompatible materials. A customized laryngoscope can be printed thereby, using polymers such as MED610 from Stratasys. The customized retractor can then be used in surgery, including IGTORS.

FIG. 12B is a flowchart describing the use of a retractor and support rig to obtain images to inform a surgery, according to an embodiment. At 1212, a user, such as a doctor or hospital, can obtain at least one pre-operative image of anatomical structures of a patient. The images can be taken while the patient is awake or sedated, seated, lying down, or in another position, with or without the head tilted back, and with or without a retractor inserted. The medical provider can use the obtained image to determine the locations of anatomical structures that may require surgery. 1214 can include patient management. At 1214, the patient can be sedated and/or placed on a platform 602 that is on a patient support surface such as in imaging table. At 1216, the user can insert the retractor, assemble the support rig including the platform that is under the patient, and attach the retractor to the support rig. At 1218, the user can adjust the position and/or orientation of the retractor. The user can place the retractor in a position and orientation that the user estimates is optimal for the medical procedure, which can include viewing the anatomical structures and/or performing surgery. The user can fix the position and orientation of the retractor relative to the patient. The user's estimate of an optimal position and orientation of the retractor can be informed by an image taken before the retractor is inserted. At 1220, an image can be taken of the patient with the inserted retractor supported by the rig. The patient can be lying on an imaging table with a retractor inserted and with the retractor supported by a rig. An image can be taken of the anatomical structures of the patient with the radiolucent and metal-free retractor inserted and supported by the rig. At 1222, a user can review the image taken at 1220, and can determine if the retractor is correctly positioned and oriented, based on the actual location of a targeted anatomical structure, such as a tumor. If the retractor is correctly positioned and oriented relative to the target anatomical structure, the user and patient can proceed to surgery. If an adjustment to the position and/or orientation of the retractor could put the retractor into a better position and/or orientation for the medical procedure, the user can return to 1218, and the user can repeat as necessary unto the retractor is in the desired position and orientation relative to an anatomical structure of the patient.

Figure 12C:
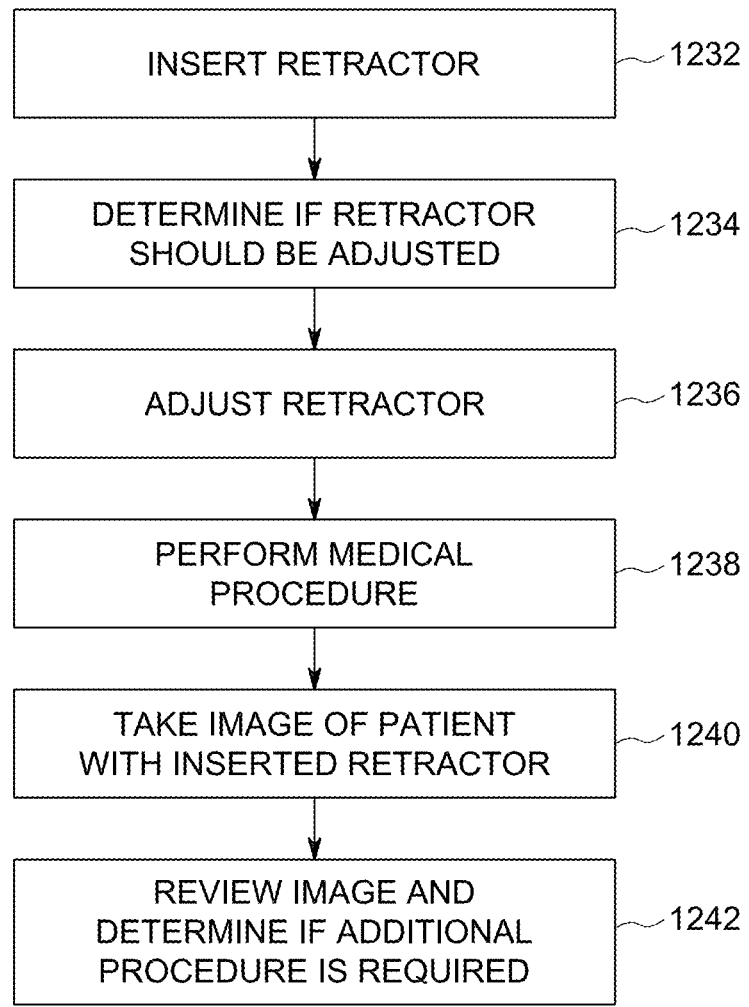
FIG. 12C is a flowchart describing the use of a laryngoscope and support rig during a medical procedure.

FIG. 12C is a flowchart describing the use of a retractor and support rig during a medical procedure. At 1232, the user can insert a retractor, assemble the support rig including the platform that is under the patient, and attach the retractor to the support rig. At 1234, the user can determine if the position and/or orientation of the retractor should be adjusted. If the retractor does not need adjusted, the user can proceed to step 1236. If the retractor should be adjusted, the user can proceed to step 1236. At step 1236, the user can adjust the position and/or orientation of the retractor, if necessary. The user can move the elbow assembly in a proximal and/or distal direction on the arm, the user can adjust the angle of the elbow, the user can adjust the distance between the elbow and the retractor, the user can adjust the mouth opening distance, and the user can adjust the depth of the tongue blade. The user can place the retractor in a position and orientation that the user estimates is optimal for the medical procedure, which can include viewing the anatomical structures and/or performing surgery by inserting medical instruments into the oral cavity, including robotic instruments. The user can fix the position and orientation of the retractor relative to the patient. The user's estimate of an optimal position and orientation of the retractor can be informed by an image taken of the anatomical structures before the medical procedure is performed. At 1238, the user can perform the medical procedure. This can include viewing the anatomical structures, directly and/or with the use of imaging equipment, and performing a surgery that can include robotic instruments. IGTORS surgery can include simultaneous imaging during the surgery to guide a surgeon to perform a surgery such as removing a tumor. Performing surgery while simultaneously taking images substantially increases the accuracy of tumor removal by the surgeon, so that all of the tumor can be removed without damage to nearby anatomical structures.

At 1240, additional images can be taken of the anatomical structures of the patient. The image is taken while the retractor remains in the patient and can be taken while the retractor is supported by the rig and remains in a fixed position and orientation relative to the patient. At 1242, the user can review the image taken at 1240, and can determine if additional medical procedures are required, and what additional medical procedures are required. If the user determines that additional procedures are required, the user can return to step 1234 and repeat as necessary.

III. Exemplary Retractor Design and Use

A. Retractor Fabrication

Figure 13:
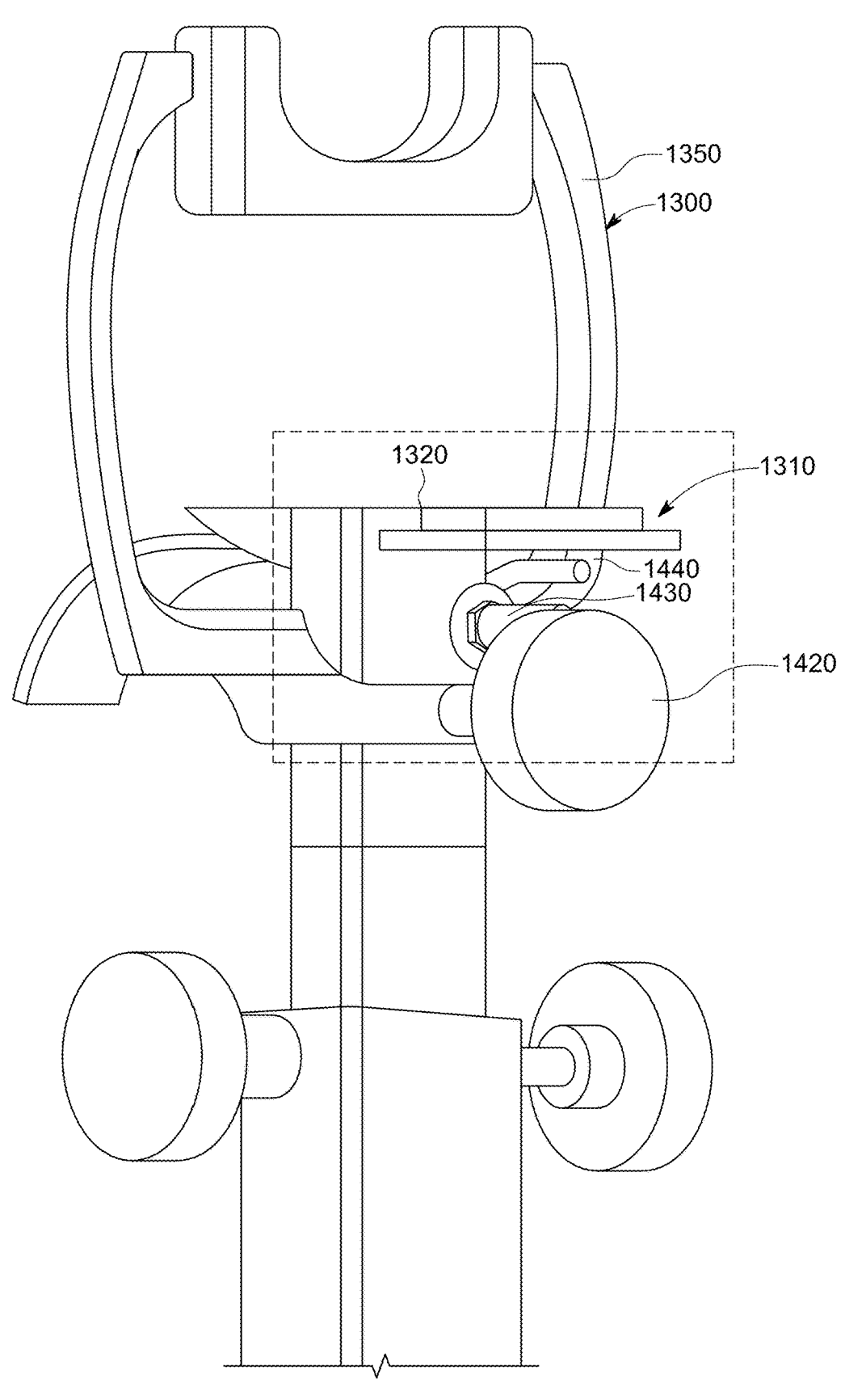
FIG. 13 is a partial perspective view of a retractor according to an alternate embodiment.
Figures 14, 15:
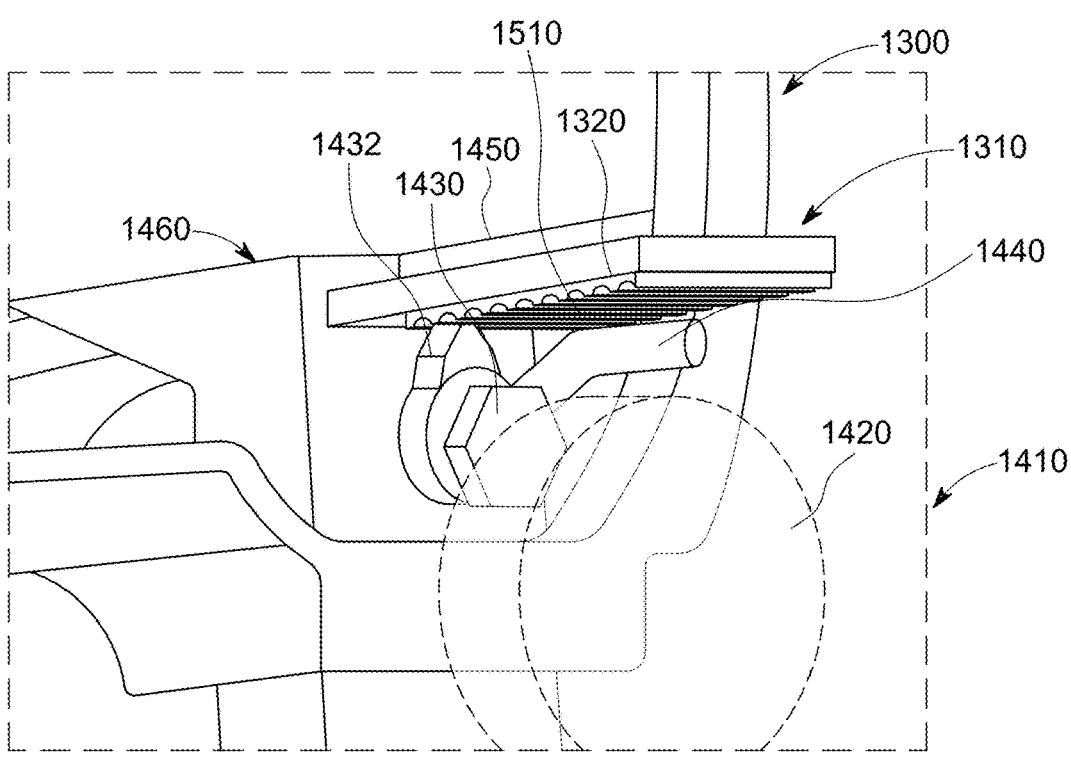
FIG. 14 is a more detailed, fragmentary perspective view of the movable tongue blade and base assembly with associated locking can and set screw assembly for the retractor of FIG. 13.
FIG. 15 is fragmentary side view of the movable tongue blade and base assembly of FIG. 14.

In an exemplary embodiment, structural supports and/or using high strength 3D printing materials can be added to enhance the strength of the retractor system. FIGS. 13-15 show diagrams of the retractor 1300 with a blade locking mechanism 1310 according to an exemplary embodiment. The locking mechanism 1310 consist of a set screw assembly 1410 with associated set screw 1420 (described below) and 1430, as well as a cam 1432 that rotates (double-curved arrow 1436) to selectively engage and disengage grooves 1510 on the underside of the movable tongue blade 1320. The cam 1432 is rotated (double-curved arrow 1436) using a lever 1440. The cam 1432 can be tightened in engagement with the grooves 1510 using the screw 1430, or the screw 1430 can exert sufficient interengaging friction with the cam 1432 to prevent inadvertent disengagement of the cam from a selected tongue blade groove 1510.

Figure 16:
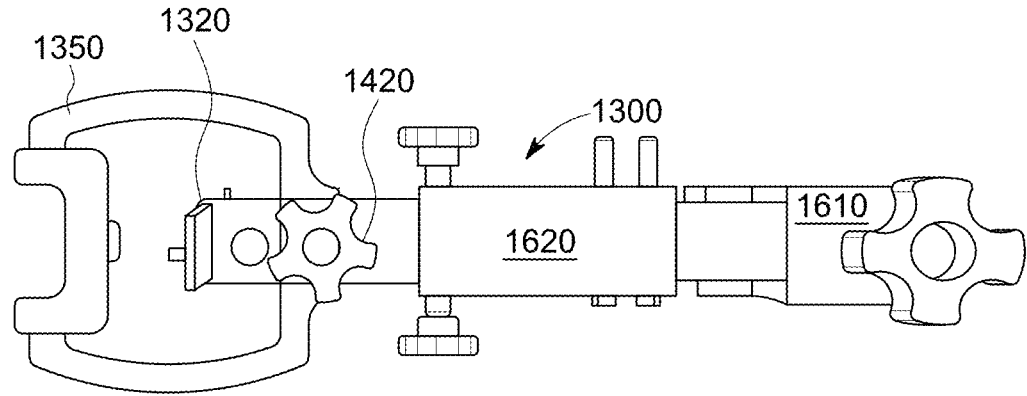
FIG. 16 is an overall top view of the overall retractor of FIG. 13, including adjustable arm and shell base for attachment to a support stand/rig.
Figure 17:
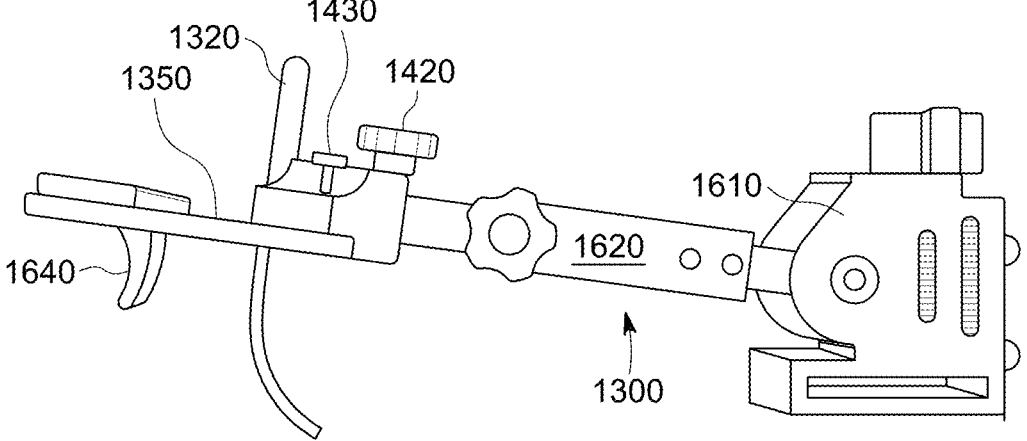
FIG. 17 is a side view of the overall retractor of FIG. 16.

As shown further in FIGS. 16 and 17, the complete retractor 1300 according to the exemplary embodiment components can be constructed from a variety of techniques from appropriate polymers. Such techniques can include, but are not limited to molding, extrusion and 3D printing. Note that any elements not further described in this embodiment are structurally and functionally similar to the above-described embodiments. In general, the retractor 1300 includes an arm assembly that is attached to a support/shell adapted to attach to a support stand/rig. The support/shell allows the relative angle of the arm assembly/retractor to be adjusted using (e.g.) a worm gear assembly that causes the proximal end of the arm assembly to rotate about a pivot. The arm assembly telescopes relative to a sleeve and can be fixed at a desired length using a sleeve that has a screw and pins that pass through a series of spaced-apart through-holes in the arm assembly. The tongue blade base includes a series of parallel grooves that engage a rotating, locking cam on the tongue blade base to selectively lock and unlock slidable movement of the tongue blade relative to its base. The tongue blade base is fixed on the end of the telescoping portion of the arm assembly, and an open frame body containing the distal maxillary blade (opposite the tongue blade) is slidable along the (telescoping) arm assembly portion to adjust the mouth opening size. A set screw fixes the body in position with respect to the arm portion.

More particularly, the exemplary embodiment of the retractor 1300 further incorporates a transverse rib (not visible, see 926 above) on the tongue blade 1320 and associated set screw housing 1460, and the use of (e.g.) 3D printing the retractor system in high-strength materials. For example, such materials can include Onyx/carbon fiber (CF) composite (tongue blade 1320) and Nylon 12 (worm gear mounting base 1610, arm 1620 and maxillary blade assembly 1640). CF construction is desirable for components expecting high loads. The tongue blade 1320 and its housing can be 3D-printed with Onyx matrix reinforced with carbon fiber using (e.g.) a Markforged X7 printer (available from Markforged of Watertown, MA), while the remaining components can be 3D-printed with Nylon 12 on an (e.g.) HP MultiJet Fusion 580 printer (available from Hewlett Packard of Palo Alto, CA). Moreover, to improve the smoothness of device adjustments, control resolution, and ease of use, pins are implemented using polymer set screws to secure components that require active adjustments and the blade locking mechanism employs the depicted cam 1432, which rotates into the grooves 1510 in the manner of a rack and pinion beneath the tongue blade 1320, so as to readily lock the blade in place in a desired position. As shown, like other above-described embodiments, the longer tongue blade 1320 and shorter maxillary blade 1640 are curved away from each other, in each of opposing directions, to engage the tongue and upper jaw regions, respectively, while the body 1350 provides a large passage for entrance of various surgical and diagnostic tools into the patient's mouth with the tongue in a depressed position. In particular the expansion of the opposing blades is effected by loosening set screw 1420 to allow the body 1350 to slide on the proximal arm portion, relative to the tongue blade 1320 and its base, and then, when an appropriate expansion is achieved, the set screw is tightened to lock the body and associated maxillary blade 1640 with respect to the tongue blade 1320 with the subject's mouth fully opened and tongue depressed for access to the oropharynx.

B. Exemplary CT and MR Imaging of Retractor In Vivo

Figure 18:
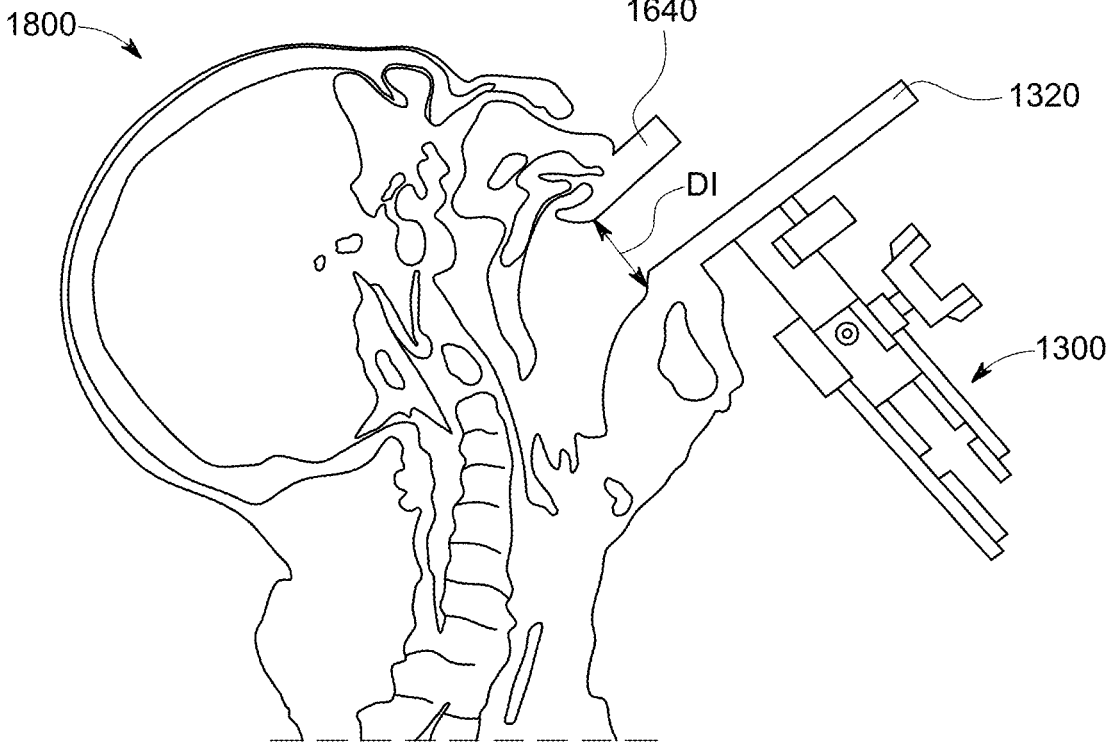
FIG. 18 is a diagram showing an outline of a CT image of the sagittal profile of a human subject's head with the retractor inserted into the subject's mouth and in a deployed orientation.

FIG. 18 shows a (e.g. 64-slice) CT image 1800 of the sagittal profile of a human subject's head with the retractor 1300 inserted and adjusted to allow passage of implements into the mouth. Note particularly that the tongue blade 1320 and maxillary blade 1640 are fully engaged and allow for the passage of implements through the subject's mouth. The exemplary Onyx/CF composite and Nylon materials used for the retractor 1300 exhibit radiolucency, and the deployed retractor desirably achieves an inter-incisive distance DI of approximately 38.01 mm.

Figure 19:
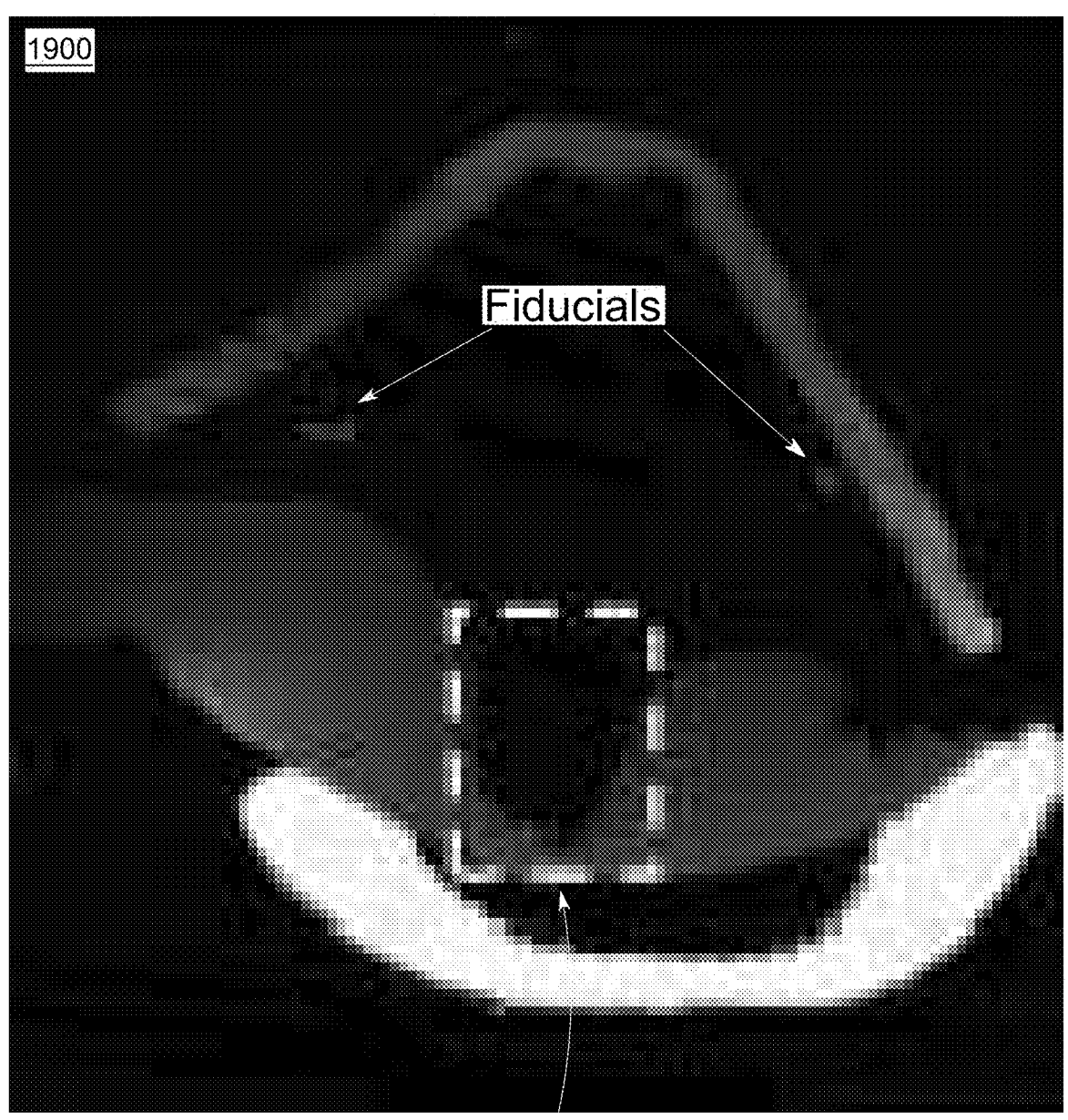
FIG. 19 is a diagram showing an axial MR image of the retractor on a saline bag and between two silicone pads, and in which fiducial markers are placed on the retractor as landmarks to assist visualization.
Figure 20:
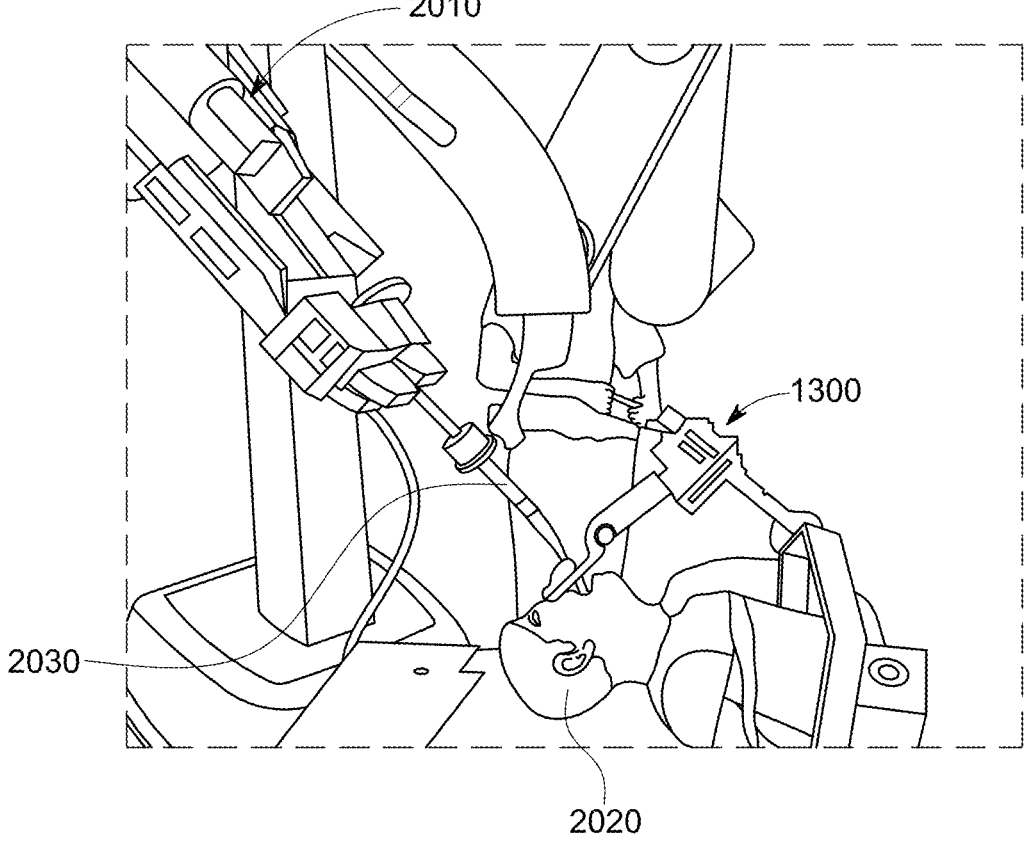
FIGS. 20-21 are diagrams showing tests of compatibility between the retractor of FIG. 13 and a common robotic surgical systems, in which ear-nose-throat (ENT) medical practitioners preform mock surgical tasks on a medical mannequin.
Figure 21:
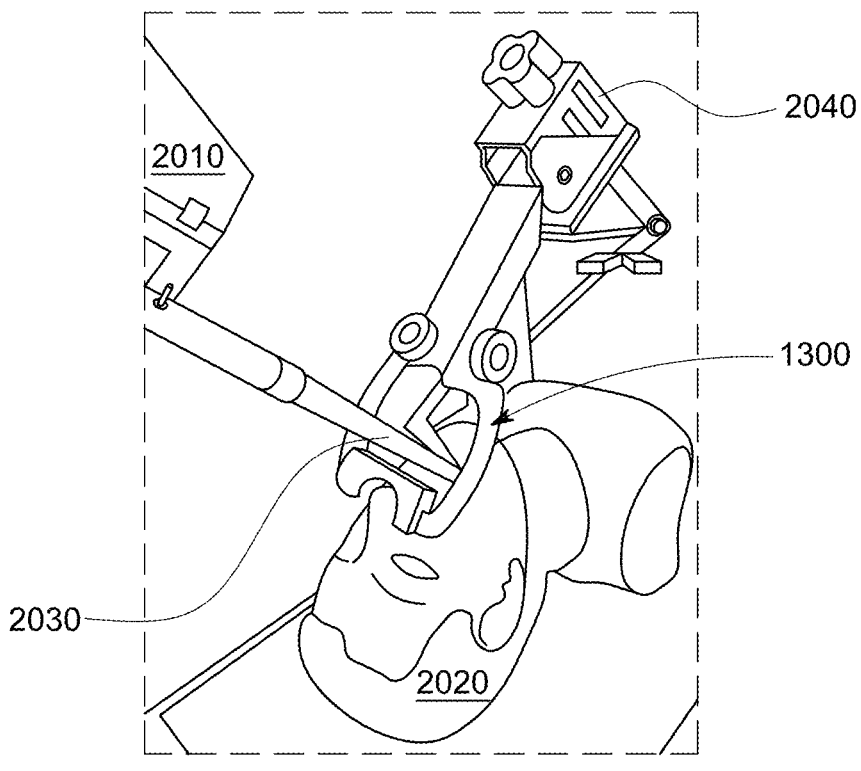

FIG. 19 shows an axial MR image of the retractor on a saline bag and between two silicone pads. In this exemplary image, fiducial markers are placed on the retractor as landmarks to assist visualization. The imaged tongue blade is positioned against the saline bag to create an indentation (region outlined by dashed box 1920), mimicking the clinical situation where the tongue blade indents soft tissues. In general the retractor shows up as substantially transparent/invisible in and air background with similar MR signals as air and is largely free of image artifacts (FIG. 19). The exemplary fiducials are visible and assist with localization of retractor components in this operational example.

In operation, compatibility between the polymer retractor and common da Vinci robotic surgical systems can be confirmed as depicted in FIGS. 20-23, in which ear-nose-throat (ENT) medical practitioners are depicted performing two mock surgical tasks using the robot with the retractor 1300 positioned for optimal exposure-more particularly suturing in an airway mannequin 2020 using a da Vinci robotic manipulator 2010 and associated invasive implement 2030 (e.g. an endoscope with visual imaging sensor).

Note that the retractor 1300 is mounted firmly in position using an articulated stand (support rig) 2040, or similar overlying base.

Figure 22:
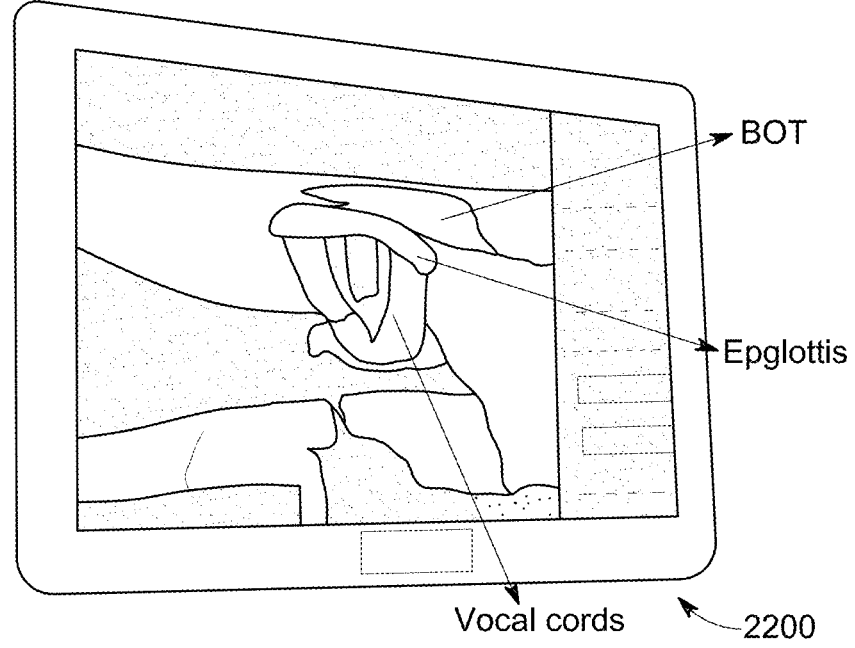
FIGS. 22-23 are diagrams representing respective display images of views from the video feed of an endoscope used in the procedures of FIGS. 20-21, showing significant anatomic sites (e.g. epiglottis, BOT, vocal cords, etc.) and sutures.
Figure 23:
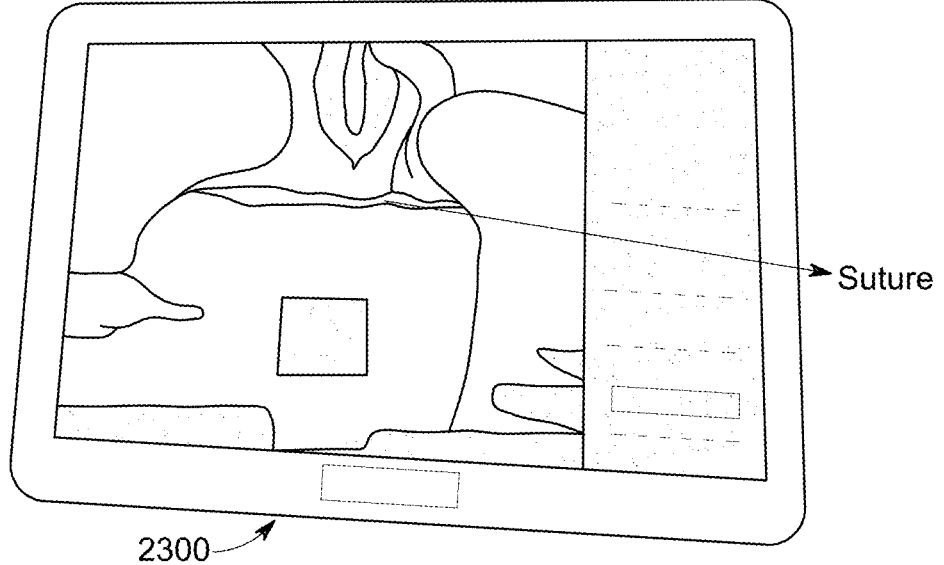

FIGS. 22 and 23 are respective display images 2200 and 2300 of views from the video feed of the endoscope 2030, showing significant anatomic sites (e.g. epiglottis, BOT, vocal cords, etc.) and sutures (FIG. 23) readily visible.

In the first task, as described above, three robotic arms are able to fit in the retracted oral cavity and move without interference therebetween. This arrangement has allowed for suturing at vocal cords free of any major collisions between the retractor and robotic instruments.

A further operational task (not shown) can include use of two robotic arms equipped with surgical instruments (e.g., grasper and cautery) that can both readily enter the retracted field. Once the endoscope was in place, all robotic instruments can typically move and function properly without major collisions. In both of the above described operational tasks, the polymer retractor can provide excellent strength and exposure with inter-incisive distances of approximately 35 mm (first task) and 40 mm (second task) and with typical anatomic landmarks (e.g. epiglottis, BOT, vocal cords, etc.) readily imaged and viewable. After hours of use, and with the exemplary materials used on the retractor, associated retractor components have been shown to be free of any visible deformations both during, and at the end of, procedures.

Figure 24:
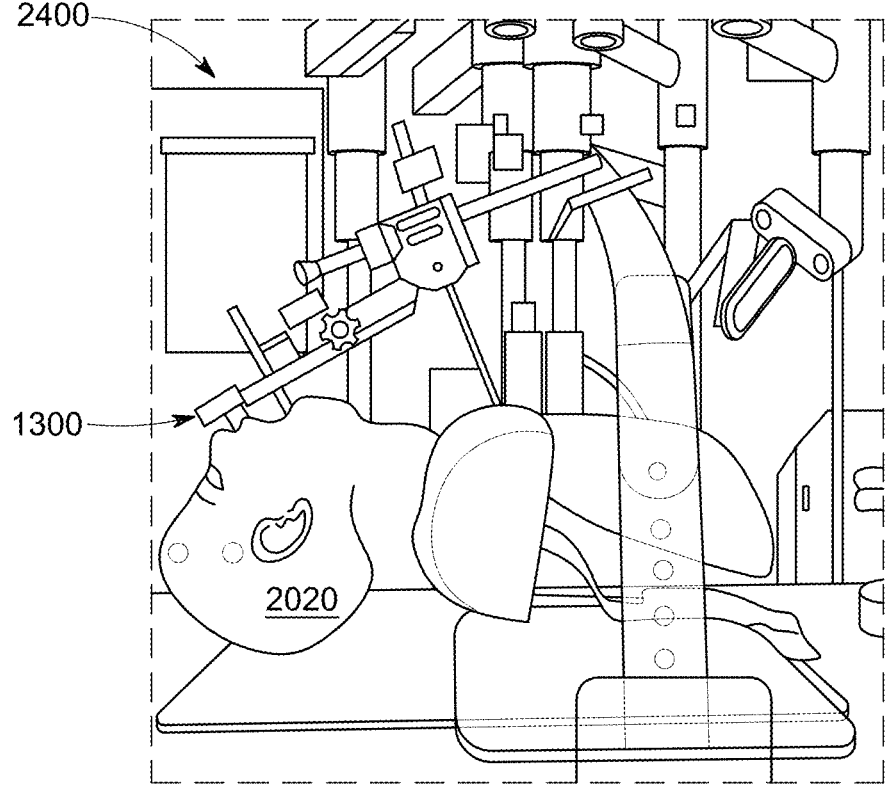
FIG. 24 is a diagram showing the retractor of FIG. 13 positioned in an airway mannequin.
Figure 25:
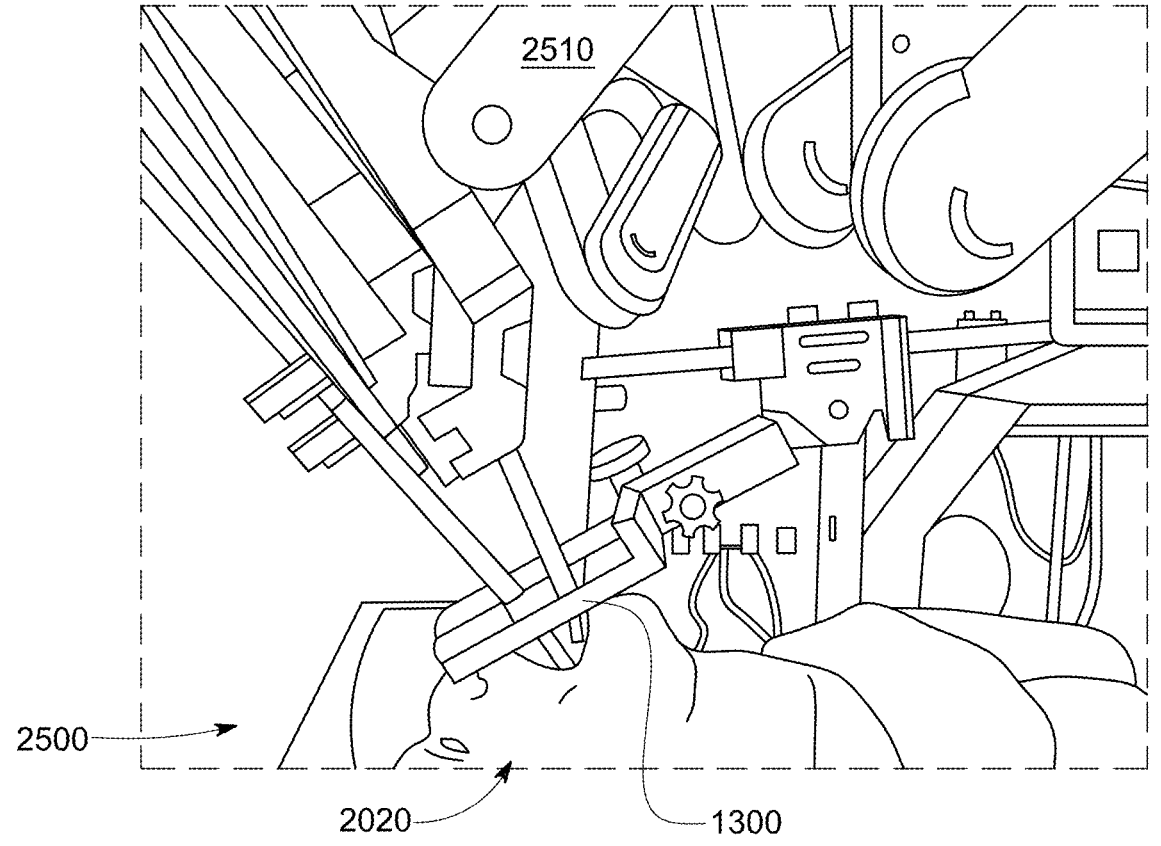
FIG. 25 is a diagram of an exemplary surgical robotic system docked in place and robotic instruments positioned in the oral cavity of the mannequin while the retractor of FIG. 13 is deployed in the mannequin's mouth.
Figure 26:
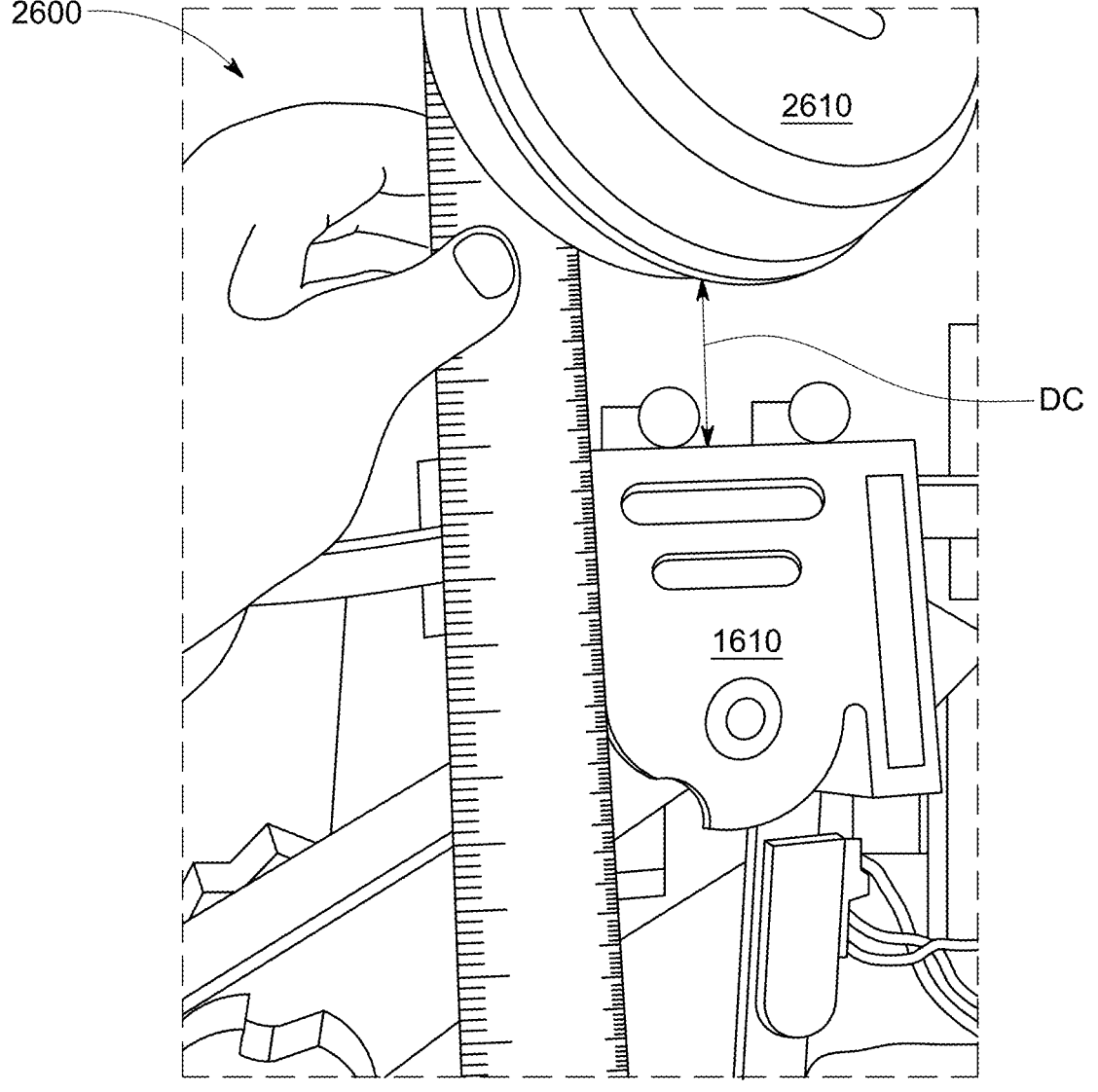
FIG. 26 is a diagram showing a clearance distance C between the top of the worm gear base of the retractor of FIG. 13 (see FIGS. 16 and 17) and a camera arm joint.

FIG. 24 shows a diagram 2400 of the retractor system 1300 positioned in an airway mannequin 2020. FIG. 25 is a diagram of a (e.g.) da Vinci Xi robotic system 2510 docked in place and robotic instruments positioned in the oral cavity while the retractor 1300 is in place. Finally, FIG. 26 is a diagram 2600, showing a clearance distance DC between the top of the worm gear base 1610 and a camera arm joint 2610. In operation an ENT surgeon has adjusted the endoscope position and moved the robotic instruments into various orientations/positions so as to mimic a normal TORS procedure and no motion interference has been observed with a clearance DC of approximately 2 centimeters.

C. Clinical Use of the Retractor

While the exemplary 3D printing materials of the retractor components are not inherently sterile, such can be sterilized using conventional techniques and components with direct patient contact can be wrapped in sterile covers such as ultrasound probe covers. Furthermore, the relatively low printing cost and quick turnaround allow components with direct patient contact to be limited to single use, and potentially customized to the patient's particular size and/or anatomical features. Alternatively, the retractor of this and other embodiments herein can be mass-produced in one or more sizes (for example, adult, pediatric and infant size(s)), and/or can be constructed from materials having anti-microbial properties.

IV. Conclusion

It should be clear that the retractor system described according to the above embodiments, provides a highly useful tool for both the manual and robotic surgeries involving the mouth and throat region, as well as other internal regions that are accessed through the mouth. The retractor can be constructed from polymer materials that are largely transparent to most forms of imaging. The materials or relatively inexpensive, are capable of sterilization, and can be manufactured using rapid prototyping techniques, such as 3D printing. Notably, the retractor provides significant clearance for the insertion of multiple instruments during a procedure.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, different embodiments of wrists can incorporate different types of hinges, including hinges that enable movement of the arm through three dimensions, such as a ball-and-socket type joint, or other hinges that enable movement in multiple directions. A laryngoscope and an elbow assembly can be designed to snap together or use other engagement means that can be free of bolts or pins. Additionally, while a pair of clamps are shown, a unitary or integral clamping assembly that is bolted to the collar (e.g. at the front and rear as shown herein) can be employed in alternate embodiments. Also, as used herein, various directional and orientational terms (and grammatical variations thereof) such as "vertical", "horizontal", "up", "down", "bottom", "top", "side", "front", "rear", "left", "right", "forward", "rearward", and the like, are used only as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Accordingly, this description is meant to be taken only by way of example, and not to otherwise limit the scope of this invention.

What is claimed is:

1. A method of manufacturing a customized radiolucent and MR compatible retractor for use in image guided trans-oral robotic surgery, the method comprising the steps of:

acquiring an image of an oral cavity and airway of a patient;

identifying a location of a tumor;

making a 3D model representing associated anatomy;

designing a customized retractor based on the 3D model and the location of the tumor, wherein designing the customized retractor comprises modifying geometry of at least one of a tongue blade or a maxillary blade to provide surgical access to the identified tumor based on its position in the 3D model of the patient's anatomy; and 3D printing the customized retractor based upon the step of designing.

2. The method as set forth in claim 1 wherein the step of 3D printing includes printing a maxillary blade supported by a body that enables one or more surgical instruments to pass therethrough and is movable relative to a tongue blade to allow a retraction operation on the patient.

3. The method as set forth in claim 2 wherein the step of 3D printing further comprises constructing the tongue blade to be movable transversely to the body.

4. The method as set forth in claim 2 wherein the maxillary blade is constructed from a Nylon material and the tongue blade is constructed by 3D printing with a carbon fiber-reinforced composite material selected for use within an MR imaging field.

5. The method as set forth in claim 4 wherein the tongue blade includes a grooved rack and that slidably engages a tongue blade base having a cam for locking and unlocking a slidable adjustment position of the tongue blade relative to the body.

6. The method as set forth in claim 5 wherein the retractor includes an arm assembly adapted to mount, at a proximal end of the retractor, to a support stand, the arm being adjustable in length of extension to thereby move the tongue blade and maxillary blade.

7. The method as set forth in claim 6 wherein the arm assembly includes, at the proximal end, a support that allows for an angle of the arm assembly to be adjusted using a worm gear.

8. The method as set forth in claim 7 wherein the tongue blade base adjustably moves along the arm assembly so as to vary a distance between the tongue blade and the maxillary blade.

9. The method as set forth in claim 8 wherein the tongue blade base includes a set screw to fix a position thereof relative to the arm assembly.

10. The method as set forth in claim 1, further comprising, adjusting an overall length of the arm assembly by moving a telescoping portion of the arm assembly relative to a sleeve and fixing the portion with respect to the sleeve in a desired position.

11. The method as set forth in claim 1, wherein the customized retractor design includes cut-away or relief regions aligned with the tumor site to optimize access and reduce obstruction in an image-guided robotic procedure.

* * * * *